US012201652B2

(12) United States Patent
Gilbert et al.

(10) Patent No.: US 12,201,652 B2
(45) Date of Patent: Jan. 21, 2025

(54) INTRACELLULAR DELIVERY OF BIOMOLECULES TO INDUCE TOLERANCE

(71) Applicant: STEMCELL TECHNOLOGIES CANADA INC., Vancouver (CA)

(72) Inventors: Jonathan B. Gilbert, Somerville, MA (US); Bu Wang, Watertown, MA (US); Scott Loughhead, Watertown, MA (US); Howard Bernstein, Cambridge, MA (US); Armon R. Sharei, Watertown, MA (US); Finola Moore, Watertown, MA (US)

(73) Assignee: Stemcell Technologies Canada Inc., Vancouver (CA)

( * ) Notice: Subject to any disclaimer, the term of this patent is extended or adjusted under 35 U.S.C. 154(b) by 1012 days.

(21) Appl. No.: 16/098,404

(22) PCT Filed: May 3, 2017

(86) PCT No.: PCT/US2017/030932

§ 371 (c)(1),
(2) Date: Nov. 1, 2018

(87) PCT Pub. No.: WO2017/192785

PCT Pub. Date: Nov. 9, 2017

(65) Prior Publication Data

US 2019/0111082 A1 Apr. 18, 2019

Related U.S. Application Data

(60) Provisional application No. 62/331,368, filed on May 3, 2016.

(51) Int. Cl.

| | |
|---|---|
| ***A61K 35/18*** | (2015.01) |
| ***A61K 35/19*** | (2015.01) |
| ***A61K 39/00*** | (2006.01) |
| ***A61K 39/385*** | (2006.01) |
| ***A61P 37/06*** | (2006.01) |
| ***C12M 1/12*** | (2006.01) |
| ***C12M 3/06*** | (2006.01) |
| ***C12N 5/078*** | (2010.01) |
| ***C12N 15/85*** | (2006.01) |
| ***C12N 15/87*** | (2006.01) |

(52) U.S. Cl.

CPC .............. *A61K 35/18* (2013.01); *A61K 35/19* (2013.01); *A61K 39/001* (2013.01); *A61K 39/385* (2013.01); *A61K 39/461* (2023.05); *A61K 39/4622* (2023.05); *A61K 39/4632* (2023.05); *A61K 39/464* (2023.05); *A61K 39/464411* (2023.05); *A61K 39/464838* (2023.05); *A61P 37/06* (2018.01); *C12M 1/12* (2013.01); *C12M 3/06* (2013.01); *C12N 5/0644* (2013.01); *C12N 15/85* (2013.01); *C12N 15/87* (2013.01); *A61K 2039/507* (2013.01); *A61K 2039/572* (2013.01); *A61K 2039/6006* (2013.01); *A61K 2039/62* (2013.01); *A61K 2039/64* (2013.01)

(58) Field of Classification Search

CPC ..................................................... A61K 35/18

See application file for complete search history.

(56) References Cited

U.S. PATENT DOCUMENTS

| | | | |
|---|---|---|---|
| 4,055,799 | A | 10/1977 | Coster |
| 4,321,259 | A | 3/1982 | Nicolau |
| 4,327,710 | A | 5/1982 | Deloach |
| 4,376,634 | A | 3/1983 | Prior et al. |
| 4,478,824 | A | 10/1984 | Franco |
| 4,652,449 | A | 3/1987 | Ropars |
| 4,752,586 | A | 6/1988 | Ropars |
| 4,835,457 | A | 5/1989 | Hanss |
| 5,023,054 | A | 6/1991 | Sato |
| 5,372,942 | A | 12/1994 | Mcgarrity |
| 5,589,389 | A | 12/1996 | Pages |
| 5,612,207 | A | 3/1997 | Nicolau |
| 5,622,963 | A | 4/1997 | Armstrong |
| 5,736,507 | A | 4/1998 | Boots |
| 5,916,793 | A | 6/1999 | Filpula |
| 6,139,836 | A | 10/2000 | Magnani |

(Continued)

FOREIGN PATENT DOCUMENTS

| | | | |
|---|---|---|---|
| CN | 101031339 | A | 9/2007 |
| CN | 101031641 | A | 9/2007 |

(Continued)

OTHER PUBLICATIONS

Fourlanos et al. (2011, Diabetes, vol. 60, pp. 1237-1245). (Year: 2011).*

(Continued)

*Primary Examiner* — Anoop K Singh

*Assistant Examiner* — David A Montanari

(74) *Attorney, Agent, or Firm* — SMART & BIGGAR LP; Micheline Gravelle

(57) ABSTRACT

The present invention provides methods for inducing tolerance and/or suppressing an immune response to an antigen by passing a cell suspension containing an anucleate cell through a constriction, wherein the constriction deforms the cell thereby causing a perturbation of the cell such that an antigen and/or tolerogenic factor enters the cell. In some embodiments, the anucleate cell is delivered to an individual and the antigen is delivered to and processed in a tolerogenic environment to induce tolerance and/or suppress an immune response to the antigen.

37 Claims, 15 Drawing Sheets

(56) References Cited

U.S. PATENT DOCUMENTS

| | | | |
|---|---|---|---|
| 6,218,166 | B1 | 4/2001 | Ravindranath |
| 6,610,702 | B2 | 8/2003 | Lehn |
| 6,737,259 | B1 | 5/2004 | Clark |
| 6,812,204 | B1 | 11/2004 | Mchale |
| 7,037,500 | B1 | 5/2006 | Silverstein |
| 7,071,297 | B2 | 7/2006 | Wraith |
| 7,485,314 | B2 | 2/2009 | Kakkis |
| 7,704,743 | B2 | 4/2010 | Fedorov |
| 8,147,867 | B2 | 4/2012 | Hong |
| 8,679,751 | B2 | 3/2014 | Huang |
| 9,364,504 | B2 | 6/2016 | Godfrin |
| 9,950,049 | B2 | 4/2018 | Godfrin |
| 10,124,336 | B2 | 11/2018 | Sharei |
| 10,526,573 | B2 | 1/2020 | Ding |
| 10,696,944 | B2 | 6/2020 | Sharei |
| 10,780,151 | B2 | 9/2020 | Godfrin |
| 10,870,112 | B2 | 12/2020 | Sharei |
| 11,111,472 | B2 | 9/2021 | Sharei et al. |
| 11,125,739 | B2 | 9/2021 | Sharei et al. |
| 2003/0045467 | A1 | 3/2003 | Orban |
| 2004/0197898 | A1 | 10/2004 | Nakatani |
| 2006/0002915 | A1 | 1/2006 | Min |
| 2006/0134067 | A1 | 6/2006 | Liu |
| 2006/0134772 | A1 | 6/2006 | Miles |
| 2006/0188490 | A1 | 8/2006 | Hoerr |
| 2006/0193869 | A1 | 8/2006 | Barrat |
| 2007/0243523 | A1 | 10/2007 | Ionescu-Zanetti |
| 2007/0249038 | A1 | 10/2007 | Adamo |
| 2008/0026465 | A1 | 1/2008 | Nakata |
| 2008/0261262 | A1 | 10/2008 | Godfrin |
| 2008/0274092 | A1 | 11/2008 | Godfrin |
| 2008/0311140 | A1 | 12/2008 | Lee |
| 2009/0092637 | A1 | 4/2009 | Ludvigsson |
| 2009/0238818 | A1 | 9/2009 | Kakkis |
| 2009/0280518 | A1 | 11/2009 | Adamo |
| 2010/0203068 | A1 | 8/2010 | Betz |
| 2010/0249621 | A1 | 9/2010 | Ichitani |
| 2010/0266571 | A1 | 10/2010 | Lockhart |
| 2011/0030808 | A1 | 2/2011 | Chiou |
| 2011/0123561 | A1 | 5/2011 | Barrat |
| 2011/0300205 | A1 | 12/2011 | Geall |
| 2012/0009140 | A1 | 1/2012 | Godfrin |
| 2012/0064505 | A1 | 3/2012 | Suresh |
| 2012/0207745 | A1 | 8/2012 | Godfrin |
| 2012/0322157 | A1 | 12/2012 | Yohn |
| 2014/0287509 | A1 | 9/2014 | Sharel |
| 2015/0184127 | A1 | 7/2015 | White |
| 2016/0193605 | A1 | 7/2016 | Sharei |
| 2016/0324946 | A1 | 11/2016 | Godfrin |
| 2018/0003696 | A1 | 1/2018 | Sharei |
| 2018/0016539 | A1 | 1/2018 | Ding |
| 2018/0142198 | A1 | 5/2018 | Sharei |
| 2018/0201889 | A1 | 7/2018 | Sharei |
| 2018/0245089 | A1 | 8/2018 | Sharei |
| 2018/0344822 | A1 | 12/2018 | Godfrin |
| 2019/0017072 | A1 | 1/2019 | Ditommaso |
| 2019/0030536 | A1 | 1/2019 | Sharel |
| 2019/0093073 | A1 | 3/2019 | Sharei |
| 2019/0111082 | A1 | 4/2019 | Gilbert |
| 2019/0382796 | A1 | 12/2019 | Gilbert |
| 2020/0277566 | A1 | 9/2020 | Sharei |
| 2020/0316604 | A1 | 10/2020 | Dadgar |
| 2020/0318066 | A1 | 10/2020 | Sharei |
| 2020/0332243 | A1 | 10/2020 | Dadgar et al. |
| 2021/0038709 | A1 | 2/2021 | Loughhead |
| 2021/0077602 | A1 | 3/2021 | Godfrin et al. |
| 2021/0113628 | A1 | 4/2021 | Loughhead et al. |
| 2021/0138050 | A1 | 5/2021 | Loughhead et al. |
| 2021/0170411 | A1 | 6/2021 | Sharei et al. |
| 2021/0268082 | A1 | 9/2021 | Godfrin et al. |
| 2021/0317187 | A1 | 10/2021 | Sharei et al. |

FOREIGN PATENT DOCUMENTS

| | | | | | |
|---|---|---|---|---|---|
| CN | 103987836 | A | | 8/2014 | |
| CN | 104203277 | A | * | 12/2014 | ............ A61K 39/36 |
| CN | 103987839 | B | | 4/2018 | |
| EP | 0101341 | A1 | | 2/1984 | |
| EP | 0414007 | B1 | | 2/1991 | |
| EP | 0679101 | B1 | | 11/1995 | |
| EP | 0882448 | A1 | | 12/1998 | |
| EP | 1225228 | A2 | | 7/2002 | |
| GB | 1051382 | A | | 12/1966 | |
| JP | H01196566 | A | | 8/1989 | |
| JP | H0235081 | A | | 2/1990 | |
| JP | H0253490 | A | | 2/1990 | |
| JP | H03257366 | A | | 11/1991 | |
| JP | H0662867 | A | | 3/1994 | |
| JP | H115752 | A | | 1/1999 | |
| JP | 2005530762 | A | | 10/2005 | |
| JP | 2007501200 | A | | 1/2007 | |
| JP | 2008524237 | A | | 7/2008 | |
| JP | 2010025852 | A | | 2/2010 | |
| JP | 2013536848 | A | | 9/2013 | |
| JP | 2014533936 | A | | 12/2014 | |
| KR | 20120101657 | | | 9/2012 | |
| KR | 20140115560 | A | | 10/2014 | |
| RU | 2424792 | C2 | | 7/2011 | |
| RU | 2539989 | C1 | | 1/2015 | |
| WO | 1996013517 | A1 | | 5/1996 | |
| WO | 1998039027 | A2 | | 9/1998 | |
| WO | 200007630 | A1 | | 2/2000 | |
| WO | 2001088102 | A1 | | 11/2001 | |
| WO | WO02067863 | A2 | | 9/2002 | |
| WO | WO03020039 | A1 | | 3/2003 | |
| WO | 2003064464 | A1 | | 8/2003 | |
| WO | 2003094840 | A2 | | 11/2003 | |
| WO | 2005060993 | | | 7/2005 | |
| WO | 2006016247 | A2 | | 2/2006 | |
| WO | 2006016247 | A3 | | 6/2006 | |
| WO | 2006066003 | A2 | | 6/2006 | |
| WO | 2006105251 | A2 | | 10/2006 | |
| WO | 2007067032 | A1 | | 6/2007 | |
| WO | 2008021465 | A2 | | 2/2008 | |
| WO | 2006105251 | A3 | | 3/2008 | |
| WO | 2008021465 | A3 | | 5/2008 | |
| WO | 2008129426 | A2 | | 10/2008 | |
| WO | 2008134628 | A2 | | 11/2008 | |
| WO | 2009019317 | A1 | | 2/2009 | |
| WO | 2009056332 | A1 | | 5/2009 | |
| WO | 2008129426 | A3 | | 6/2009 | |
| WO | 2008134628 | A3 | | 1/2010 | |
| WO | 2010016800 | A1 | | 2/2010 | |
| WO | 2010145849 | A2 | | 12/2010 | |
| WO | WO-2011051346 | A1 | * | 5/2011 | ............. A61P 29/00 |
| WO | 2011079217 | A1 | | 6/2011 | |
| WO | 2011119492 | A2 | | 9/2011 | |
| WO | 2010145849 | A3 | | 12/2011 | |
| WO | 2011119492 | A3 | | 4/2012 | |
| WO | 2012069568 | A2 | | 5/2012 | |
| WO | 2012074588 | A2 | | 6/2012 | |
| WO | 2012069568 | A3 | | 9/2012 | |
| WO | 2012074588 | A3 | | 10/2012 | |
| WO | WO-2013059343 | A1 | * | 4/2013 | ............ C12N 15/87 |
| WO | 2013185032 | A1 | | 12/2013 | |
| WO | 2014120956 | A1 | | 8/2014 | |
| WO | 2014165707 | A2 | | 10/2014 | |
| WO | WO2015023982 | A1 | | 2/2015 | |
| WO | 2014165707 | A3 | | 3/2015 | |
| WO | WO2016070136 | A1 | | 5/2016 | |
| WO | WO2016077761 | A1 | | 5/2016 | |
| WO | 2016115179 | A1 | | 7/2016 | |
| WO | WO2017008063 | A1 | | 1/2017 | |
| WO | 2017041051 | A1 | | 3/2017 | |
| WO | WO2017041050 | A1 | | 3/2017 | |
| WO | 2017123663 | A1 | | 7/2017 | |
| WO | WO2017192785 | A1 | | 11/2017 | |
| WO | WO2017192786 | A1 | | 11/2017 | |
| WO | 2018106849 | A1 | | 6/2018 | |
| WO | 2019113125 | A1 | | 6/2019 | |
| WO | 2019126212 | A1 | | 6/2019 | |

(56) References Cited

FOREIGN PATENT DOCUMENTS

| | | |
|---|---|---|
| WO | 2019178005 A2 | 9/2019 |
| WO | 2019178006 A2 | 9/2019 |
| WO | 2019178005 A3 | 10/2019 |
| WO | 2019178006 A3 | 11/2019 |
| WO | 2020072833 A1 | 4/2020 |
| WO | 2020154696 A1 | 7/2020 |
| WO | 2020176789 A1 | 9/2020 |
| WO | 2020210162 A1 | 10/2020 |

OTHER PUBLICATIONS

Zhang et al. (1998, Nature Biotechnology, vol. 16, pp. 1045-1049). (Year: 1998).*

Pautard et al. (2011, J. Thrombosis and Haemostasis, vol. 9, pp. 1163-1170). (Year: 2011).*

English Translation of CN-104203277-A (Gayer et al.) (Year: 2014).*

Adamo, A. et al. (Aug. 7, 2012, e-pub. Jul. 10, 2012). "Microfluidics-Based Assessment of Cell Deformability," Anal Chem 84(15):6438-6443, 13 pages.

Adriaenssens, K. et al. (1976). "Use of enzyme-loaded erythrocytes in in-vitro correction of arginase-deficient erythrocytes in familial hyperargininemia," Clin Cher 22(3):323-326.

Banz, A. et al. (Jun. 2012). "Tumor Growth Control Using Red Blood Cells as the Antigen Delivery System and Poly (I: C)," J Immunother 35(5):409-417.

Bax, B.E. et al. (Jun. 2000). "In Vitro and In Vivo Studies with Human Carrier Erythrocytes Loaded with Polyethylene Glycol-Conjugated and Native Adenosine Deaminase," Br. J. Haematol. 109(3):549-554.

Bolhassani, A. et al. (Feb. 1, 2014, e-pub. Oct. 15, 2013). "Polymeric Nanoparticles, Potent Vectors for Vaccine Delivery Targeting Cancer and Infectious Diseases," Hum Vaccin & Immunother 10(2):321-332.

Bouvier, M. et al. (2008). "A Novel Approach For A Specific Delivery Of Glucocerebrosidase In Bone Marrow Gaucher Cells," Abstract, Molecular Genetics And Metabolism 93(2):S17, 1 page. (Abstract).

Bratosin, D. et al. (2001). "Programmed cell death in mature erythrocytes: a model for investigating death effector pathways operating in the absence of mitochondria," Cell Death Diff. 8:1143-1156.

Bustos, N. et al. (Nov. 30, 1989, Dec. 1989). "Enzyme Replacement Therapy In Porphyrias—V. Ln Vivo Correction Of Delta-Aminolaevulinate Dehydratase Defective In Erythrocytes In Lead Intoxicated Animals by Enzyme-Loaded Red Blood Cell Ghosts," Drug Design And Delivery 5(2):125-131.

Cabantchik, Z.I. et al. (Apr. 8, 1975, e-pub. Feb. 3, 2003). "A Comparison Of Intact Human Red Blood Cells And Resealed And Leaky Ghosts With Respect To Their Interactions With Surface Labelling Agents And Proteolytic Enzymes", Biochim Biophys Acta. 382(4):621-633.

Chen, C. et al. (2009, e-pub. May 14, 2009). "Patch Clamping on Plane Glass-Fabrication of Hourglass Aperture and High Yield Ion Channel Recording," Lab Chip 9:2370-2380.

Corinti, S. et al. (Apr. 1, 2002). "Erythrocytes Deliver Tat To Interferon-Gamma-Treated Human Dendritic Cells For Efficient Initiation Of Specific Type 1 Immune Responses In Vitro" Journal Of Leukocyte Biology 71(4):652-658.

Ding, X. et al. (Mar. 9, 2017). "High-throughput nuclear delivery and rapid expression of DNA via mechanical and electrical cellmembrane disruption," Nature Biomedical Engineering 1(3):39, 15 pages.

Dioun, A. F. et al. (Jul. 1998). "IgE-Mediated Allergy And Desensitization To Factor IX In Hemophilia B", J. Allerqy Clin Immunol. 102(1):113-117.

Dong, V.M. et al. (Jul. 31, 1999). "Transplantation Tolerance: The Concept And Its Applicability", Ped. Transplant. 1993:3:181-192.

Gershon, R.K. et al. (Dec. 1971). "Infectious Immunological Tolerance," Immunology 21(6):903-914.

Hallow D.M. et al. (Mar. 1, 2008, e-pub. Sep. 18, 2007). "Shear-Induced Intracellular Loading of Cells With Molecules by Controlled Microfluidics", Biotechnology and Bioengineering 99(4):846-854.

Hamidi, M. et al. (2007, e-pub. Oct. 10, 2008). "Preparation And Validation Of Carrier Human Erythrocytes Loaded By Bovine Serum Albumin As A Model Antigen/Protein," Drug Delivery 14(5):295-300.

Hillerdal, V. et al. (Jan. 18, 2014). "Systemic Treatment With CAR-engineered T Cells Against PSCA Delays Subcutaneous Tumor Growth And Prolongs Survival Of Mice," BMC Cancer 14(30):1-9.

Hosokawa, M. et al. (Aug. 1, 2010). "Size-Selective Microcavity Array for Rapid and Efficient Detection of Circulating Tumor Cells", Analytical Chemistry 82(15):6629-6635.

Howarth, M. et al. (May 2008). "Monovalent, Reduced-Size Quantum Dots For Imaging Receptors On Living Cells," Nature Methods 5(5):397-399, 7 pages.

JIANG , L.-H.(2012). "P2X receptor-mediated ATP purinergic signaling in health and disease" Cell Health Cytoskeleton 4:83-101.

Jordan, J.A. et al. (1999). "Band-3 Crosslinking-Induced Targeting Of Mouse Carrier Erythrocytes," Biotechnol. Appl. Biochem. 29:59-65.

Jordan, J.A. et al. (Jan. 1997, e-pub. Mar. 5, 2000). "In Vitro Properties And Organ Uptake Of Rat Band 3 Cross-Linked Erythrocytes," Biochimie. 79(1):53-61. (p. 1 Only).

Ju, C. et al. (Apr. 15, 2005, e-pub. Jan. 29, 2005). "Tolerogenic Role Of Kupffer Cells In Immune-Mediated Adverse Drug Reactions", Toxicology 209(2):109-112.

Kada, G. et al. (Mar. 14, 1999). "Rapid Estimation of Avidin and Streptavidin by Fluorescence Quenching or Fluorescence Polarization," Blochim. Biophys. Acta. 1427(1):44-48.

Kim, D. et al. (2009, e-pub Apr. 13, 2009). "Microengineered Platforms for Cell Mechanobiology," Annual Review of Biomedical Engineering 11:203-233.

Kinosita, K. Jr. (Mar. 16, 1978). "Survival of Sucrose-Loaded Erythrocytes in the Circulation," Nature 272:258-260.

Kwon, Y.M. et al. (Nov. 3, 2009, e-pub. Jul. 3, 2009). "L-Asparaginase Encapsulated Intact Erythrocytes For Treatment Of Acute Lymphoblastic Leukemia (ALL)" Journal of Controlled Release 139(3):182-189, 18 pages.

Lee, L. et al. (Nov. 16, 2012, e-pub. Dec. 2012). "Non-Endocytic Delivery of Functional Engineered Nanoparticles into the Cytoplasm of Live Cells Using a Novel, High-Throughput Microfluidic Device," Nano Letters 12(12):6322-6327, 34 pages. (Including Supplemental Material).

Li, J. et al. (Oct. 31, 2017). "Microfluidic-Enabled Intracellular Delivery of Membrane Impermeable Inhibitors to Study Target Engagement in Human Primary Cells," ACS Chemical Biology 12(12):2970-2974.

Liang, X. et al. (Aug. 20, 2015, e-pub. May 21, 2015). "Rapid and Highly Efficient Mammalian Cell Engineering via Cas9 Protein Transfection", J. Biotech 208:44-53.

Lin, B.K. et al. (Jun. 26, 2013). "Highly selective biomechanical separation of cancer cells from leukocytes using 1-19 microfluidic ratchets and hydrodynamic concentrator," Biomicrofluidics 7(3):1-11.

Liu et al. (2014, Jul. 28, 2014). "Molecular Imaging In Tracking Tumor-Specific Cytotoxic T Lymphocytes (CTLs)," Theranostics 4(10):990-1001.

Liu, W. et al. (Jan. 20, 2010). "Compact Biocompatible Quantum Dots Via RAFT-Mediated Synthesis of Imidazole-Based Random Copolymer Ligand," JACS 132(2):472-483, 27 pages.

Liu, Y et al. (Sep. 19, 2012, e-pub. Jul. 13, 2012). "Spatially Selective Reagent Delivery Into Cancer Cells Using A Two-Layer Microfluidic Culture System," Anal Chim Acta 743(1):125-130, 20 pages. (including Supplemental Material).

Lizano, C. et al. (2001). Mouse Erythrocytes As Carriers for Coencapsulated Alcohol and Aldehyde Dehydrogenase Obtained by Electroporation In vivo Survival Rate in Circulation, Organ Distribution and Ethanol Degradation,: Life Sciences 68:2001-2016.

(56) References Cited

OTHER PUBLICATIONS

Maratou, E. et al. (Apr. 2007). "Glucose Transporter Expression On The Plasma Membrane Of Resting And Activated White Blood Cells," Eur J Clin Invest 37(4):282-290.
Marketletter (Sep. 13, 1999). "Autoimmune Shares Collapse on Colloral Data in Rheumatoid Arthritis," Marketletter Pubs Ltd. (UK), Newsletter. (ISSN:0951-3175) 2 pages.
Matsui, H. et al. (Jul. 16, 2009, e-pub. May 20, 2009). "A Murine Model For Induction Of Long-Term Immunologic Tolerance To Factor VIII Does Not Require Persistent Detectable Levels Of Plasma Factor VIII And Involves Contributions From Foxp3+ T Regulatory Cells," Blood (Thrombosis and Hernostasis) 114(3):677-685.
Matthews, B.D. et al. (2006). "Cellular Adaptation to Mechanical Stress: Role of Integrins, Rho, Cytoskeletal Tension And Mechanosensitive Ion Channels," Journal of Cell Science 119:508-518.
Millan, C.G. et al. (Feb. 20, 2004, e-pub. Feb. 25, 2004). "Drug Enzyme And Peptide Delivery Using Erythrocytes As Carriers", Journal Of Controlled Release 95(1):27-49.
Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.
Plummer, E. et al. (Mar.-Apr. 2011, e-pub. Sep. 24, 2010). "Viral Nanoparticles and Virus-Like Particles: Platforms for Contemporary Vaccine Design," Wiley Interdiscip Rev Nanomed Nanobiotechnol. 3(2):174-196.
Pozzilli, P. et al. (Aug. 2000). "No effect of oral insulin on residual beta-cell function in recent-onset Type I diabetes (the IMDIAB VII)," Diabetol. 43:1000-1004.
Provotorov, V.M. et al. (Dec. 31, 2008). "The Role Of Erythrocytes In The System Of Controlled Transport Of Pharmaceutical Agents", Klin Med. 87(9):4-8, 2 pages. (Abstract Only).
Rughetti, A. et al. (Sep. 2000). "Transfected Human Dendritic Cells to Induce Antitumor Immunity", Gene Therapy 7(17):1458-1466.
Saulis, G. (Jan. 1, 2005). "The Loading of Human Erythrocytes With Small Molecules by Electroporation," Cellular & Molecular Biology Letters 10:23-55.
Serafini, S. et al. (2004). "Drug Delivery Through Phagocytosis Of Red Blood Cells," Transfus Med Hemother. 31(2):92-101.
Sharei, A. et al. (2015, e-pub. Apr. 13, 2015). "Ex Vivo Cytosolic Delivery of Functional Macromolecules to Immune Cells", PLoS One 10(4):e011803, 12 pages.
Sharei, A. et al. (Feb. 5, 2013, e-pub. Jan. 22, 2013). "A Vector-Free Mircrofuidic platform for Intracellular Delivery", Proc Natl Acad Sci U.S.A. 110(6):2082-2087.
Sharei, A. et al. (Nov. 7, 2013). "Cell Squeezing as a Robust, Microfluidic Intracellular Delivery Platform," Journal of Visualized Experiments (81):e50980, 9 pages.
Sharei, A. et al. (Oct. 31, 2012). "(483d) Microfluidic Cell Deformation As a Robust, Vector-Free Method for Cytosolic Delivery of Macromolecules," 12AIChE Proceedings Annual Meeting (https://www.aiche.org/conferences/aiche-annual-meeting/2012/proceeding/paper/483d-microfluidic-cell-deformation-robust-vector-free-method-cytosolic-delivery-macromolecules) last visited on Feb. 4, 2021, 8 pages.
Shelby, J.P. et al. (Dec. 9, 2003). "A Microfluidic Model for Single-Cell Capillary Obstruction by Plasmodium Falciparum-Infected Erythrocytes," PNAS 100(25):14618-14622.
Song, A.Y. et al. (2006). "Scientific Basis for the Use of Hypotonic Solutions with Ultrasonic Liposuction," Aesth. Plast. Surg. 30:233-238, 3 pages.
Szeto, G.L. et al. (May 22, 2015). "Microfluidic Squeezing for Intracellular Antigen Loading in Polyclonal B-Cells as Cellular Vaccines," Scientific Reports 5:10276, 13 pages.
Tacken, P. J. et al. (Oct. 2007, e-pub. Sep. 14, 2007). "Dendritic-cell immunotherapy: from ex vivo loading to in vivo targeting," Nature Reviews 7:790-802.
Tsukamoto, H. et al. (Dec. 1, 1999). "Iron Primes Hepatic Macrophages For NF-Kappab Activation In Alcoholic Liver Injury", Am .J Physiol. 277(6):G1240-G1250.
Turley, D.M. et al. (2010, e-pub. 2009). "Prospects for Antigen-Specific Tolerance Based Therapies for the Treatment of Multiple Sclerosis," (Molecular Basis of Multiple Sclerosis) Results Probl. Cell Differ. 51:217-235.
U.S. Appl. No. 16/769,993, filed Dec. 4, 2018, by Sharei et al. (Copy not submitted herewith pursuant to the waiver of 37 C.F.R. § 1.98(a)(2)(iii) issued by the Office on Sep. 21, 2004.).
U.S. Appl. No. 16/954,113, filed Dec. 18, 2018, by Loughhead et al. (Copy not submitted herewith pursuant to the waiver of 37 C.F.R. § 1.98(a)(2)(ill) issued by the Office on Sep. 21, 2004.).
U.S. Appl. No. 16/980,339, filed Mar. 11. 2019, by Loughhead et al. (Copy not submitted herewith pursuant to the waiver of 37 C.F.R. § 1.98(a)(2)(iii) issued by the Office on Sep. 21, 2004.).
U.S. Appl. No. 17/000,007, filed Aug. 21, 2020, by Godfrin et al. (Copy not submitted herewith pursuant to the waiver of 37 C.F.R. § 1.98(a)(2)(iii) issued by the Office on Sep. 21, 2004.).
U.S. Appl. No. 17/075,116, filed Oct. 20, 2020, by Sharei et al. (Copy not submitted herewith pursuant) to the waiver of 37 C.F.R. § 1.98(a)(2)(iii) issued by the Office on Sep. 21, 2004.).
U.S. Appl. No. 17/169,357, filed Feb. 5, 2021, by Godfrini et al. (Copy not submitted herewith pursuant to the waiver of 37 C.F.R. § 1.98(a)(2)(iii) issued by the Office on Sep. 21, 2004.).
Van Schooten, W.C. et al. (Jun. 1997, e-pub. Feb. 4, 1998). "Biological Properties of Dendritic Cells: Implications to Their Use in the Treatment of Cancer", Molecular Medicine Today 3(6):254-260.
Wood, K.J. et al. (Jan. 1, 1985). "Antigen-Induced Suppression: The Role Of Class I Major Histocompatibility Antigens," Bioscience Reports 5(10-11):1007-1014.
You, Q. et al. (May 2, 2008). "Mechanism of T Cell Tolerance Induction by Murine Hepatic Kuoffer Cells," Hepatology 48(3):978-990.
Zarnitsyn, V.G. et al. (2008, e-pub. Nov. 10, 2007). "Electrosonic Ejector Microarray For Drug And Gene Delivery," Biomed Microdevices 10:299-308.
Esposito, F. et al. (Dec. 1, 1990). "Intraerythrocytic Administration of a Synthetic Plasmodium Antigen Elicits Antibody Response in Mice, Without Carrier Molecules or Adjuvants", International Journal Of Parasitology 20(8):1109-1111.
Grimm, A.J. et al. (2015, e-pub. Oct. 29, 2015). "Memory of Tolerance and Induction of Regulatory T Cells by Erythrocyte-Targeted Antigens," Sci Rep. 5:15907, 11 pages.
Hamidi, M. et al. (Apr. 2, 2007, e-pub. Dec. 15, 2006). "Applications of Carrier Erythrocytes in Delivery of Biopharmaceuticals," J. Control. Release, 2007, 118(2): 145-160.
International Preliminary Report on Patentability mailed Nov. 15, 2018, for Patent Application No. PCT/US2017/030933, filed May 3, 2017, 13 pages.
International Preliminary Report on Patentability mailed Nov. 6, 2018, for Patent Application No. PCT/US2017/030932, filed May 3, 2017, 9 pages.
International Search Report mailed Jul. 21, 2017, for International Patent Application No. PCT/2017030933 filed May 3, 2017, 4 pages.
International Search Report mailed Sep. 19, 2017, for Patent Application No. PCT/US2017/030932, filed May 3, 2017, 6 pages.
Kontos, S. et al. (Jan. 2, 2013, e-pub. Dec. 17, 2012). "Engineering antigens for in Situ Erythrocyte Binding Induces T-cell Deletion," PNAS USA. 110(1):E60-E68.
Lorentz et al. (Jul. 2015, e-pub. Jul. 17, 2015). "Engineered Binding to Erythrocytes Induces Immunological Tolerance to *E. Coli* Asparaginase," Sci. Adv. 1(6):e1500112, 10 pages.
Polvani, C. et al. (Dec. 1, 1991). "Murine Red Blood Cells As Efficient Carriers Of Three Bacterial Antigens For The Production Of Specific And Neutralizing Antibodies", Biotechnology And Applied Biochemistry 14:347-356.
Ravilla, S. et al. (Apr. 28, 2012). : "Erythrocytes as Carrier for Drugs, Enzymes and Peptides", Journal Of Applied Pharmaceutical Science 2(4):166-176.

(56) References Cited

OTHER PUBLICATIONS

Rutella, S. et al. (Sep. 1, 2006). "Tolerogenic Dendritic Cells: Cytokine Modulation Comes of Age", Blood 180(5):1435-1440.
Sharei, A. et al. (Apr. 13, 2015). "Ex Vivo Cytosolic Delivery of Functional Macromolecules to Immune Cells," PLOS ONE 10(4):e0118803, 12 pages.
Steinman, R.M. et al. (Apr. 1, 2003). "Tolerogenic Dendritic Cells", Annu. Rev. Immunol. 21:685-711.
Stewart, M.P. et al. (Oct. 12, 2016). "In Vitro and Ex Vitro Strategies for Intracellular Delivery", Nature 538(7624):183-192.
Written Opinion of the International Searching Authority mailed Jul. 21, 2017, for Patent Application No. PCT/US2017/030933, filed May 3, 2017, 11 pages.
Written Opinion of the International Searching Authority mailed Sep. 19, 2017, for PCT Patent Application No. PCT/US2017/030932, filed May 3, 2017, 8 pages.
Adriaenssens, K. et al. (1984). "Hyperargininemia: The Rat As A Model For The Human Disease And The Comparative Response To Enzyme Replacement Therapy With Free Arginase And Arginase-Loaded Erythrocytes In Vivo," Int J Biochem. 16(7):779-786.
Albina, J.E. et al. (Apr. 1, 1988). "Arginine Metabolism in Wounds", The American Physiological Society 254(4):E459-E467. (located at https://journals.physiology.org/doi/pdf/10.1152/ajpendo.1988.254.4.e459, last visited on Aug. 20, 2020).
American Type Culture Collection (ATCC) (Feb. 27, 2012). "Thawing, Propagating, and Cryopreserving Protocol," Version 1.6, Physical Sciences—Oncology Center Network Bioresource Core Facility, 26 pages.
Antonelou, M. H. et al. (Jun. 2010). "Aging And Death Signalling In Mature Red Cells: From Basic Science To Transfusion Practice," Blood Trans Fus. 8(Suppl 3):s39-s47.
Ash, David E. (Oct. 2004). "Structure and Function of Arginases", The Journal of Nutrition 134(10):2760S-2764S.
Bailleul, C. et al. (1991). "Internalization of Various Allosteric Effectors of Hemoglobin in Human Erythrocytes", Advances in the Biosciences 81:9-16.
Banchereau, J. et al. (Aug. 10, 2001). "Dendritic Cells as Vectors for Therapy", Cell 106(3):271-274.
Banz, et al. (Aug. 4, 2003). "A Unique Subpopulation of CD4+ Regulatory T Cells Controls Wasting Disease, IL-1 O Secretion and T Cell Homeostasis", Eur. J. Immunol. 33(9):2419-2428.
Bax, B.E. et al. (Feb. 1, 1999). "Survival of Human Carrier Erythrocytes In Vivo", Clinical Science 96(2):171-178.
Bigbee, W.L. et al. (Dec. 1983). "Monoclonal Antibodies Specific for the M- and N-Forms of Human Glycophorin A*," Molecular Immunology 20(12):1353-1362.
Boberg, A. et al. (Apr. 18, 2007). "Immunization with HIV Protease Peptides Linked to Syngeneic Erythrocytes", Infectious Agents and Cancer 2(9):1-4.
Bomalaski, J.S. et al. (2003). "Comparative Toxicity of Arginine Deiminase Formulated with Poly(Ethylene Glycol) 5000 or 20,000 and the Effects of Arginine," PreClinica 1(5):284-293.
Bonifaz, L. et al. (Dec. 16, 2002). "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", J. Exp. Med. 196(12):1627-1638.
Boucher, L. et al. (Aug. 1996). "Internalization and Distribution of Inositol Hexakisphosphate in Red Blood Cells", Biotechnology and Applied Biochemistry 24(1):73-78.
Breous, E. et al. (Jul. 29, 2009). "Hepatic Regulatory T Cells and Kupffer Cells are Crucial Mediators of Systemic T Cell Tolerance to Antigens Targeting Murine Liver", Hepatoloqy 50(2):612-620.
Chen, Xian-Zhen et al. (2010, e-pub. Jul. 4, 2009). "Toll Like Receptor Agonists Augment HPV 11 E7-Specific T Cell Responses By Modulating Monocyte-Derived Dendritic Cells," Arch Dermatol Res. 302(1):57-65.
Cremel et al. (Aug. 1, 2015, e-pub. Jun. 6, 2015). "Innovative Approach In Pompe Disease Therapy: Induction Of Immune Tolerance By Antigen-Encapsulated Red Blood Cells," Int J Pharm. 491(1-2):69-77.
Cremel et al. (Feb. 25, 2013, e-pub. Jan. 7, 2013). "Red Blood Cells as Innovative Antigen Carrier to Induce Specific Immune Tolerance," Int J Pharm.443(1-2):39-49.
Curley, S.A. et al. (Aug. 31, 2003). "Regression of Hepatocellular Cancer in a Patient Treated With Arginine Deiminase," Hepatogastroenterology 50(53):1214-1216, 1 page. (Abstract Only).
De Jong, K. et al. (1997). "Oxidative Damage Does Not Alter Membrane Phospholipid Asymmetry in Human Erythrocytes," Biochemistry 36:6768-6776.
Debellis, R.H. et al. (2003). "Inhibition Of Sickling In Vitro By Three Purine-Based Antiviral Agents: An Approach To The Treatment Of Sickle Cell Disease," Blood Cells Mol. Dis. 31:286-290.
Delaby, C. et al. (2005, e-pub. Aug. 10, 2005). "A Physiological Model To Study Iron Recycling In Macrophages," Exp. Cell Res. 310(1):43-53.
Deleuze, P.H. et al. (Apr. 1, 1992). "Enhanced O2 Transportation During Cardiopulmonary Bypass In Piglets By The Use Of Inositol Hexaphoshate Loaded Red Blood Cells," The International Journal of Artificial Organs 15(4):239-242.
Didelon, J. et al. (2000). "Osmotic Fragility Of The Erythrocyte Membrane: Characterization By Modeling Of The Transmittance Curve As A Function Of The NaCl Concentration," Biorheology 37(5-6):409-416.
Didelon, J. et al. (2000). "Validation Of A Test Of The Red Cell Membrane Osmotic Resistance," Clinical Hemorheology And Microcirculation 23(1):31-42.
Dillon, B.J. et al. (2002, e-pub. Jul. 15, 2000). "Biochemical Characterization Of The Arginine Degrading Enzymes Arginase And Arginine Deiminase And Their Effect On Nitric Oxide Production," Med. Sci. Monit. 8(7):BR248-BR253.
Ditommaso, T. et al. (Nov. 13, 2018, e-pub. Oct. 31, 2018). "Cell Engineering with Microfluidic Squeezing Preserves Functionality of Primary Immune Cells in Vivo," PNAS 115(46):E10907-E10914, 8 pages.
Dominici, S. et al. (May 16, 2003). "Red Blood Cell-Mediated Delivery of Recombinant HIV-1 Tat Protein in Mice Induces Anti-Tat Neutralizing Antibodies and CTL," Vaccine 21(17-18): 2073-2081.
Ensor, C. M. et al. (Oct. 2002). "Pegylated Arginine Deiminase (ADI-SS PEG20,000 mw) Inhibits Human Melanomas and Hepatocellular Carcinoma in Vitro and in Vivo," Cancer Research 62(19):5443-5450.
Eymard, J.C. et al. (2003). "Cell Therapy and Prostate Cancer", Dossier Thematique 90(8-9):734-743. English Abstract.
Gong, H. et al. (Apr. 28, 2000). "Arginine Deiminase Inhibits Proliferation Of Human Leukemia Cells More Potently Than Asparaginase By Inducing Cell Cycle Arrest And Apoptosis," Leukemia 14:826-829.
Gong, H. et al. (Sep. 20, 2003, e-pub. Jun. 18, 2003). "Arginine Deiminase And Other Antiangiogenic Agents Inhibit Unfavorable Neuroblastoma Growth: Potentiation By Irradiation," Int. J Cancer. 106(5):723-728.
Greenhalkh, T. (2004). "Basics of Evidence-Based Medicine," Geotarmed 240:52-69, 22 pages. With English Translation.
Hamidi, M. et al. (2003, e-pub. Sep. 29, 2008). "Carrier Erythrocytes: An Overview," Drug Delivery 10(9):9-20.
Hervas-Stubbs, S. et al. (Jun. 15, 2007, e-pub. Mar. 5, 2007). "TLR3 ligand stimulates fully functional memory-CD8+T cells in the absence of CD4+ T-cell help," Immunobiology 109(12):5318-5326.
Holtsberg, F.W. et al. (Apr. 23, 2002). "Poly(ethylene glycol) (PEG) Conjugated Arginine Deiminase: Effects Of PEG Formulations On Its Pharmacological Properties," Journal of Controlled 80(1-3):259-271.
Hussain, A.A. et al. (Aug. 1984). "Erythrocyte Osmotic Fragility in Man: Variation with Age and Sex," Br. J. Haematol. 57(4):716-718.
Ing, R. et al. (2006). "Interaction-of Mouse Dendritic Cells and Malaria-Infected Erythrocytes: Uptake, Maturation, and Antigen Presentation," J Immunol 176:441-450.

(56) References Cited

OTHER PUBLICATIONS

Izzo, F. et al. (May 15, 2004). "Pegylated Arginine Deiminase Treatment of Patients With Unresectable Hepatocellular Carcinoma: Results From Phase 1/11 Studies," Journal Of Clinical Oncology 22(10):1815-1822.
Jadhav, K.R. et al. (Jan.-Feb. 2012). "Drug, Enzyme and Peptide Delivery Using Erythrocytes as Drug Carrier," International Journal Of Pharmaceutical Sciences Review and Research 12(1):79-88.
Ju, C. et al. (Dec. 1, 2003, e-pub. Nov. 8, 2003). "Tolerogenic Role of Kupffer Cells in Allergic Reactions", Chem. Res. Toxicol. 16(12):1514-1519.
Kamei, T. et al. (May 1990, e-pub. Feb. 9, 2004). "Kupffer Cell Blockade Prevents Induction of Portal Venous Tolerance in Rat Cardiac Allograft Transplantation," Journal Of Surgical Research 48(5):393-396.
Kenter, G. G. et al. (Nov. 5, 2009). "Vaccination against HPV-16 Oncoproteins for Vulvar Intraepithelial Neoplasia," The New England Journal Of Medicine 361(19):1838-1847, 14 pages. (Including Supplemental Material).
Kolanjiappan, K. et al. (Dec. 2002, e-pub. Oct. 28, 2002). "Measurement Of Erythrocyte Lipids, Lipid Peroxidation, Antioxidants And Osmotic Fragility In Cervical Cancer Patients," Clinica Chimic Acta 326(1-2):143-149.
Kollmannsperger, A. et al. (Jan. 29, 2016). "Live-Cell Protein Labelling With Nanometre Precision By Cell Squeezing," Nat Comm 7(10372):1-7.
Kravtzoff, R. et al. (Jul. 1990). "Erythrocytes As Carriers For L-Asparaginase Methodological And Mouse In-Vivo Studies," The Journal Of Pharmacy And Pharmacology 42(7):473-476.
Labrude, P. et al. (1985). "L'Hematie Vecteur D'Enzyme et de Medicament (Red blood cell as enzyme- and drug-carrier (en))," Lyon Pharmaceutique 36(4):181-187.
Lange, P.S. et al. (Oct. 2004). "Novel Roles for Arginase in Cell Survival, Regeneration, and Translation in the Central Nervous System," The Journal of Nutrition (Arginase In The Central Nervous System) 134(10):2812S-2817S.
Lau, A.H. et al. (2003, e-pub. Jul. 15, 2003). "Liver Tolerance Mediated By Antigen Presenting Cells: Fact Or Fiction?," Gut 52(8):1075-1078.
Li, J. et al. (Jun. 30, 2016, e-pub. May 19, 2016). "The Combination Of Pleurotus Ferulaewater Extract And CpG-ODN Enhances The Immune Responses And Antitumor Efficacy Of HPV Peptides Pulsed Dendritic Cell-Based Vaccine," Vaccine 34(31):3568-3575.
Limmer, A. et al. (Dec. 2000). "Efficient Presentation of Exogenous Antigen By Liver Endothelial Cells to CD8+ T Cells Results in Antigen-Specific T-Cell Tolerance", Nature Medicine 6(12):1348-1354.
Lind, D. S. (2004). "Arginine Metabolism: Enzymology, Nutrition, and Clinical Significance: Arginine and Cancer," J. Nutr. 134:2837S-2841S.
Lou, Y. et al. (Feb. 1, 2007). "Plasmacytoid Dendritic Cells Synergize with Myeloid Dendritic Cells in the Induction of Antigen-Specific Antitumor Immune Responses," The Journal of Immunology 178(3):1534-1541.
Loughhead, S.M. et al. (Dec. 1, 2018). "SQZing Cells To Rapidly Generate Antigen Presenting Cells (APC) For Solid Tumor Immune Therapies With Efficient, Scalable Manufacturing," Abstract, Annals Of Oncology 29(Suppl No. 10):1 page, (Abstract No. 38P).
Magnani, M. et al. (1998). "Erythrocyte Engineering for Drug Delivery and Targeting," Biotechnology and Applied Biochemistry 28(1):1-6.
Mahnke, K. et al. (Jun. 15, 2003). "Induction of CD4+/CD25+ Regulatory T Cells By Targeting Of Antigens To Immature Dendritic Cells," Blood 101(12):4862-4869.
Marx, V. (Jan. 2016, e-pub. Dec. 30, 2015). "Cell Biology: Delivering Tough Cargo into Cells," Nature Methods 13(1):37-40.
McCarthy, D. (Oct. 2018). "Engineering Erythrocytes for Immune Tolerance via CellSqueeze® Technology," Poster, presented at the Immunology of Diabetes Society Congress, London, UK, Oct. 25-29, 2018, 1 page.
Miao, C. H. et al. (Nov. 5, 2009, e-pub. Aug. 27, 2009). "CD4+ FOXP3+ Regulatory T Cells Confer Long-Term Regulation Of Factor VI II-Specific Immune Responses In Plasmid-Mediated Gene Therapy-Treated Hemophilia Mice," Blood 114(19):4034-4044.
Milo, R. et al. (Sep. 20, 2013). "What Is The Total Number Of Protein Molecules Per Cell Volume? A Call To Rethink Some Published Values," Bioessays 35(12):1050-1055.
Mori, M. et al. (Oct. 2004). "Arginine Metabolic Enzymes, Nitric Oxide and Infection," The Journal of Nutrition 134(10):2820S-2825S.
Moser, B. et al. (Jul. 2011, e-pub. May 15, 2011). "gamma delta T-APCs: A Novel Tool For Immunotherapy?," Cellular And Molecular Life Sciences 68(14):2443-2452.
Murray, A. M. et al. (Aug. 28, 2006, e-pub. May 23, 2006). "The Mouse Immune Response To Carrier Erythrocyte Entrapped Antigens," Vaccine 24(35-36):6129-6139.
Papaioannou, N.E. et al. (2016). "Harnessing the Immune System to Improve Cancer Therapy," Annals of Translational Medicine 4(14):261, 15 pages.
Park, I.S. et al. (Sep. 1, 2003, e-pub. Aug. 26, 2003). "Arginine Deiminase: A Potential Inhibitor Of Angiogenesis And Tumour Growth," Br J. Cancer 89(5):907-914.
Patel, K.K. et al. (Dec. 1, 2016). "Combination Immunotherapy with NY-ESO-1-Specific CAR+ T Cells with T-Cell Vaccine Improves Anti-Myeloma Effect," Blood Journal 128(22):3366, 1 page (Poster).
Pozzi, L.-A.M et al. (2005). "Both Dendritic Cells and Macrophages Can Stimulate Naïve CD8 T Cells in vivo to Proliferate, Develop Effector Function, and Differentiate Into Memory Cells," J. Immunol. 175(4):2071-2081.
Regnault, A. et al. (Jan. 18, 1999). "Fcy Receptor-Mediated Induction of Dendritic Cell Maturation and Major Histocompatibility Complex Class I-restricted Antigen Presentation after Immune Complex Internalization," J. Exp. Med. 189(2):371-380.
Romero, P.J. et al. (Feb. 1999, e-pub. Jan. 15, 1999). "The Role of Calcium Metabolism in Human Red Blood Cell Aging: A Proposal," Blood Cells Mol Dis. 25(1):9-19.
Ropars, C. et al. (Jul. 1998). "Engineered Erythrocytes: Influence Of P50 Rightward Shift And Oxemia On Oxygen Transport To Tissues," Med. Biol. Eng. Comp. 36:508-512.
Sadahiro, S. et al. (Aug. 2003). "Pharmacokinetics of 5-Fluorouracil Following Hepatic Intra-arterial Infusion in a VX2 Hepatic Metastasis Model," Japanese J. Clin Oncol. 33(8):377-381.
Saung, M. (Nov. 2016). "A Size-Selective Intracellular Delivery Platform," Small 12(42):5873-5881, 17pages.
Schrijvers, D. et al. (Aug. 2003, Sep. 13, 2003). "Role of Red Blood Cells in Pharmacokinetics of Chemotherapeutic Agents," Clin. Pharmacokinet 42(9):779-791.
Seeman, P. (Jan. 1, 1967). "Transient Holes in the Erythrocyte Membrane During Hypotonic Hemolysis and Stable Holes in the Membrane After Lysis by Saponin and Lysolecithin," Journal of Cell Biology 32(1):55-70.
Sercombe, L. et al. (2015, e-pub. Dec. 1, 2015). "Advances and Challenges of Liposome Assisted Drug Delivery," Front Pharmacol. 6:286, 13 pages.
Sharei, A. et al. (Apr. 1, 2014, e-pub. Jan. 27, 2014). "Plasma Membrane Recovery Kinetics of a Microfluidic Intracellular Delivery Platform," Integrative Biology 6(4):470-475.
Sharei, A.R. (Jun. 26, 2013). "Cell Squeezing: A Vector-Free Microfluidic Platform for Intracellular Delivery of Macromolecules," MIT Thesis (Public, located here: https://dspace.mit.edu/bitstream/handle/1721.1/81688/860804208-MIT.pdf?sequence=2) 165 pages.
Spector, E.B. et al. (Nov. 1985). "Comparison or Arginase Activity in Red Blood Cells of Lower Mammals, Primates, and Man: Evolution to High Activity in Primates," Am. J. Hum. Genet. 37(6):1138-1145.
Stewart, M. et al. (Aug. 22, 2018, e-pub. Jul. 27, 2018). "Intracellular Delivery by Membrane Disruption: Mechanisms, Strategies, and Concepts," Chem. Rev. 118(16):7409-7531.
Stuehr, D.J. (Oct. 2004). "Enzymes of the L-Arginine to Nitric Oxide Pathway," The Journal of Nutritional 134(10):2748S-2751S.

(56) References Cited

OTHER PUBLICATIONS

Suresh, T. et al. (2017). "The Emerging Role of Immunotherapy in Head and Neck Squamous Cell Cancer," in The American Journal of Hematology/Oncology 13(6):20-27, 8 pages.
Talarico, L. et al. (Nov. 2017). "Engineered Antigen Presenting T Cells for the Treatment of Solid Tumor Cancers," EMBASE, 32nd Annual Meeting and Pre-Conference Programs of the Society for Immunotherapy of Cancer, SITC 2017, Journal for ImmunoTherapy of Cancer 5(Suppl. 2):EMB-619371158, 1 page. (Abstract).
Tanchot, C. et al. (2004). "Immune Regulation by Self-Reactive T Cells is Antigen Specific," The Journal of Immuno 172:4285-4291.
Thomas, J. B. et al. (Apr. 24, 2002). "Enzymic Degradation Of Plasma Arginine Using Arginine Deiminase Inhibits Nitric Oxide Production And Protects Mice From The Lethal Effects Of Tumour Necrosis Factor And Endotoxin," Biochem J. 363(3):581-587.
Thornton, A.M. et al. (2000). "Suppressor Effector Function of CD4+ CD25+ Immunoregulatory T Cells Is Antigen Nonspecific," Journal of Immunology, 164:183-190.
Tran, D.Q. et al. (May 2009, e-pub. Feb. 21, 2009). "Therapeutic Potential of FOXP3+ Regulatory T Cells And Their interactions with dendritic cells," Human Immunology 70(5):294-299.
Tsaoir, C. et al. (Jun. 2016). "Scalable Antibody Production from CHO Cell Line of Choice Using Flow Electroporation," Poster, Cell Line Development Jun. 2016, © 2016 MaxCyte, Inc., located at: https://www.maxcyte.com/wp-content/uploads/2017/10/scalable-ab-production-from-cho-cells.pdf, last retrieved on Apr. 2, 2019, 1 page. (Poster).
Tu, C. et al. (May 16, 2016, e-pub. Mar. 9, 2016). "Monitoring Protein Synthesis in Single Live Cancer Cells," Integr Biol (Camb) 8(5):645-653.
Van Broeckhoven, C.L. et al. (Dec. 23, 1982). "Measurement of Arginine Transport in Human Erythrocytes Using Their Intrinsic Arginase Activity: Implications for the Treatment of Familial Hyperargininemia," Clinica Chimica Acta 126(3):209-216.
Vellard, M. (Aug. 2003, e-pub. Jun. 24, 2003). "The Enzyme As Drug: Application Of Enzymes As Pharmaceuticals," Current Opinion in Biotechnology 14(4):1-7.
Villa, C. et al. (Dec. 2016, e-pub. Oct. 31, 2016). "Drug Delivery By Erythrocytes: "Primum Non Nocere"," Transfusion And Apheresis Science 55(3):275-280, 12 pages.
Vorobyev, A.A. et al. (2003). "Medicine," Microbiology pp. 158-159, 6 pages. With English Translation.
Votano, J.R. et al. (Jun. 10, 1977). "Sickle Hemoglobin Aggregation: A New Class Of Inhibitors," Science 196(4295):1216-1219.
Wang, B. et al. (Aug. 1, 2003, e-pub. Jul. 29, 2003). "Evaluation of Immunologic Crossreaction of Antiasparaginase Antibodies in Acute Lymphoblastic Leukemia (ALL) and Lymphoma Patients," Leukemia 17:1583-1588.
Wei-Chiang, S. (2000). "Research Page: Arginine Deiminase as an Innovative Anti-Breast Cancer Agent," Initial Award Abstract (2pgs.), Research Priorities, Innovative Treatment Modalities New Drug Design: Creative Science, University of Southern California, 2 pages. (Abstract Only).
Wieneke, R. (Feb. 2019). "Selektive Proteinmarkierung Mit Nanometerpräzision in Lebenden Zellen," BIOspektrum 25(1):37-40.
Williamson, P. et al. (1992). "Ca2+ Induces Transbilayer Redistribution of All Major Phospholipids in Human Erythrocytes," Biochemistry 31:6355-6360.
Yang, Y.G. et al. (Nov. 4, 2015). "Carrier Erythrocytes And Its Application In Targeting Chemotherapy," Journal of Medical Postgraduates 17(11):1015-1018. (English Abstract Only).
Zocchi, E. et al. (Mar. 1989). "Encapsulation Of Doxorubicin In Liver-Targeted Erythrocytes Increases The Therapeutic Index Of The Drug In A Murine Metastatic Model," PNAS USA 86:2040-2044.

* cited by examiner

SQZ – 2 psi

SQZ – 4 psi

SQZ – 6 psi

Geometric Mean FL
14000
12000
10000
8000
6000
4000
2000
0
NC
SQZ no material 2psi
Endo
2 psi
4 psi
6 psi
10 psi
20 psi
Fast manual push
Dextran
IgG Delivery (%)
100
90
80
70
60
50
40
30
20
10
0
NC
SQZ no material 2psi
Endo
2 psi
4 psi
6 psi
10 psi
20 psi
Fast manual push
Dextran
IgG

INTRACELLULAR DELIVERY OF BIOMOLECULES TO INDUCE TOLERANCE

CROSS-REFERENCE TO RELATED APPLICATIONS

This application is a National Phase filing under 35 U.S.C. § 371 of International Application No. PCT/US2017/030932 having an International Filing Date of May 3, 2017, which claims priority to U.S. Provisional Application No. 62/331,368, filed on May 3, 2016, which are hereby incorporated by reference in their entirety.

FIELD OF THE INVENTION

The present disclosure relates generally to methods for suppressing an immune response or inducing tolerance by delivering a compound into a cell by passing a cell suspension through a cell-deforming constriction.

BACKGROUND

The presence of antigens in the non-inflammatory and apoptotic environment of the spleen has been shown to induce anergy and tolerance. One way to ensure the consistent presentation of the antigen of interest in this tolerogenic environment is via physical interaction with a red blood cell (RBC).

However, manipulation of red blood cells to associate antigenic material is challenging given that they are irregularly shaped (biconcave), anucleate, and transcriptionally inactive. As a result, standard transfection techniques do not work and therefore initial proof of the tolerogenic potential of red blood cell has focused on conjugating materials to the surface of erythrocytes (Lorentz et al. Sci. Adv. 2015, 1:e1500112; Grimm et al. Sci Rep. 2015 Oct. 29, 5:15907; Kontos et al. Proc Natl Acad Sci USA. 2013 Jan. 2, 110(1):E60-8). Initial work using surface conjugation has shown promising results with model antigens and mouse models of Type 1 diabetes but has some significant drawbacks. These drawbacks include: a) the need for chemically modified antigens for attachment b) limited surface area of loading c) immunogenicity.

Thus, there is an unmet need for intracellular delivery techniques that can load antigen into the cytoplasm of red blood cells and drive a powerful immunosuppressive response for the treatment of pathogenic immune responses underlying autoimmune diseases and transplant rejection. References that describe methods of using microfluidic constrictions to deliver compounds to cells include WO2013059343, WO2015023982, WO2016070136. WO2016077761, and PCT/US2016/13113.

All references cited herein, including patent applications and publications, are incorporated by reference in their entirety.

BRIEF SUMMARY OF THE INVENTION

The present invention provides a method for suppressing an immune response in an individual, the method comprising passing a cell suspension comprising an anucleate cell through a constriction, wherein said constriction deforms the cell thereby causing a perturbation of the cell such that an antigen enters the anucleate cell, and introducing the anucleate cell into the individual, wherein said antigen is processed in a tolerogenic environment, wherein presentation of said antigen in said tolerogenic environment suppresses an immune response to the antigen.

Certain aspects of the present invention provide a method for suppressing an immune response in an individual, the method comprising passing a cell suspension comprising an anucleate cell through a constriction, wherein said constriction deforms the cell thereby causing a perturbation of the cell such that one or more tolerogenic factors enter the anucleate cell, and introducing the anucleate cell into the individual, wherein action of said one or more tolerogenic factors contributes to a tolerogenic environment and suppression of an immune response.

Certain aspects of the present invention provide a method for suppressing an immune response in an individual, the method comprising passing a cell suspension comprising an anucleate cell through a constriction, wherein said constriction deforms the cell thereby causing a perturbation of the cell such that an antigen and one or more tolerogenic factors enter the anucleate cell, and introducing the anucleate cell into the individual, wherein processing of said antigen in a tolerogenic environment suppresses an immune response.

Certain aspects of the present invention provide a method for suppressing an immune response in an individual, comprising passing a first cell suspension comprising a first anucleate cell through a constriction, wherein said constriction deforms the cell thereby causing a perturbation of the cell such that an antigen enters the anucleate cell, passing a second cell suspension comprising a second anucleate cell through a constriction, wherein said constriction deforms the cell thereby causing a perturbation of the cell such that a tolerogenic factor enters the anucleate cell, introducing the first anucleate cell and second anucleate cell into the individual, wherein said antigen is processed in a tolerogenic environment, wherein presentation of said antigen in said tolerogenic environment suppresses an immune response to the antigen.

Certain aspects of the present invention provide a method for suppressing an immune response in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment, wherein presentation of said antigen in said tolerogenic environment suppresses an immune response to the antigen.

Certain aspects of the present invention provide a method for delivering a tolerogenic factor into an anucleate cell, the method comprising passing a cell suspension comprising the anucleate cell through a constriction, wherein said constriction deforms the anucleate cell, thereby causing a perturbation of the cell such that the tolerogenic factor enters the cell, wherein said cell suspension is contacted with the tolerogenic factor.

Certain aspects of the present invention provide a method for introducing an antigen into a tolerogenic environment comprising delivering an anucleate cell into an individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment.

Certain aspects of the present invention provide a method for inducing tolerance to an antigen in an individual, the method comprising passing a cell suspension comprising an anucleate cell through a constriction, wherein said constriction deforms the cell thereby causing a perturbation of the cell such that an antigen enters the anucleate cell, introducing the anucleate cell into the individual, wherein said antigen is processed in a tolerogenic environment, wherein presentation of said antigen in said tolerogenic environment induces tolerance to the antigen.

Certain aspects of the present invention provide a method for inducing tolerance in an individual, the method comprising passing a cell suspension comprising an anucleate cell through a constriction, wherein said constriction deforms the cell thereby causing a perturbation of the cell such that a tolerogenic factor enters the anucleate cell, and introducing the anucleate cell into the individual, wherein action of said tolerogenic factor contributes to a tolerogenic environment that induces tolerance.

Certain aspects of the present invention provide a method for inducing tolerance to an antigen in an individual, comprising passing a first cell suspension comprising a first anucleate cell through a constriction, wherein said constriction deforms the cell thereby causing a perturbation of the cell such that an antigen enters the anucleate cell, passing a second cell suspension comprising a second anucleate cell through a constriction, wherein said constriction deforms the cell thereby causing a perturbation of the cell such that a tolerogenic factor enters the anucleate cell, introducing the first anucleate cell and second anucleate cell into the individual, wherein said antigen is processed in a tolerogenic environment, wherein presentation of said antigen in said tolerogenic environment induces tolerance to the antigen.

Certain aspects of the present invention provide a method for inducing tolerance to an antigen in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment, wherein presentation of said antigen in said tolerogenic environment induces tolerance to the antigen.

Certain aspects of the present invention provide a method for delivering an antigen into an anucleate cell, the method comprising passing a cell suspension comprising the anucleate cell through a constriction, wherein said constriction deforms the anucleate cell, thereby causing a perturbation of the cell such that the antigen enters the cell, wherein said cell suspension is contacted with the antigen. In some embodiments, processing and presentation of said antigen in a tolerogenic environment suppresses an immune response to the antigen. In some embodiments, processing and presentation of said antigen in a tolerogenic environment induces tolerance to the antigen. In some embodiments that can be combined with the previous embodiments, the tolerogenic environment is located in the spleen, liver, or lymph nodes.

In some embodiments, the constriction is contained within a microfluidic channel. In some embodiments, the channel comprises a constriction width of about 0.25 μm to about 4 μm. In some embodiments, the channel comprises a constriction width of about 4 μm, about 3.5 μm, about 3 μm, about 2.5 μm, about 2 μm, about 1 μm, about 0.5 μm, or about 0.25 μm. In some embodiments, the constriction is a pore or contained within a pore. In some embodiments, the pore is contained in a surface. In some embodiments, the surface is a filter. In some embodiments, the surface is a membrane. In some embodiments, the pore size is about 0.5 μm to about 4 μm. In some embodiments, the pore size is 4 μm, about 3 μm, about 2 μm, about 1 μm, or about 0.5 μm. In some embodiments, the constriction size is a function of the diameter of the anucleate cell. In some embodiments, the constriction size is about 10%, about 20%, about 30%, about 40%, about 50%, about 60%, or about 70% of the cell diameter. In some embodiments, the method is performed between about −5° C. and about 45° C.

Reference to a diameter of an anucleate cell means the diameter of the cell in fluid prior to being passed through a constriction, e.g., as the cell approaches the constriction, unless otherwise specified.

In some embodiments that can be combined with the previous embodiments, the cell suspension comprises a mixed cell population. In some embodiments, the cell suspension is whole blood. In some embodiments, the cell suspension comprises a purified cell population. In some embodiments, the cell suspension comprises a purified anucleate cell population. In some embodiments, the cell suspension comprises mammalian cells. In some embodiments, the cell suspension comprises monkey, mouse, dog, cat, horse, rat, sheep, goat, pig, or rabbit cells. In some embodiments, the cell suspension comprises human cells. In some embodiments, the anucleate cell is a red blood cell. In some embodiments, the red blood cell is an erythrocyte. In some embodiments, the red blood cell is a reticulocyte. In some embodiments, the anucleate cell is a platelet.

In some embodiments that can be combined with the previous embodiments, the antigen is located in a cell lysate. In some embodiments, the antigen is a foreign antigen. In some embodiments, the antigen is a self-antigen. In some embodiments, the antigen is an allograft transplantation antigen. In some embodiments, the antigen is a microorganism. In some embodiments, the antigen is a lipid antigen. In some embodiments, the antigen is a carbohydrate antigen (e.g., a sugar). In some embodiments, the antigen is a modified antigen. In some embodiments, the modified antigen comprises an antigen fused with a polypeptide. In some embodiments, the modified antigen comprises an antigen fused with a therapeutic agent. In some embodiments, the modified antigen comprises an antigen fused with a targeting peptide. In some embodiments, the modified antigen comprises an antigen fused with a lipid. In some embodiments, the modified antigen comprises an antigen fused with a carbohydrate (e.g., a sugar). In some embodiments, the antigen is an antigen associated with transplanted tissue. In some embodiments, the antigen is associated with a virus. In some embodiments, said cell suspension is contacted with the antigen before, concurrently, or after passing through the constriction.

In some embodiments that can be combined with the previous embodiments, the tolerogenic factor comprises a polypeptide. In some embodiments, the polypeptide is IL-4, IL-10, IL-13. IL-35. IFNα, or TGFβ. In some embodiments, the polypeptide is a therapeutic polypeptide. In some embodiments, the polypeptide is a fragment of a therapeutic polypeptide. In some embodiments, the polypeptide is a therapeutic peptide. In some embodiments, the polypeptide is conjugated to a carbohydrate (e.g., a sugar). In some embodiments, said cell suspension is contacted with the tolerogenic factor before, concurrently, or after passing through the constriction. In some embodiments, the half-life of the anucleate cell is decreased. In some embodiments, the half-life of the anucleate cell is increased.

In embodiments where an immune response is suppressed, the immune response is suppressed by at least about 25%, about 50%, about 75%, about 100%, about 150%, about 200%, or more than about 200%. In some embodiments, the suppressed immune response comprises a decreased T cell response. In some embodiments, the decreased T cell response comprises decreased T cell activation. In some embodiments, the decreased T cell response comprises decreased T cell survival. In some embodiments, the decreased T cell response comprises decreased T cell proliferation. In some embodiments, the decreased T cell response comprises decreased T cell functionality. In some embodiments, the decreased T cell response comprises a change in T cell phenotype. In some embodiments, the suppressed immune response comprises uncostimulated activation of a T cell. In some embodiments, the suppressed immune response comprises an enhanced Treg response. In some embodiments, the suppressed immune response comprises a decreased B cell response. In some embodiments, the decreased B cell response comprises decreased antibody production. In some embodiments, the suppressed immune response comprises decreased cytokine production. In some embodiments, the suppressed immune response comprises a decreased autoimmune response. In some embodiments, the suppressed immune response comprises a decreased allergic response. In some embodiments, the suppressed immune response comprises a decreased immune response against the transplanted tissue. In some embodiments, the suppressed immune response comprises a decreased pathogenic immune response to the virus. In some embodiments, the suppressed immune response comprises a decreased immune response against a therapeutic agent. In some embodiments, the suppressed immune response comprises a decreased immune response against a therapeutic vehicle.

In embodiments where tolerance is induced, the tolerance may comprise a decreased T cell response. In some embodiments, the decreased T cell response comprises decreased T cell activation. In some embodiments, the decreased T cell response comprises decreased T cell survival. In some embodiments, the decreased T cell response comprises decreased T cell proliferation. In some embodiments, the decreased T cell response comprises decreased T cell functionality. In some embodiments, the decreased T cell response comprises a change in T cell phenotype. In some embodiments, the tolerance comprises uncostimulated activation of a T cell. In some embodiments, the tolerance comprises an enhanced Treg response. In some embodiments, the tolerance comprises a decreased B cell response. In some embodiments, the decreased B cell response comprises decreased antibody production. In some embodiments, the tolerance comprises decreased cytokine production. In some embodiments, the tolerance comprises a decreased autoimmune response. In some embodiments, the tolerance comprises a decreased allergic response. In some embodiments, the tolerance comprises a decreased immune response against the transplanted tissue. In some embodiments, the tolerance comprises a decreased pathogenic immune response to the virus. In some embodiments, the tolerance comprises a decreased immune response against a therapeutic agent. In some embodiments, the tolerance comprises a decreased immune response against a therapeutic vehicle.

In some embodiments where a modified anucleate cell is administered to an individual, the method further comprises at least one (such as at least 2, 3, 4, 5, 6, or more) additional administration of a modified anucleate cell as described above. In some embodiments, the duration of time between any two administrations is at least 1 day, 1 week, 1 month, 2 months, 3 months, 4 months, 5 months, 6 months, or 1 year.

Certain aspects of the present invention relate to a system comprising the constriction, cell suspension, and antigen for use in any one of the aforementioned methods. Certain aspects of the present invention relate to a system comprising the constriction, cell suspension, and tolerogenic factor for use in any one of the aforementioned methods.

DETAILED DESCRIPTION

Figure 1B:
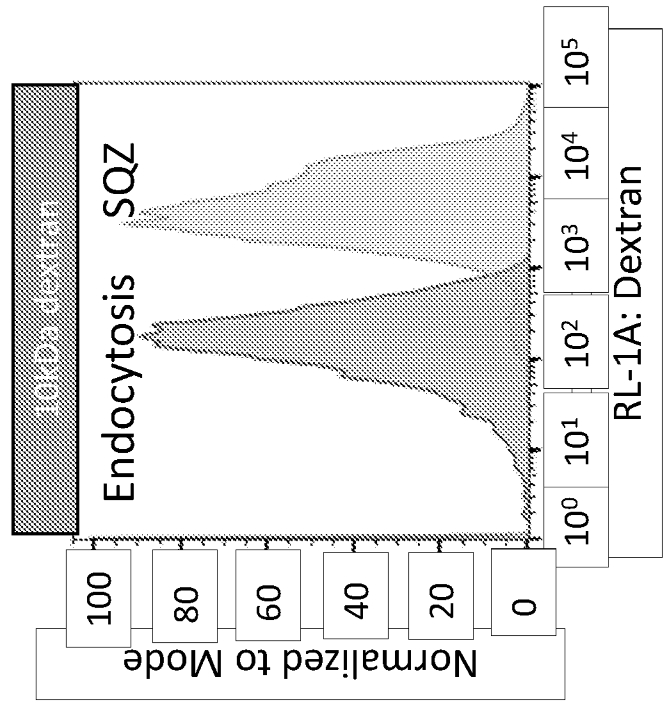
FIGS. 1A&B show exemplary flow cytometry histogram plots depicting fluorescence post constriction mediated delivery (SQZ) of IgG antibody (FIG. 1A) and dextran particles (FIG. 1B) to human RBCs as compared to endocytosis controls.

The invention provides methods of inducing tolerance and/or suppressing an immune response in an individual by passing a cell suspension containing an anucleate cell through a constriction, enabling delivery of an antigen and/or a tolerogenic factor to the anucleate cell. In some embodiments the constriction is contained within a microfluidic channel. In some embodiments the constriction is a pore or contained within a pore.

Certain aspects of the present disclosure relate to methods for inducing tolerance and/or suppressing an immune response to an antigen in an individual, the methods including passing a cell suspension containing an anucleate cell through a constriction, wherein the constriction deforms the cell thereby causing a perturbation of the cell such that an antigen enters the anucleate cell; and introducing the anucleate cell into the individual, wherein presentation of said antigen in a tolerogenic environment induces tolerance and/or suppresses an immune response to the antigen. In some embodiments, the antigen is processed in a tolerogenic environment. In some embodiments, the tolerance and/or immune suppression are antigen-specific. In some embodiments, the tolerance and/or immune suppression are non-specific, including tolerance and/or suppression of an immune response to a plurality of antigens.

Certain aspects of the present disclosure relate to methods for inducing tolerance and/or suppressing an immune response to an antigen in an individual, the methods including passing a cell suspension containing an anucleate cell through a constriction, wherein the constriction deforms the cell thereby causing a perturbation of the cell such that an antigen and a tolerogenic factor contacted with the cell enter the anucleate cell; and introducing the anucleate cell into the individual, thereby inducing tolerance and/or suppressing an immune response to the antigen. In some embodiments, said antigen is presented in a tolerogenic environment. In some embodiments, the tolerogenic factor generates or promotes a tolerogenic environment, wherein presentation of the antigen in said tolerogenic environment induces tolerance and/or suppresses an immune response to the antigen. For example, in some embodiments, the tolerogenic factor acts in a tolerogenic environment to further increase the tolerogenic nature of the environment. In some embodiments, the tolerogenic factor acts in a non-tolerogenic environment to generate a tolerogenic environment. In some embodiments, said antigen is processed in a tolerogenic environment. In some embodiments, the tolerance and/or immune suppression are antigen-specific. In some embodiments, the tolerance and/or immune suppression are non-specific, including tolerance and/or suppression of an immune response to a plurality of antigens.

Certain aspects of the present disclosure relate to methods for inducing tolerance and/or suppressing an immune response to an antigen in an individual, the method including passing a cell suspension containing an anucleate cell through a constriction, wherein the constriction deforms the cell thereby causing a perturbation of the cell such that a tolerogenic factor enters the anucleate cell; and introducing the anucleate cell into the individual, thereby inducing tolerance and/or suppressing an immune response to an antigen. In some embodiments, the tolerogenic factor generates or promotes a tolerogenic environment, wherein presentation of an antigen in said tolerogenic environment induces tolerance and/or suppresses an immune response to the antigen. In some embodiments, the tolerance and/or immune suppression are antigen-specific. In some embodiments, the tolerance and/or immune suppression are non-specific, including tolerance and/or suppression of an immune response to a plurality of antigens.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); PCR 2*: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle. J. B. Griffiths. and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane. Cold Spring Harbor Laboratory Press, 1999); *The Antibodies* (M. Zanetti and J. D. Capra, eds., Harwxood Academic Publishers, 1995); and *Cancer: Principles and Practice of Oncology* (V. T. DeVita et al., eds., J. B. Lippincott Company, 2011).

II. Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising." "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term “membrane” as used herein refers to a selective barrier or sheet containing pores. The term includes a pliable sheetlike structure that acts as a boundary or lining. In some examples, the term refers to a surface or filter containing pores. This term is distinct from the term “cell membrane”.

The term “filter” as used herein refers to a porous article that allows selective passage through the pores. In some examples the term refers to a surface or membrane containing pores.

The term “heterogeneous” as used herein refers to something which is mixed or not uniform in structure or composition. In some examples the term refers to pores having varied sizes, shapes or distributions within a given surface.

The term “homogeneous” as used herein refers to something which is consistent or uniform in structure or composition throughout. In some examples the term refers to pores having consistent sizes, shapes, or distribution within a given surface.

The term “heterologous” as used herein refers to a molecule which is derived from a different organism. In some examples the term refers to a nucleic acid or protein which is not normally found or expressed within the given organism.

As used herein, the term “inhibit” may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, gene editing and so forth. In other examples, inhibition of the expression of a protein may include, but not be limited to, reduction in the transcription of a nucleic acid encoding the protein, reduction in the stability of mRNA encoding the protein, inhibition of translation of the protein, reduction in stability of the protein, and so forth.

As used herein, the term “suppress” may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In other examples, suppression of the expression of a protein may include, but not be limited to, reduction in the transcription of a nucleic acid encoding the protein, reduction in the stability of mRNA encoding the protein, inhibition of translation of the protein, reduction in stability of the protein, and so forth.

As used herein, the term “enhance” may refer to the act of improving, boosting, heightening, or otherwise increasing the presence, or an activity of, a particular target. For example, enhancing an immune response may refer to any act leading to improving, boosting, heightening, or otherwise increasing an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth. In other examples, enhancing the expression of a protein may include, but not be limited to, increase in the transcription of a nucleic acid encoding the protein, increase in the stability of mRNA encoding the protein, increase in translation of the protein, increase in the stability of the protein, and so forth.

As used herein, the term “induce” may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth. In other examples, inducing the expression of a protein may include, but not be limited to, increase in the transcription of a nucleic acid encoding the protein, increase in the stability of mRNA encoding the protein, increase in translation of the protein, increase in the stability of the protein, and so forth.

The term “homologous” as used herein refers to a molecule which is derived from the same organism. In some examples the term refers to a nucleic acid or protein which is normally found or expressed within the given organism.

The term “polynucleotide” or “nucleic acid” as used herein refers to a polymeric form of nucleotides of any length, including ribonucleotides and deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. The backbone of the polynucleotide can comprise repeating units, such as N-(2-aminoethyl)-glycine, linked by peptide bonds (i.e., peptide nucleic acid). Alternatively, the backbone of the polynucleotide can comprise a polymer of synthetic subunits such as phosphoramidates and thus can be an oligodeoxynucleotide phosphoramidate (P—NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms “polypeptide” and “protein” are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a “polypeptide” refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

For any of the structural and functional characteristics described herein, methods of determining these characteristics are known in the art.

III. Immune Suppression and Tolerance

In certain aspects, the invention provides methods for suppressing an immune response and/or inducing tolerance in an individual, the method comprising passing a cell suspension comprising an anucleate cell through a constriction, wherein said constriction deforms the cell thereby causing a perturbation of the cell such that an antigen and/or tolerogenic compound enters the anucleate cell and introducing the anucleate cell into the individual, wherein said antigen is processed in a tolerogenic environment, wherein presentation of said antigen in said tolerogenic environment suppresses an immune response to the antigen.

Immunological tolerance is an immunological unresponsiveness to challenge with the antigen to which tolerance has been induced. Tolerance is demonstrated when a subject is unresponsive to subsequent challenge with the tolerance-inducing antigen. Tolerance can be mediated by several different mechanisms which include apoptosis of the autoreactive cells, induction of anergy, or deviation of lymphocyte phenotype. In some embodiments, the tolerance may include T cell non-responsiveness, causing deactivation of immune response to a specific antigen. Tolerance can also be mediated by regulatory T cells (Tregs) through secretion of immunosuppressive cytokines and via contact-dependent interactions with cell surface molecules or cytotoxic factors. Defects in tolerogenic mechanisms can contribute to autoimmune diseases, transplantation rejection, anti-drug responses, and pathogenic responses to viral infection. Immunosuppression is a decrease in the activity of the immune response. For example, immunosuppression may include, without limitation, decreased responsiveness to challenge with antigen, decreased immune cell activation and proliferation, modulated cytokine secretion, decreased immune cell survival, or decreased immune cell effector functions. In some embodiments, the immunosuppression is specific for a given antigen. For example, an immune response against a self-antigen is suppressed.

In some embodiments, antigen is processed and presented in a tolerogenic environment. A tolerogenic environment may be a location within the body which supports the generation of a tolerogenic immune response. In some embodiments, the tolerogenic environment is located in a primary lymphoid tissue, such as the thymus. In some embodiments, the tolerogenic environment is located in a secondary lymphoid tissue. Exemplary secondary lymphoid tissues include the spleen, lymph nodes, and mucosa-associated lymphoid tissues (MALT). In some embodiments, the tolerogenic environment is located in the spleen. In some embodiments, the tolerogenic environment is located in a non-lymphoid tissue such as the liver. In some embodiments, the tolerogenic environment is induced at a site of inflammation by delivery of a tolerogenic factor. For example, an inflammatory environment is converted to a tolerogenic environment by a tolerogenic factor.

In some embodiments, the invention provides methods for delivery to an anucleate cell, wherein the cell is a mammalian cell. Anucleate cells lack a nucleus. In some embodiments, the anucleate cell is a monkey, mouse, dog, cat, horse, rat, sheep, goat pig, or rabbit cell. In some embodiments, the anucleate cell is a human cell. In some embodiments, the anucleate cell is a non-mammalian cell. In some embodiments, the anucleate cell is a chicken, frog, insect, fish, or nematode cell. In some embodiments, the anucleate cell is a red blood cell. Red blood cells (RBCs) are flexible and oval biconcave discs with cytoplasm rich in the oxygen-carrier biomolecule hemoglobin. RBCs serve as the primary means for oxygen delivery and carbon dioxide removal throughout the human body. RBCs can stay in circulation for up to 120 days, after which they are removed from the body via clearance in the spleen. Reticulocytes are anucleate immature (not yet biconcave) red blood cells and typically comprise about 1% of the red blood cells in the human body. Mature red blood cells are also referred to as erythrocytes. In some embodiments, the anucleate cell is a platelet. Platelets, also called thrombocytes, are a component of blood whose function involves blood clotting. Platelets are biconvex discoid (lens-shaped) structures 2-3 μm in diameter.

In some embodiments, presentation of antigen in a tolerogenic environment suppresses an immune response to the antigen or induces a tolerogenic response to the antigen. Antigens derived from apoptotic cells, such as RBCs, that are regularly cleared in the tolerogenic environment of the spleen, may drive tolerance and/or suppress an immune response to the antigens via deletion (e.g., killing) or anergy of reactive T cells. In some embodiments, the tolerance and/or immune suppression is antigen-specific. RBCs have a limited life span and are unable to self-repair, leading to RBC death by eryptosis, a process similar to apoptosis, and subsequently removal from the bloodstream. In some embodiments, the antigen may be released upon apoptosis of the anucleate cell within the tolerogenic environment, where it is subsequently engulfed, processed, and presented by an antigen-presenting cell. In some embodiments, the anucleate cell containing the antigen is phagocytosed by an antigen-presenting cell, such as a macrophage, and the antigen is subsequently processed and presented by the antigen-presenting cell.

In some embodiments, the half-life of the anucleate cell can be modified. In some embodiments, the half-life of the anucleate cell is increased. For example, the anucleate may be modified to increase the time the anucleate cell circulates in the blood stream before clearance in the spleen. In some embodiments, the half-life of the anucleate cell is decreased. For example, the anucleate cell may be modified to decrease the time the anucleate cell circulates in the blood stream before clearance in the spleen. In some embodiments, an altered ratio of lipids on the anucleate cell surface decreases the half-life of the anucleate cell. For example, the presence of phosphatidylserine on the surface of the anucleate cell can be increased to decrease the half-life of the anucleate cell, such as by using any method known in the art for increasing surface phosphatidylserine (see Hamidi et al., *J. Control. Release,* 2007, 118(2): 145-60). Phosphatidylserine exposure on the outer cell membrane is a hallmark of apoptosis and is recognized by receptors on phagocytes in a manner that promotes engulfment. In some embodiments, the anucleate cell is incubated with lipids prior to delivery to an individual. In some embodiments, the anucleate cell is associated with a polymer to decrease the half-life of the anucleate cell.

In certain aspects, the invention provides methods for suppressing an immune response to an antigen in an individual, the method comprising passing a cell suspension comprising an anucleate cell through a constriction, wherein said constriction deforms the cell thereby causing a perturbation of the cell such that an antigen enters the anucleate cell and introducing the anucleate cell into the individual, wherein presentation of said antigen in a tolerogenic environment suppresses an immune response to the antigen. In some embodiments, the antigen is processed in a tolerogenic environment. In some embodiments, the immune response is antigen-specific.

In certain aspects, the invention provides methods for suppressing an immune response in an individual, the method comprising passing a cell suspension comprising an anucleate cell through a constriction, wherein said constriction deforms the cell thereby causing a perturbation of the cell such that a tolerogenic factor enters the anucleate cell and introducing the anucleate cell into the individual, thereby suppressing an immune response. In some embodiments, the tolerogenic factor generates or promotes a tolerogenic environment, wherein presentation of an antigen in said tolerogenic environment suppresses an immune response to the antigen. In some embodiments, the immune suppression is non-specific, including suppression of an immune response to a plurality of antigens.

In certain aspects, the invention provides methods for suppressing an immune response to an antigen in an individual, the method comprising passing a cell suspension comprising an anucleate cell through a constriction, wherein said constriction deforms the cell thereby causing a perturbation of the cell such that an antigen and a tolerogenic factor enter the anucleate cell and introducing the anucleate cell into the individual, thereby suppressing an immune response to the antigen. In some embodiments, the antigen is presented in a tolerogenic environment. In some embodiments, the tolerogenic factor generates or promotes a tolerogenic environment, wherein presentation of said antigen in said tolerogenic environment suppresses an immune response to the antigen. In some embodiments, the antigen is processed in a tolerogenic environment. In some embodiments, the immune suppression is antigen-specific. In some embodiments, the immune suppression is non-specific, including suppression of an immune response to a plurality of antigens.

In certain aspects, the present invention provides methods for suppressing an immune response to an antigen in an individual, comprising passing a first cell suspension comprising a first anucleate cell through a constriction, wherein said constriction deforms the cell thereby causing a perturbation of the cell such that an antigen enters the anucleate cell, passing a second cell suspension comprising a second anucleate cell through a constriction, wherein said constriction deforms the cell thereby causing a perturbation of the cell such that a tolerogenic factor enters the anucleate cell, and introducing the first anucleate cell and second anucleate cell into the individual, thereby suppressing an immune response to the antigen. In some embodiments, the antigen is presented in a tolerogenic environment. In some embodiments, the tolerogenic factor generates or promotes a tolerogenic environment, wherein presentation of said antigen in said tolerogenic environment suppresses an immune response to the antigen. In some embodiments, the antigen is processed in a tolerogenic environment. In some embodiments, the first anucleate cell and second anucleate cell are introduced simultaneously. In some embodiments, the first anucleate cell and second anucleate cell are introduced sequentially. In some embodiments, the first anucleate cell is introduced to the individual before introduction of the second anucleate cell. In some embodiments, the first anucleate cell is introduced to the individual more than any of about 1 minute, 5 minutes, 10 minutes, 15 minutes, 30 minutes, 1 hour, 2 hours, 3 hours, 4 hours, 5 hours, 6 hours, 12 hours, or 24 hours before introduction of the second anucleate cell. In some embodiments, the second anucleate cell is introduced to the individual before introduction of the first anucleate cell. In some embodiments, the second anucleate cell is introduced to the individual more than any of about 1 minute, 5 minutes, 10 minutes, 15 minutes, 30 minutes, 1 hour, 2 hours, 3 hours, 4 hours, 5 hours, 6 hours, 12 hours, or 24 hours before introduction of the first anucleate cell. In some embodiments, the immune suppression is antigen-specific. In some embodiments, the immune suppression is non-specific, including suppression of an immune response to a plurality of antigens.

In certain aspects, the invention provides a method for inducing tolerance to an antigen in an individual, the method comprising passing a cell suspension comprising an anucleate cell through a constriction, wherein said constriction deforms the cell thereby causing a perturbation of the cell such that an antigen enters the anucleate cell and introducing the anucleate cell into the individual, wherein presentation of said antigen in a tolerogenic environment induces tolerance to the antigen. In some embodiments, the antigen is processed in a tolerogenic environment. In some embodiments, the tolerance is antigen-specific.

In certain aspects, the invention provides methods for inducing tolerance to an antigen in an individual, the method comprising passing a cell suspension comprising an anucleate cell through a constriction, wherein said constriction deforms the cell thereby causing a perturbation of the cell such that a tolerogenic factor enters the anucleate cell, and introducing the anucleate cell into the individual, thereby inducing tolerance to the antigen. In some embodiments, the tolerogenic factor generates or promotes a tolerogenic environment, and presentation of the antigen in said tolerogenic environment induces tolerance to the antigen. In some embodiments, the tolerance is non-specific, including tolerance to a plurality of antigens.

In certain aspects, the invention provides a method for inducing tolerance to an antigen in an individual, the method comprising passing a cell suspension comprising an anucleate cell through a constriction, wherein said constriction deforms the cell thereby causing a perturbation of the cell such that an antigen and a tolerogenic factor enter the anucleate cell and introducing the anucleate cell into the individual, thereby inducing tolerance to the antigen. In some embodiments, the antigen is presented in a tolerogenic environment. In some embodiments, the tolerogenic factor generates or promotes a tolerogenic environment, wherein presentation of said antigen in said tolerogenic environment induces tolerance to the antigen. In some embodiments, the antigen is processed in a tolerogenic environment. In some embodiments, the tolerance is antigen-specific. In some embodiments, the tolerance is non-specific, including tolerance to a plurality of antigens.

In certain aspects, the invention provides methods for inducing tolerance to an antigen in an individual, comprising passing a first cell suspension comprising a first anucleate cell through a constriction, wherein said constriction deforms the cell thereby causing a perturbation of the cell such that an antigen enters the anucleate cell, passing a second cell suspension comprising a second anucleate cell through a constriction, wherein said constriction deforms the cell thereby causing a perturbation of the cell such that a tolerogenic factor enters the anucleate cell, and introducing the first anucleate cell and second anucleate cell into the individual, thereby inducing tolerance to the antigen. In some embodiments, the antigen is presented in a tolerogenic environment. In some embodiments, the tolerogenic factor generates or promotes a tolerogenic environment, wherein presentation of said antigen in said tolerogenic environment induces tolerance to the antigen. In some embodiments, the antigen is processed in a tolerogenic environment. In some embodiments, the first anucleate cell and second anucleate cell are introduced simultaneously. In some embodiments, the first anucleate cell and second anucleate cell are introduced sequentially. In some embodiments, the first anucleate cell is introduced to the individual before introduction of the second anucleate cell. In some embodiments, the first anucleate cell is introduced to the individual more than any of about 1 minute, 5 minutes, 10 minutes, 15 minutes, 30 minutes, 1 hour, 2 hours, 3 hours, 4 hours, 5 hours, 6 hours, 12 hours, or 24 hours before introduction of the second anucleate cell. In some embodiments, the second anucleate cell is introduced to the individual before introduction of the first anucleate cell. In some embodiments, the second anucleate cell is introduced to the individual more than any of about 1 minute, 5 minutes, 10 minutes, 15 minutes, 30 minutes, 1 hour, 2 hours, 3 hours, 4 hours, 5 hours, 6 hours, 12 hours, or 24 hours before introduction of the first anucleate cell. In some embodiments, the tolerance is antigen-specific. In some embodiments, the tolerance is non-specific, including tolerance to a plurality of antigens.

In certain aspects, the invention provides methods for inducing tolerance to an antigen in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein presentation of said antigen in a tolerogenic environment induces tolerance to the antigen. In some embodiments, the antigen is processed in a tolerogenic environment. In some embodiments, the tolerance is antigen-specific.

In certain aspects, the invention provides methods for suppressing an immune response to an antigen in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein presentation of said antigen in a tolerogenic environment suppresses an immune response to the antigen. In some embodiments, the antigen is processed in a tolerogenic environment. In some embodiments, the immune suppression is antigen-specific.

In certain aspects, the invention provides methods for inducing tolerance to an antigen in an individual, the method comprising introducing an anucleate cell into the individual, wherein the anucleate cell comprises a tolerogenic factor, wherein the tolerogenic factor was introduced to the anucleate cell by passing the anucleate cell through a constriction, wherein said constriction deformed the cell thereby causing a perturbation of the cell such that the tolerogenic factor entered the anucleate cell, thereby inducing tolerance to the antigen. In some embodiments, the tolerogenic factor generates or promotes a tolerogenic environment, wherein presentation of the antigen in said tolerogenic environment induces tolerance to the antigen. In some embodiments, the tolerance is non-specific, including tolerance to a plurality of antigens.

In certain aspects, the invention provides methods for suppressing an immune response to an antigen in an individual, the method comprising introducing an anucleate cell into the individual, wherein the anucleate cell comprises a tolerogenic factor, wherein the tolerogenic factor was introduced to the anucleate cell by passing the anucleate cell through a constriction, wherein said constriction deformed the cell thereby causing a perturbation of the cell such that the tolerogenic factor entered the anucleate cell, thereby suppressing an immune response to the antigen. In some embodiments, the tolerogenic factor generates or promotes a tolerogenic environment, wherein presentation of the antigen in said tolerogenic environment suppresses an immune response to the antigen. In some embodiments, the immune suppression is non-specific, including suppression of an immune response to a plurality of antigens.

In certain aspects, the invention provides methods for inducing tolerance to an antigen in an individual, the method comprising introducing an anucleate cell into the individual, wherein the anucleate cell comprises an antigen and a tolerogenic factor, wherein the antigen and the tolerogenic factor were introduced to the anucleate cell by passing the anucleate cell through a constriction, wherein said constriction deformed the cell thereby causing a perturbation of the cell such that the antigen and the tolerogenic factor entered the anucleate cell, wherein presentation of said antigen induces tolerance to the antigen. In some embodiments, the tolerogenic factor generates or promotes a tolerogenic environment, wherein presentation of said antigen in said tolerogenic environment induces tolerance to the antigen. In some embodiments, the antigen is processed in a tolerogenic environment. In some embodiments, the tolerance is antigen-specific. In some embodiments, the tolerance is non-specific, including tolerance to a plurality of antigens.

In certain aspects, the invention provides methods for suppressing an immune response to an antigen in an individual, the method comprising introducing an anucleate cell into the individual, wherein the anucleate cell comprises an antigen and a tolerogenic factor, wherein the antigen and the tolerogenic factor were introduced to the anucleate cell by passing the anucleate cell through a constriction, wherein said constriction deformed the cell thereby causing a perturbation of the cell such that the antigen and the tolerogenic factor entered the anucleate cell, wherein presentation of said antigen suppresses an immune response to the antigen. In some embodiments, the tolerogenic factor generates or promotes a tolerogenic environment, wherein presentation of said antigen in said tolerogenic environment suppresses an immune response to the antigen. In some embodiments, the antigen is processed in a tolerogenic environment. In some embodiments, the immune suppression is antigen-specific. In some embodiments, the immune suppression is non-specific, including suppression of an immune response to a plurality of antigens.

In certain aspects, the invention provides methods for introducing an antigen into a tolerogenic environment in an individual, comprising delivering an anucleate cell into the individual, wherein the anucleate cell comprises the antigen, wherein the antigen was introduced to the anucleate cell by passing the anucleate cell through a constriction, and wherein said constriction deformed the cell thereby causing a perturbation of the cell such that the antigen entered the anucleate cell. In some embodiments, the antigen is presented in the tolerogenic environment. In some embodiments, the antigen is processed in the tolerogenic environment.

In certain aspects, the invention provides methods for generating a tolerogenic environment in an individual, comprising delivering an anucleate cell into the individual, wherein the anucleate cell comprises a tolerogenic factor, wherein the tolerogenic factor was introduced to the anucleate cell by passing the anucleate cell through a constriction, wherein said constriction deformed the cell thereby causing a perturbation of the cell such that the tolerogenic factor entered the anucleate cell. In some embodiments, presentation of an antigen in the tolerogenic environment induces tolerance and/or suppresses an immune response to the antigen. In some embodiments, the tolerance and/or immune suppression are non-specific, including tolerance and/or suppression of an immune response to a plurality of antigens.

In some embodiments, the immune response is suppressed by at least any of about 10%, about 15%, about 20%, about 25%, about 30%, about 40%, about 50%, about 60%, about 70%, about 75%, about 80%, about 90%, or about 100%. In some embodiments, the suppressed immune response and/or induced tolerance comprise a decreased T cell response. For example, a decreased T cell response may include, without limitation, decreased T cell activation or proliferation, decreased T cell survival, or decreased cell functionality. In some embodiments, the decreased T cell response comprises decreased T cell activation. In some embodiments, the decreased T cell response comprises decreased T cell survival. In some embodiments, the decreased T cell response comprises decreased T cell proliferation. In some embodiments, the decreased T cell response comprises decreased T cell functionality. For example, decreased T cell functionality can include, without limitation, modulated cytokine secretion, decreased T cell migration to sites of inflammation, and decreased T cell cytotoxic activity. In some embodiments, the suppressed immune response and/or induced tolerance comprise decreased inflammatory cytokine production and/or secretion, and/or increased anti-inflammatory cytokine production and/or secretion. In some embodiments, the suppressed immune response and/or induced tolerance comprise decreased production and/or secretion of one or more inflammatory cytokines selected from interleukin-1 (IL-1), IL-12, and IL-18, tumor necrosis factor (TNF), interferon gamma (IFN-gamma), and granulocyte-macrophage colony stimulating factor (GM-CSF). In some embodiments, the suppressed immune response and/or induced tolerance comprise decreased production and/or secretion of one or more anti-inflammatory cytokines selected from IL-4. IL-10. IL-13. IL-35, IFN-alpha and transforming growth factor-beta (TGFβ). In some embodiments, the suppressed immune response and/or induced tolerance comprises a change in T cell phenotype. For example, the T cell state may change from a proinflammatory phenotype to a regulatory or anti-inflammatory phenotype. In some embodiments, the suppressed immune response and/or induced tolerance comprises uncostimulated activation of a T cell, which may subsequently lead to cell death. In some embodiments, the suppressed immune response and/or induced tolerance comprise an enhanced Treg response. In some embodiments, the suppressed immune response and/or induced tolerance comprise a decreased B cell response. In some embodiments, the decreased B cell response comprises decreased antibody production.

In some embodiments, the suppressed immune response and/or induced tolerance comprise a decreased autoimmune response. For example, the decreased autoimmune response can include, without limitation, a decreased immune response or induced tolerance against an antigen associated with Type I Diabetes, Rheumatoid arthritis, Psoriasis, Multiple Sclerosis, Neurodegenerative diseases which may have an immune component such as Alzheimer's disease, ALS. Huntington's Disease, and Parkinson's Disease, Systemic Lupus Erthyromatosus. Sjogren's Disease. Crohn's disease, or Ulcerative Colitis. In some embodiments, the suppressed immune response and/or induced tolerance comprise a decreased allergic response. For example, the decreased allergic response can include a decreased immune response or induced tolerance against antigens associated with allergic asthma, atopic dermatitis, allergic rhinitis (hay fever), or food allergy. In some embodiments, the antigen is an antigen associated with transplanted tissue. In some embodiments, the suppressed immune response and/or induced tolerance comprises a decreased immune response or induced tolerance against the transplanted tissue. In some embodiments, the antigen is associated with a virus. In some embodiments, the suppressed immune response and/or induced tolerance comprises a decreased pathogenic immune response or induced tolerance to the virus. For example, the pathogenic immune response can include the cytokine storm generated by certain viral infections. A cytokine storm is a potentially fatal immune reaction consisting of a positive feedback loop between cytokines and white blood cells.

In some embodiments, the suppressed immune response comprises a decreased immune response against a therapeutic agent. In some embodiments, the therapeutic agent is a clotting factor. Exemplary clotting factors include, without limitation, Factor VIII and Factor IX. In some embodiments, the therapeutic agent is an antibody. Exemplary therapeutic antibodies include, without limitation, anti-TNFα, anti-VEGF, anti-CD3, anti-CD20, anti-IL-2R, anti-Her2, anti-RSVF, anti-CEA, anti-IL-1beta, anti-CD15, anti-myosin, anti-PSMA, anti-40 kDa glycoprotein, anti-CD33, anti-CD52, anti-IgE, anti-CD11a, anti-EGFR, anti-C5, anti-alpha-4 integrin, anti-IL-12/IL-23, anti-IL-6R. and anti-RANKL. In some embodiments, the therapeutic agent is a growth factor. Exemplary therapeutic growth factors include, without limitation, Erythropoietin (EPO) and megakaryocyte differentiation and growth factor (MDGF). In some embodiments, the therapeutic agent is a hormone. Exemplary therapeutic hormones include, without limitation, insulin, human growth hormone, and follicle stimulating hormone. In some embodiments, the therapeutic agent is a recombinant cytokine. Exemplary therapeutic recombinant cytokines include, without limitation. IFNβ. IFNα, and GM-CSF. In some embodiments, the suppressed immune response comprises a decreased immune response against a therapeutic vehicle. In some embodiments, the therapeutic vehicle is a virus, such as an adenovirus, adeno-associated virus, baculovirus, herpes virus, or retrovirus used for gene therapy. In some embodiments, the therapeutic vehicle is a liposome. In some embodiments, the therapeutic vehicle is a nanoparticle.

IV. Microfluidic Channels to Provide Cell-Deforming Constrictions

In some embodiments, the invention provides methods for suppressing an immune response or inducing tolerance by passing a cell suspension through a constriction, wherein the constriction deforms the anucleate cell thereby causing a perturbation of the cell such that an antigen or compound enters the cell, wherein the constriction is contained within a microfluidic channel. In some embodiments, multiple constrictions can be placed in parallel and/or in series within the microfluidic channel. Exemplary microfluidic channels containing cell-deforming constrictions for use in the methods disclosed herein are described in WO2013059343. Exemplary surfaces having pores for use in the methods disclosed herein are described in U.S. Provisional Application 62/214,820, filed Sep. 4, 2015.

In some embodiments, the microfluidic channel includes a lumen and is configured such that a cell suspended in a buffer can pass through, wherein the microfluidic channel includes a constriction. The microfluidic channel can be made of any one of a number of materials, including silicon, metal (e.g., stainless steel), plastic (e.g., polystyrene, PET, PETG), ceramics, glass, crystalline substrates, amorphous substrates, or polymers (e.g., Poly-methyl methacrylate (PMMA), PDMS, Cyclic Olefin Copolymer (COC), etc.). Fabrication of the microfluidic channel can be performed by any method known in the art, including dry etching, wet etching, photolithography, injection molding, laser ablation, or SU-8 masks.

In some embodiments, the constriction within the microfluidic channel includes an entrance portion, a centerpoint, and an exit portion. In some embodiments, the length, depth, and width of the constriction within the microfluidic channel can vary. In some embodiments, the diameter of the constriction within the microfluidic channel is a function of the diameter of the cell or cluster of cells. In some embodiments, the diameter of the constriction within the microfluidic channel is about 10%, to about 99% of the diameter of the cell. In some embodiments, the constriction size is about 10%, about 15%, about 20%, about 30%, about 40%, about 50%, about 60%, about 70%, about 80%, about 90%, or about 99% of the cell diameter. In some embodiments, the constriction size is about 10%, about 15%, about 20%, about 30%, about 40%, about 50%, about 60%, about 70%, about 80%, about 90%, or about 99% of the minimum cross-sectional distance of the cell (e.g., an anucleate cell such as an RBC). In some embodiments, the channel comprises a constriction width of about 0.25 μm to about 4 μm. In some embodiments, the channel comprises a constriction width of width of about 4 μm, about 3.5 μm, about 3 μm, about 2.5 μm, about 2 μm, about 1 μm, about 0.5 μm, or about 0.25 μm (including any ranges between these values). The cross-section of the channel, the entrance portion, the centerpoint, and the exit portion can also vary. For example, the cross-sections can be circular, elliptical, an elongated slit, square, hexagonal, or triangular in shape. The entrance portion defines a constriction angle, wherein the constriction angle is optimized to reduce clogging of the channel and optimized for enhanced delivery of a compound into the cell. The angle of the exit portion can vary as well. For example, the angle of the exit portion is configured to reduce the likelihood of turbulence that can result in non-laminar flow. In some embodiments, the walls of the entrance portion and/or the exit portion are linear. In other embodiments, the walls of the entrance portion and/or the exit portion are curved.

V. Surface Having Pores to Provide Cell Deforming Constrictions

In some embodiments, the invention provides methods for suppressing an immune response or inducing tolerance by passing a cell suspension through a constriction, wherein the constriction deforms the anucleate cell thereby causing a perturbation of the cell such that an antigen compound enters the cell, wherein the constriction is a pore or contained within a pore. In some embodiments, the pore is contained in a surface. Exemplary surfaces having pores for use in the methods disclosed herein are described in U.S. Provisional Application 62/214,820, filed Sep. 4, 2015.

The surfaces as disclosed herein can be made of any one of a number of materials and take any one of a number of forms. In some embodiments, the surface is a filter. In some embodiments, the surface is a membrane. In some embodiments, the filter is a tangential flow filter. In some embodiments, the surface is a sponge or sponge-like matrix. In some embodiments, the surface is a matrix.

In some embodiments the surface is a tortuous path surface. In some embodiments, the tortuous path surface comprises cellulose acetate. In some embodiments, the surface comprises a material selected from, without limitation, synthetic or natural polymers, polycarbonate, silicon, glass, metal, alloy, cellulose nitrate, silver, cellulose acetate, nylon, polyester, polyethersulfone, polyacrylonitrile (PAN), polypropylene, PVDF, polytetrafluorethylene, mixed cellulose ester, porcelain, and ceramic.

The surface disclosed herein can have any shape known in the art; e.g. a 3-dimensional shape. The 2-dimensional shape of the surface can be, without limitation, circular, elliptical, round, square, star-shaped, triangular, polygonal, pentagonal, hexagonal, heptagonal, or octagonal. In some embodiments, the surface is round in shape. In some embodiments, the surface 3-dimensional shape is cylindrical, conical, or cuboidal.

The surface can have various cross-sectional widths and thicknesses. In some embodiments, the surface cross-sectional width is between about 1 mm and about 1 m or any cross-sectional width or range of cross-sectional widths therebetween. In some embodiments, the surface has a defined thickness. In some embodiments, the surface thickness is uniform. In some embodiments, the surface thickness is variable. For example, in some embodiments, portions of the surface are thicker or thinner than other portions of the surface. In some embodiments, the surface thickness varies by about 1% to about 90% or any percentage or range of percentages therebetween. In some embodiments, the surface is between about 0.01 μm to about 5 mm thick or any thickness or range of thicknesses therebetween.

In some embodiments, the constriction is a pore or contained within a pore. The cross-sectional width of the pores is related to the type of cell to be treated. In some embodiments, the pore size is a function of the diameter of the cell of cluster of cells to be treated. In some embodiments, the pore size is such that a cell is perturbed upon passing through the pore. In some embodiments, the pore size is less than the diameter of the cell. In some embodiments, the pore size is about 10% to about 99% of the diameter of the cell. In some embodiments, the pore size is about 10%, about 15%, about 20%, about 30%, about 40%, about 50%, about 60%, about 70%, about 80%, about 90%, or about 99% of the cell diameter. Optimal pore size or pore cross-sectional width can vary based upon the application and/or cell type. In some embodiments, the pore size is about 0.1 μm to about 4 μm. In some embodiments, the pore size is about 4 μm, about 3 μm, about 2 μm, about 1 μm, about 0.5 μm, about 0.25 μm, or about 0.1 μm. In some embodiments, the pore cross-sectional width is at or less than any of about 4 μm, about 3 μm, about 2 μm, about 1 μm, about 0.5 μm, about 0.25 μm, or about 0.1 μm. The entrances and exits of the pore passage may have a variety of angles. The pore angle can be selected to minimize clogging of the pore while cells are passing through. In some embodiments, the flow rate through the surface is between about 0.001 $mL/cm^2/sec$ to about 100 $L/cm^2/sec$ or any rate or range of rates therebetween. For example, the angle of the entrance or exit portion can be between about 0 and about 90 degrees. In some embodiments, the entrance or exit portion can be greater than 90 degrees. In some embodiments, the pores have identical entrance and exit angles. In some embodiments, the pores have different entrance and exit angles. In some embodiments, the pore edge is smooth, e.g. rounded or curved. A smooth pore edge has a continuous, flat, and even surface without bumps, ridges, or uneven parts. In some embodiments, the pore edge is sharp. A sharp pore edge has a thin edge that is pointed or at an acute angle. In some embodiments, the pore passage is straight. A straight pore passage does not contain curves, bends, angles, or other irregularities. In some embodiments, the pore passage is curved. A curved pore passage is bent or deviates from a straight line. In some embodiments, the pore passage has multiple curves, e.g. about 2, 3, 4, 5, 6, 7, 8, 9, 10 or more curves.

The pores can have any shape known in the art, including a 2-dimensional or 3-dimensional shape. The pore shape (e.g., the cross-sectional shape) can be, without limitation, circular, elliptical, round, square, star-shaped, triangular, polygonal, pentagonal, hexagonal, heptagonal, and octagonal. In some embodiments, the cross-section of the pore is round in shape. In some embodiments, the 3-dimensional shape of the pore is cylindrical or conical. In some embodiments, the pore has a fluted entrance and exit shape. In some embodiments, the pore shape is homogenous (i.e. consistent or regular) among pores within a given surface. In some embodiments, the pore shape is heterogeneous (i.e. mixed or varied) among pores within a given surface.

The surfaces described herein can have a range of total pore numbers. In some embodiments, the pores encompass about 10% to about 80% of the total surface area. In some embodiments, the surface contains about $1.0\times10^{5}$ to about $1.0\times10^{30}$ total pores or any number or range of numbers therebetween. In some embodiments, the surface comprises between about 10 and about $1.0\times10^{15}$ pores per $mm^2$ surface area.

The pores can be distributed in numerous ways within a given surface. In some embodiments, the pores are distributed in parallel within a given surface. In one such example, the pores are distributed side-by-side in the same direction and are the same distance apart within a given surface. In some embodiments, the pore distribution is ordered or homogeneous. In one such example, the pores are distributed in a regular, systematic pattern or are the same distance apart within a given surface. In some embodiments, the pore distribution is random or heterogeneous. In one such example, the pores are distributed in an irregular, disordered pattern or are different distances apart within a given surface. In some embodiments, multiple surfaces are distributed in series. The multiple surfaces can be homogeneous or heterogeneous in surface size, shape, and/or roughness. The multiple surfaces can further contain pores with homogeneous or heterogeneous pore size, shape, and/or number, thereby enabling the simultaneous delivery of a range of compounds into different cell types.

In some embodiments, an individual pore has a uniform width dimension (i.e. constant width along the length of the pore passage). In some embodiments, an individual pore has a variable width (i.e. increasing or decreasing width along the length of the pore passage). In some embodiments, pores within a given surface have the same individual pore depths. In some embodiments, pores within a given surface have different individual pore depths. In some embodiments, the pores are immediately adjacent to each other. In some embodiments, the pores are separated from each other by a distance. In some embodiments, the pores are separated from each other by a distance of about 0.001 μm to about 30 mm or any distance or range of distances therebetween.

In some embodiments, the surface is coated with a material. The material can be selected from any material known in the art, including, without limitation, Teflon, an adhesive coating, surfactants, proteins, adhesion molecules, antibodies, anticoagulants, factors that modulate cellular function, nucleic acids, lipids, carbohydrates, or transmembrane proteins. In some embodiments, the surface is coated with polyvinylpyrrolidone. In some embodiments, the material is covalently attached to the surface. In some embodiments, the material is noncovalently attached to the surface. In some embodiments, the surface molecules are released at the cells pass through the pores.

In some embodiments, the surface has modified chemical properties. In some embodiments, the surface is hydrophilic. In some embodiments, the surface is hydrophobic. In some embodiments, the surface is charged. In some embodiments, the surface is positively and/or negatively charged. In some embodiments, the surface can be positively charged in some regions and negatively charged in other regions. In some embodiments, the surface has an overall positive or overall negative charge. In some embodiments, the surface can be any one of smooth, electropolished, rough, or plasma treated. In some embodiments, the surface comprises a zwitterion or dipolar compound. In some embodiments, the surface is plasma treated.

In some embodiments, the surface is contained within a larger module. In some embodiments, the surface is contained within a syringe, such as a plastic or glass syringe. In some embodiments, the surface is contained within a plastic filter holder. In some embodiments, the surface is contained within a pipette tip.

VI. Cell Perturbations

In some embodiments, the invention provides methods for suppressing an immune response or inducing tolerance by passing a cell suspension through a constriction, wherein the constriction deforms the anucleate cell thereby causing a perturbation of the cell such that an antigen or compound enters the cell, wherein the perturbation in the cell is a breach in the cell that allows material from outside the cell to move into the cell (e.g., a hole, tear, cavity, aperture, pore, break, gap, perforation). The deformation can be caused by, for example, pressure induced by mechanical strain and/or shear forces. In some embodiments, the perturbation is a perturbation within the cell membrane. In some embodiments, the perturbation is transient. In some embodiments, the cell perturbation lasts from about $1.0\times10^{-9}$ seconds to about 2 hours, or any time or range of times therebetween. In some embodiments, the cell perturbation lasts for about $1.0\times10^{-9}$ second to about 1 second, about 1 second to about 1 minute, or about 1 minute to about 1 hour. In some embodiments, the cell perturbation lasts for between any one of about $1.0\times10^{-9}$ to about $1.0\times10^{-1}$, about $1.0\times10^{-9}$ to about $1.0\times10^{-2}$, about $1.0\times10^{-9}$ to about $1.0\times10^{-3}$, about $1.0\times10^{-9}$ to about $1.0\times10^{-4}$, about $1.0\times10^{-9}$ to about $1.0\times10^{-5}$, about $1.0\times10^{-9}$ to about $1.0\times10^{-6}$, about $1.0\times10^{-9}$ to about $1.0\times10^{-8}$, or about $1.0\times10^{-9}$ to about $1.0\times10^{-8}$ seconds. In some embodiment, the cell perturbation lasts for any one of about $1.0\times10^{-8}$ to about $1.0\times10^{-1}$, about $1.0\times10^{-7}$ to about $1.0\times10^{-1}$, about $1.0\times10^{-6}$ to about $1.0\times10^{-1}$, about $1.0\times10^{-5}$ to about $1.0\times10^{-1}$, about $1.0\times10^{-4}$ to about $1.0\times10^{-1}$, about $1.0\times10^{-3}$ to about $1.0\times10^{-91}$, or about $1.0\times10^{-2}$ to about $1.0\times10^{-1}$ seconds. The cell perturbations (e.g., pores or holes) created by the methods described herein are not formed as a result of assembly of protein subunits to form a multimeric pore structure such as that created by complement or bacterial hemolysins.

As the cell passes through the constriction, the constriction temporarily imparts injury to the cell membrane that causes passive diffusion of material through the perturbation. In some embodiments, the cell is only deformed for a brief period of time, on the order of 100 μs to minimize the chance of activating apoptotic pathways through cell signaling mechanisms, although other durations are possible (e.g., ranging from nanoseconds to hours). In some embodiments, the cell is deformed for about $1.0\times10^{-9}$ seconds to about 2 hours, or any time or range of times therebetween. In some embodiments, the cell is deformed for about $1.0\times10^{-9}$ second to about 1 second, about 1 second to about 1 minute, or about 1 minute to about 1 hour. In some embodiments, the cell is deformed for between any one of about $1.0\times10^{-9}$ to about $1.0\times10^{-1}$, about $1.0\times10^{-9}$ to about $1.0\times10^{-2}$, about $1.0\times10^{-9}$ to about $1.0\times10^{-3}$, about $1.0\times10^{-9}$ to about $1.0\times10^{-4}$, about $1.0\times10^{-9}$ to about $1.0\times10^{-5}$, about $1.0\times10^{-9}$ to about $1.0\times10^{-6}$, about $1.0\times10^{-9}$ to about $1.0\times10^{-7}$, or about $1.0\times10^{-9}$ to about $1.0\times10^{-8}$ seconds. In some embodiment, the cell is deformed for any one of about $1.0\times10^{-8}$ to about $1.0\times10^{-1}$, about $1.0\times10^{-7}$ to about $1.0\times10^{-1}$, about $1.0\times10^{-6}$ to about $1.0\times10^{-1}$, about $1.0\times10^{-5}$ to about $1.0\times10^{-1}$, about $1.0\times10^{-4}$ to about $1.0\times10^{-1}$, about $1.0\times10^{-3}$ to about $1.0\times10^{-1}$, or about $1.0\times10^{-2}$ to about $1.0\times10^{-1}$ seconds. In some embodiments, deforming the cell includes deforming the cell for a time ranging from, without limitation, about 1 μs to at least about 750 μs, e.g., at least about 1 μs, 10 μs, 50 μs, 100 μs, 500 μs, or 750 μs.

In some embodiments, the passage of the compound into the cell occurs simultaneously with the cell passing through the constriction and/or the perturbation of the cell. In some embodiments, passage of the compound into the cell occurs after the cell passes through the constriction. In some embodiments, passage of the compound into the cell occurs on the order of minutes after the cell passes through the constriction. In some embodiments, the passage of the compound into the cell occurs from about $1.0\times10^{-2}$ seconds to at least about 30 minutes after the cell passes through the constriction. For example, the passage of the compound into the cell occurs from about $1.0\times10^{-2}$ seconds to about 1 second, about 1 second to about 1 minute, or about 1 minute to about 30 minutes after the cell passes through the constriction. In some embodiments, the passage of the compound into the cell occurs about $1.0\times10^{-2}$ seconds to about 10 minutes, about $1.0\times10^{-2}$ seconds to about 5 minutes, about $1.0\times10^{-2}$ seconds to about 1 minute, about $1.0\times10^{-2}$ seconds to about 50 seconds, about $1.0\times10^{-2}$ seconds to about 10 seconds, about $1.0\times10^{-2}$ seconds to about 1 second, or about $1.0\times10^{-2}$ seconds to about 0.1 second after the cell passes through the constriction. In some embodiments, the passage of the compound into the cell occurs about $1.0\times10^{-1}$ seconds to about 10 minutes, about 1 second to about 10 minutes, about 10 seconds to about 10 minute, about 50 seconds to about 10 minutes, about 1 minute to about 10 minutes, or about 5 minutes to about 10 minutes after the cell passes through the constriction. In some embodiments, a perturbation in the cell after it passes through the constriction is corrected within the order of about five minutes after the cell passes through the constriction.

In some embodiments, the cell viability after passing through a constriction is about 5% to about 100%. In some embodiments, the cell viability after passing through the constriction is at least about 5%, 10%, 20%, 30%, 40%, 50%, 60%, 70%, 75%, 80%, 85%, 90%, 95%, or 99%. In some embodiments, the cell viability is measured from about $1.0\times10^{-2}$ seconds to at least about 10 days after the cell passes through the constriction. For example, the cell viability is measured from about $1.0\times10^{-2}$ seconds to about 1 second, about 1 second to about 1 minute, about 1 minute to about 30 minutes, or about 30 minutes to about 2 hours after the cell passes through the constriction. In some embodiments, the cell viability is measured about $1.0\times10^{-2}$ seconds to about 2 hours, about $1.0\times10^{-2}$ seconds to about 1 hour, about $1.0\times10^{-2}$ seconds to about 30 minutes, about $1.0\times10^{-2}$ seconds to about 1 minute, about $1.0\times10^{-2}$ seconds to about 30 seconds, about $1.0\times10^{-2}$ seconds to about 1 second, or about $1.0\times10^{-2}$ seconds to about 0.1 second after the cell passes through the constriction. In some embodiments, the cell viability is measured about 1.5 hours to about 2 hours, about 1 hour to about 2 hours, about 30 minutes to about 2 hours, about 15 minutes to about 2 hours, about 1 minute to about 2 hours, about 30 seconds to about 2 hours, or about 1 second to about 2 hours after the cell passes through the constriction. In some embodiments, the cell viability is measured about 2 hours to about 5 hours, about 5 hours to about 12 hours, about 12 hours to about 24 hours, or about 24 hours to about 10 days after the cell passes through the constriction.

VII. Delivery Parameters

A number of parameters may influence the delivery of a compound to a cell for suppressing an immune response or inducing tolerance by the methods described herein. In some embodiments, the cell suspension is contacted with the compound before, concurrently, or after passing through the constriction. The cell may pass through the constriction suspended in a solution that includes the compound to deliver, although the compound can be added to the cell suspension after the cells pass through the constriction. In some embodiments, the compound to be delivered is coated on the constriction.

Examples of parameters that may influence the delivery of the compound into the cell include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, and the amount of time that the cell recovers or incubates after passing through the constrictions can affect the passage of the delivered compound into the cell. Additional parameters influencing the delivery of the compound into the cell can include the velocity of the cell in the constriction, the shear rate in the constriction, the viscosity of the cell suspension, the velocity component that is perpendicular to flow velocity, and time in the constriction. Such parameters can be designed to control delivery of the compound. In some embodiments, the cell concentration ranges from about 10 to at least about $10^{12}$ cells/ml or any concentration or range of concentrations therebetween. In some embodiments, delivery compound concentrations can range from about 10 ng/ml to about 1 g/mL or any concentration or range of concentrations therebetween. In some embodiments, delivery compound concentrations can range from about 1 pM to at least about 2M or any concentration or range of concentrations therebetween. The composition of the cell suspension (e.g., osmolarity, salt concentration, serum content, cell concentration. pH, etc.) can impact delivery of the compound for suppressing an immune response or inducing tolerance. In some embodiments, the aqueous solution is iso-osmolar or iso-tonic.

The temperature used in the methods of the present disclosure can be adjusted to affect compound delivery and cell viability. In some embodiments, the method is performed between about −5° C. and about 45° C. For example, the methods can be carried out at room temperature (e.g., about 20° C.), physiological temperature (e.g., about 37° C.), higher than physiological temperature (e.g., greater than about 37° C. to 45° C. or more), or reduced temperature (e.g., about −5° C. to about 4° C.), or temperatures between these exemplary temperatures.

Various methods can be utilized to drive the cells through the constrictions. For example, pressure can be applied by a pump on the entrance side (e.g., gas cylinder, or compressor), a vacuum can be applied by a vacuum pump on the exit side, capillary action can be applied through a tube, and/or the system can be gravity fed. Displacement based flow systems can also be used (e.g., syringe pump, peristaltic pump, manual syringe or pipette, pistons, etc.). In some embodiments, the cells are passed through the constrictions by positive pressure or negative pressure. In some embodiments, the cells are passed through the constrictions by constant pressure or variable pressure. In some embodiments, pressure is applied using a syringe. In some embodiments, pressure is applied using a pump. In some embodiments, the pump is a peristaltic pump or a diaphragm pump. In some embodiments, pressure is applied using a vacuum. In some embodiments, the cells are passed through the constrictions by g-force. In some embodiments, the cells are passed through the constrictions by centrifugal force. In some embodiments, the cells are passed through the constrictions by capillary pressure.

In some embodiments, fluid flow directs the cells through the constrictions. In some embodiments, the fluid flow is turbulent flow prior to the cells passing through the constriction. Turbulent flow is a fluid flow in which the velocity at a given point varies erratically in magnitude and direction. In some embodiments, the fluid flow through the constriction is laminar flow. Laminar flow involves uninterrupted flow in a fluid near a solid boundary in which the direction of flow at every point remains constant. In some embodiments, the fluid flow is turbulent flow after the cells pass through the constriction. The velocity at which the cells pass through the constrictions can be varied. In some embodiments, the cells pass through the constrictions at a uniform cell speed. In some embodiments, the cells pass through the constrictions at a fluctuating cell speed.

In other embodiments, a combination treatment is used to suppress an immune response or induce tolerance by passing a cell suspension through a constriction, wherein the constriction deforms the anucleate cell thereby causing a perturbation of the cell such that an antigen or compound enters the cell, e.g., the methods described herein followed by exposure to an electric field downstream of the constriction. In some embodiments, the cell is passed through an electric field generated by at least one electrode after passing through the constriction. In some embodiments, the electric field assists in delivery of compounds to a second location inside the cell. For example, the combination of a cell-deforming constriction and an electric field delivers a plasmid encoding an antibody into the cell, resulting in the de novo production of antibody. In some embodiments, one or more electrodes are in proximity to the cell-deforming constriction to generate an electric field. In some embodiments, the electric field is between about 0.1 kV/m to about 100 MV/m, or any number or range of numbers therebetween. In some embodiments, an integrated circuit is used to provide an electrical signal to drive the electrodes. In some embodiments, the cells are exposed to the electric field for a pulse width of between about Ins to about Is and a period of between about 100 ns to about 10 s or any time or range of times therebetween.

VIII. Cell Suspensions for Delivery to Anucleate Cells

The cell suspension may be a mixed or purified population of cells. In some embodiments, the cell suspension is a mixed cell population, such as whole blood. In some embodiments, the cell suspension is a purified cell population, such as a purified population of anucleate cells.

The composition of the cell suspension (e.g., osmolarity, salt concentration, serum content, cell concentration, pH, etc.) can impact delivery of the compound for suppressing an immune response or inducing tolerance. In some embodiments, the suspension comprises whole blood. Alternatively, the cell suspension is a mixture of cells in a physiological saline solution or physiological medium other than blood. In some embodiments, the cell suspension comprises an aqueous solution. In some embodiments, the aqueous solution comprises cell culture medium, PBS, salts, sugars, growth factors, animal derived products, bulking materials, surfactants, lubricants, vitamins, amino acids, proteins, cell cycle inhibitors, and/or an agent that impacts actin polymerization. In some embodiments, the cell culture medium is DMEM, Opti-MEM™. IMDM, or RPMI. Additionally, solution buffer can include one or more lubricants (pluronics or other surfactants) that can be designed, for example, to reduce or eliminate clogging of the surface and improve cell viability. Exemplary surfactants include, without limitation, poloxamer, polysorbates, sugars or sugar alcohols such as mannitol, sorbitol, animal derived serum, and albumin protein. In some embodiments, the aqueous solution is iso-osmolar or iso-tonic. In some embodiments, the aqueous solution includes plasma.

In some configurations with certain types of cells, the cells can be incubated in one or more solutions that aid in the delivery of the compound to the interior of the cell. In some embodiments, the aqueous solution comprises an agent that impacts actin polymerization. In some embodiments, the agent that impacts actin polymerization is Latrunculin A. Cytochalasin, and/or Colchicine. For example, the cells can be incubated in a depolymerization solution such as Lantrunculin A (0.1 μg/ml) for 1 hour prior to delivery to depolymerize the actin cytoskeleton. As an additional example, the cells can be incubated in 10 μM Colchicine (Sigma) for 2 hours prior to delivery to depolymerize the microtubule network.

In some embodiments, the cell population is enriched prior to use in the disclosed methods. For example, cells are obtained from a bodily fluid. e.g., peripheral blood, and optionally enriched or purified to concentrate B cells. Cells may be enriched by any methods known in the art, including without limitation, magnetic cell separation, fluorescent activated cell sorting (FACS), or density gradient centrifugation.

The viscosity of the cell suspension can also impact the methods disclosed herein. In some embodiments, the viscosity of the cell suspension ranges from about $8.9\times10^{-4}$ Pa·s to about $4.0\times10^{-3}$ Pa·s or any value or range of values therebetween. In some embodiments, the viscosity ranges between any one of about $8.9\times10^{-4}$ Pas to about $4.0\times10^{-3}$ Pa·s, about $8.9\times10^{-4}$ Pa·s to about $3.0\times10^{-3}$ Pa·s, about $8.9\times10^{-4}$ Pa·s to about $2.0\times10^{-3}$ Pa·s, or about $8.9\times10^{-3}$ Pa·s to about $1.0\times10^{-3}$ Pa·s. In some embodiments, the viscosity ranges between any one of about 0.89 cP to about 4.0 cP, about 0.89 cP to about 3.0 cP, about 0.89 cP to about 2.0 cP, or about 0.89 cP to about 1.0 cP. In some embodiments, a shear thinning effect is observed, in which the viscosity of the cell suspension decreases under conditions of shear strain. Viscosity can be measured by any method known in the art, including without limitation, viscometers, such as a glass capillary viscometer, or rheometers. A viscometer measures viscosity under one flow condition, while a rheometer is used to measure viscosities which vary with flow conditions. In some embodiments, the viscosity is measured for a shear thinning solution such as blood. In some embodiments, the viscosity is measured between about −5° C. and about 45° C. For example, the viscosity is measured at room temperature (e.g., about 20° C.), physiological temperature (e.g., about 37° C.), higher than physiological temperature (e.g., greater than about 37° C. to 45° C. or more), reduced temperature (e.g., about −5° C. to about 4° C.), or temperatures between these exemplary temperatures.

IX. Antigens and Tolerogenic Factors to Suppress an Immune Response or Induce Tolerance In some embodiments the invention provides delivery of antigens to suppress an immune response or induce tolerance, wherein the antigen is delivered to the cell by any of the methods described herein. In some embodiments, the antigen is a single antigen. In some embodiments, the antigen is a mixture of antigens. An antigen is a substance that stimulates a specific immune response, such as a cell or antibody-mediated immune response. Antigens bind to receptors expressed by immune cells, such as T cell receptors (TCRs), which are specific to a particular antigen. Antigen-receptor binding subsequently triggers intracellular signaling pathways that lead to downstream immune effector pathways, such as cell activation, cytokine production, cell migration, cytotoxic factor secretion, cell apoptosis, and antibody production.

In some embodiments, the antigen is a protein or polypeptide antigen. In some embodiments, the compound comprises a disease-associated antigen. In some embodiments, antigens are derived from foreign sources, such as bacteria, fungi, viruses, or allergens. In some embodiments, antigens are derived from internal sources, such as self-proteins (i.e. self-antigens). In some embodiments, the antigen is in a cell lysate. Self-antigens are antigens present on or in an organism's own cells. Self-antigens do not normally stimulate an immune response, but may in the context of autoimmune diseases, such as Type I Diabetes or Rheumatoid Arthritis. In some embodiments, the antigen is a therapeutic agent. In some embodiments, the antigen is a therapeutic polypeptide, or a fragment of a therapeutic polypeptide. In some embodiments, the therapeutic agent is conjugated to a carbohydrate. In some embodiments, the therapeutic agent is a clotting factor. Exemplary clotting factors include, without limitation, Factor VIII and Factor IX. For example, the antigen may be a Factor VIII protein used in the treatment of hemophilia. In some embodiments, the therapeutic agent is an antibody. Exemplary therapeutic antibodies include, without limitation, anti-TNFα, anti-VEGF, anti-CD3, anti-CD20, anti-IL-2R, anti-Her2, anti-RSVF, anti-CEA, anti-IL-1beta, anti-CD15, anti-myosin, anti-PSMA, anti-40 kDa glycoprotein, anti-CD33, anti-CD52, anti-IgE, anti-CD11a, anti-EGFR, anti-C5, anti-alpha-4 integrin, anti-IL-12/IL-23, anti-IL-6R, and anti-RANKL. In some embodiments, the therapeutic agent is a growth factor. Exemplary therapeutic growth factors include, without limitation, Erythropoietin (EPO) and megakaryocyte differentiation and growth factor (MDGF). In some embodiments, the therapeutic agent is a hormone. Exemplary therapeutic hormones include, without limitation, insulin, human growth hormone, and follicle stimulating hormone. In some embodiments, the therapeutic agent is a recombinant cytokine. Exemplary therapeutic recombinant cytokines include, without limitation, IFNβ, IFNα, and GM-CSF.

In some embodiments, the antigen is an allograft transplantation antigen. An allograft transplant is a transfer of cells, tissues, or organs, to a recipient from a genetically non-identical donor of the same species. In some embodiments, the antigen is a modified antigen. For example, antigens may be fused with therapeutic agents or targeting peptides. In some embodiments, the modified antigen is fused with a polypeptide. In some embodiments, the modified antigen is fused with a lipid. In some embodiments, the antigen is fused with a carbohydrate. In some embodiments, the antigen is a non-protein antigen, such as a lipid, glycolipid, or polysaccharide. In some embodiments, the antigen is a whole microorganism, such as an intact bacterium.

In some embodiments, the antigen is associated with a virus. In some embodiments, the antigen is a viral antigen. Exemplary viral antigens include SARS-CoV antigens and influenza antigens. In some embodiments, the compound comprises cell lysate from tissue infected with an unknown pathogen. In some embodiments, the antigen is a therapeutic vehicle. In some embodiments, the therapeutic vehicle is a virus, such as an adenovirus, adeno-associated virus, baculovirus, herpes virus, or retrovirus used for gene therapy. In some embodiments, the therapeutic vehicle is a liposome. In some embodiments, the therapeutic vehicle is a nanoparticle.

In some embodiments, the antigen is associated with a microorganism; for example a bacterium. In some embodiments, the suppressed immune response and/or induced tolerance comprises a decreased pathogenic immune response or induced tolerance to the microorganism; for example, a bacterium. In some embodiments, the microorganism is part of the microbiome of the individual. In some embodiments, the microorganism may benefit the microbiome of the individual.

In certain aspects, the invention provides methods for delivering an antigen into an anucleate cell, the method comprising passing a cell suspension comprising the anucleate cell through a constriction, wherein said constriction deforms the anucleate cell, thereby causing a perturbation of the cell such that the antigen enters the cell, wherein said cell suspension is contacted with the antigen. In some embodiments, presentation of the antigen in a tolerogenic environment suppresses an immune response to the antigen. In some embodiments, presentation of said antigen in a tolerogenic environment induces tolerance to the antigen. In some embodiments, the antigen is delivered to the anucleate cell in vitro, ex vivo, or in vivo.

In some embodiments the invention provides delivery of tolerogenic factors to suppress an immune response or induce tolerance, wherein the tolerogenic factor is delivered to the cell by any of the methods described herein. In some embodiments, the tolerogenic factor enhances suppression of an immune response to an antigen and/or enhances the induction of tolerance to an antigen. For example, the tolerogenic factor may promote tolerogenic presentation of the antigen by an antigen-presenting cell. In some embodiments, the tolerogenic factor is introduced simultaneously with the antigen. In some embodiments, the tolerogenic factor and antigen are introduced sequentially. In some embodiments, the tolerogenic factor comprises a polypeptide. In some embodiments, the polypeptide is IL-4, IL-10, IL-13. IL-35, IFNα, or TGFβ. In some embodiments, the polypeptide is a therapeutic polypeptide. In some embodiments, the polypeptide is a fragment of a therapeutic polypeptide. In some embodiments, the polypeptide is conjugated to a carbohydrate. In some embodiments, the tolerogenic factor is a nucleic acid. In some embodiments, the nucleic acid can include, without limitation, mRNA. DNA, miRNA, or siRNA. For example, the tolerogenic factor can include siRNA to knock down expression of inflammatory genes. In some embodiments, the tolerogenic factor is a DNA sequence that binds NFκB and prevents NFκB activation and downstream signaling. In some embodiments, the tolerogenic factor is a small molecule.

In some embodiments, the tolerogenic factor modulates expression and/or activity of an immunomodulatory agent (such as an immunostimulatory agent (e.g., a costimulatory molecule), an immunosuppressive agent, or an inflammatory or anti-inflammatory molecule). In some embodiments, the tolerogenic factor inhibits expression and/or activity of an immunostimulatory agent (e.g., a costimulatory molecule), enhances expression and/or activity of an immunosuppressive molecule, inhibits expression and/or activity of an inflammatory molecule, and/or enhances expression and/or activity of an anti-inflammatory molecule. In some embodiments, the tolerogenic factor inhibits the activity of a costimulatory molecule. Interaction between costimulatory molecules and their ligands is important to sustain and integrate TCR signaling to stimulate optimal T cell proliferation and differentiation. In some embodiments, the tolerogenic factor decreases expression of a costimulatory molecule. Exemplary costimulatory molecules expressed on antigen-presenting cells include, without limitation, CD40. CD80, CD86. CD54, CD83. CD79, or ICOS Ligand. In some embodiments, the costimulatory molecule is CD80 or CD86. In some embodiments, the tolerogenic factor inhibits the expression of a nucleic acid that expresses or modulates expression of the costimulatory molecule. In some embodiments, the tolerogenic factor deletes a nucleic acid that expresses or modulates expression of the costimulatory molecule. In some embodiments, deletion of the nucleic acid that expresses or modulates expression of the costimulatory molecule is achieved via gene editing. In some embodiments, the tolerogenic factor inhibits the costimulatory molecule. In some embodiments, the tolerogenic factor is a siRNA that inhibits the costimulatory molecule. In some embodiments, the tolerogenic factor increases the activity of a transcriptional regulator that suppresses expression of the costimulatory molecule. In some embodiments, the tolerogenic factor increases the activity of a protein inhibitor that suppresses expression of the costimulatory molecule. In some embodiments, the tolerogenic factor comprises nucleic acid encoding a suppressor of the costimulatory molecule. In some embodiments, the tolerogenic factor degrades the costimulatory molecule. In some embodiments, the tolerogenic factor labels the costimulatory molecule for destruction. For example, the tolerogenic factor may enhance ubiquitination of the costimulatory molecule, thereby targeting it for destruction.

In some embodiments, the tolerogenic factor enhances the expression and/or activity of an immunosuppressive molecule. In some embodiments, the immunosuppressive molecule is a co-inhibitory molecule, a transcriptional regulator, or an immunosuppressive molecule. Co-inhibitory molecules negatively regulate the activation of lymphocytes. Exemplary co-inhibitory molecules include, without limitation, PD-L1. PD-L2, HVEM. B7-H3, TRAIL, immunoglobulin-like transcripts (ILT) receptors (ILT2, ILT3, ILT4), FasL, CTLA4, CD39, CD73, and B7-H4. In some embodiments, the co-inhibitory molecule is PD-L1 or PD-L2. In some embodiments, the tolerogenic factor increases the activity of the co-inhibitory molecule. In some embodiments, the tolerogenic factor increases expression of a co-inhibitory molecule. In some embodiments, the tolerogenic factor encodes the co-inhibitory molecule. In some embodiments, the tolerogenic factor increases the activity of the co-inhibitory molecule. In some embodiments, the tolerogenic factor increases the activity of a transcriptional regulator that enhances expression of the co-inhibitory molecule. In some embodiments, the tolerogenic factor increases the activity of a polypeptide that increases expression of the co-inhibitory molecule. In some embodiments, the tolerogenic factor comprises nucleic acid encoding an enhancer of the co-inhibitory molecule. In some embodiments, the tolerogenic factor inhibits an inhibitor of a co-inhibitory molecule.

In some embodiments, the tolerogenic factor increases expression and/or activity of an immunosuppressive molecule. Exemplary immunosuppressive molecules include, without limitation, arginase-1 (ARG1), indoleamine 2,3-dioxygenase (IDO), Prostaglandin E2 (PGE2), inducible nitric-oxide synthase (iNOS), nitric oxide (NO), nitric-oxide synthase 2 (NOS2), thymic stromal lymphopoietin (TSLP), vascular intestinal peptide (VIP), hepatocyte growth factor (HGF), transforming growth factor beta (TGFβ). IFNα. IL-4. IL-10, IL-13, and IL-35. In some embodiments, the immunosuppressive molecule is NO or IDO. In some embodiments, the tolerogenic factor encodes the immunosuppressive molecule. In some embodiments, the tolerogenic factor increases the activity of the immunosuppressive molecule. In some embodiments, the tolerogenic factor increases the activity of a transcriptional regulator that enhances expression of the immunosuppressive molecule. In some embodiments, the tolerogenic factor increases the activity of a polypeptide that enhances expression of the immunosuppressive molecule. In some embodiments, the tolerogenic factor comprises nucleic acid encoding an enhancer of the immunosuppressive molecule. In some embodiments, the tolerogenic factor inhibits a negative regulator of an immunosuppressive molecule.

In some embodiments, the tolerogenic factor inhibits expression and/or activity of an inflammatory molecule. In some embodiments, the inflammatory molecule is an inflammatory transcription factor. In some embodiments, the tolerogenic factor inhibits the inflammatory transcription factor. In some embodiments, the tolerogenic factor decreases expression of an inflammatory transcription factor. In some embodiments, the inflammatory transcription factor is NFκB, an interferon regulatory factor (IRF), or a molecule associated with the JAK-STAT signaling pathway. The NF-κB pathway is a prototypical proinflammatory signaling pathway that mediates the expression of proinflammatory genes including cytokines, chemokines, and adhesion molecules. Interferon regulatory factors (IRFs) constitute a family of transcription factors that can regulate the expression of proinflammatory genes. The JAK-STAT signaling pathway transmits information from extracellular cytokine signals to the nucleus, resulting in DNA transcription and expression of genes involved in immune cell proliferation and differentiation. The JAK-STAT system consists of a cell surface receptor. Janus kinases (JAKs), and Signal Transducer and Activator of Transcription (STAT) proteins. Exemplary JAK-STAT molecules include, without limitation, JAK1, JAK2, JAK 3, Tyk2, STAT1, STAT2, STAT3, STAT4, STAT5 (STAT5A and STAT5B), and STAT6. In some embodiments, the tolerogenic factor enhances expression of a suppressor of cytokine signaling (SOCS) protein. SOCS proteins may inhibit signaling through the JAK-STAT pathway. In some embodiments, the tolerogenic factor inhibits the expression of a nucleic acid encoding the inflammatory transcription factor. In some embodiments, the tolerogenic factor deletes a nucleic acid encoding the inflammatory transcription factor. In some embodiments, the tolerogenic factor increases the activity of a transcriptional regulator that suppresses expression of the inflammatory transcription factor. In some embodiments, the tolerogenic factor increases the activity of a protein inhibitor that suppresses expression of the inflammatory transcription factor. In some embodiments, the tolerogenic factor comprises nucleic acid encoding a suppressor of the inflammatory transcription factor.

In some embodiments, the tolerogenic factor enhances expression and/or activity of an anti-inflammatory molecule. In some embodiments, the anti-inflammatory molecule is an anti-inflammatory transcription factor. In some embodiments, the tolerogenic factor enhances the anti-inflammatory transcription factor. In some embodiments, the tolerogenic factor increases expression of an anti-inflammatory transcription factor. In some embodiments, the tolerogenic factor enhances expression of nucleic acid encoding the anti-inflammatory transcription factor. In some embodiments, the tolerogenic factor decreases the activity of a transcriptional regulator that suppresses expression of the anti-inflammatory transcription factor. In some embodiments, the tolerogenic factor decreases the activity of a protein inhibitor that suppresses expression of the anti-inflammatory transcription factor. In some embodiments, the tolerogenic factor comprises nucleic acid encoding an enhancer of the anti-inflammatory transcription factor.

In certain aspects, the invention provides methods for delivering a tolerogenic factor into an anucleate cell, the method comprising passing a cell suspension comprising the anucleate cell through a constriction, wherein said constriction deforms the anucleate cell, thereby causing a perturbation of the cell such that the tolerogenic factor enters the cell, wherein said cell suspension is contacted with the tolerogenic factor. In some embodiments, the tolerogenic factor is delivered to the anucleate cell in vitro, ex vivo, or in vivo.

In some embodiments, the tolerogenic factor comprises a nucleic acid. In some embodiments, the tolerogenic factor is a nucleic acid. Exemplary nucleic acids include, without limitation, recombinant nucleic acids, DNA, recombinant DNA, cDNA, genomic DNA. RNA, siRNA, mRNA, saRNA, miRNA, lncRNA, tRNA, guide RNA, and shRNA. In some embodiments, the nucleic acid is homologous to a nucleic acid in the cell. In some embodiments, the nucleic acid is heterologous to a nucleic acid in the cell. In some embodiments, the tolerogenic factor is a plasmid. In some embodiments, the nucleic acid is a therapeutic nucleic acid. In some embodiments, the nucleic acid encodes a therapeutic polypeptide. In some embodiments, the tolerogenic factor comprises a nucleic acid encoding siRNA, mRNA, miRNA, lncRNA, tRNA, or shRNA. For example, the tolerogenic factor can include siRNA to knock down expression of inflammatory genes. In some embodiments, the tolerogenic factor is a DNA sequence that binds NFκB and prevents NFκB activation and downstream signaling.

In some embodiments, the tolerogenic factor comprises a polypeptide. In some embodiments, the tolerogenic factor is a polypeptide. In some embodiments, the protein or polypeptide is a therapeutic protein, antibody, fusion protein, antigen, synthetic protein, reporter marker, or selectable marker. In some embodiments, the protein is a gene-editing protein or nuclease such as a zinc-finger nuclease (ZFN), transcription activator-like effector nuclease (TALEN), mega nuclease, CRE recombinase, transposase, RNA-guided endonuclease (e.g., CAS9 enzyme), DNA-guided endonuclease, or integrase enzyme. In some embodiments, the fusion proteins can include, without limitation, chimeric protein drugs such as antibody drug conjugates or recombinant fusion proteins such as proteins tagged with GST or streptavidin. In some embodiments, the compound is a transcription factor. Exemplary transcription factors include, without limitation, Oct5, Sox2, c-Myc, Klf-4, T-bet, GATA3, FoxP3, and RORγt. In some embodiments, the polypeptide is IL-4, IL-10, IL-13, IL-35, IFNα, or TGFβ. In some embodiments, the polypeptide is a therapeutic polypeptide. In some embodiments, the polypeptide is a fragment of a therapeutic polypeptide. In some embodiments, the polypeptide is a peptide nucleic acid (PNA).

In some embodiments, the tolerogenic factor comprises a protein-nucleic acid complex. In some embodiments, the tolerogenic factor is a protein-nucleic acid complex. In some embodiments, protein-nucleic acid complexes, such as clustered regularly interspaced short palindromic repeats (CRISPR)-Cas9, are used in genome editing applications. These complexes contain sequence-specific DNA-binding domains in combination with nonspecific DNA cleavage nucleases. These complexes enable targeted genome editing, including adding, disrupting, or changing the sequence of a specific gene. In some embodiments, a disabled CRISPR is used to block or induce transcription of a target gene. In some embodiments, the tolerogenic factor contains a Cas9 protein and a guide RNA or donor DNA. In some embodiments, the tolerogenic factor includes a nucleic acid encoding for a Cas9 protein and a guide RNA or donor DNA. In some embodiments, the gene editing complex targets expression of a costimulatory molecule (e.g., CD80 and/or CD86).

In some embodiments, the tolerogenic factor comprises a chimeric antigen receptor (CAR). In some embodiments, the tolerogenic factor is a chimeric antigen receptor (CAR). In some embodiments, the CAR is a fusion of an extracellular recognition domain (e.g., an antigen-binding domain), a transmembrane domain, and one or more intracellular signaling domains. Upon antigen engagement, the intracellular signaling portion of the CAR can initiate an immunosuppression or tolerogenic-related response in an immune cell. In some embodiments, the CAR is a chimeric T cell antigen receptor. In some embodiments, the CAR antigen-binding domain is a single-chain antibody variable fragment (scFv). In some embodiments, the tolerogenic factor encodes a modified TCR containing cytoplasmic signaling domains that trigger production of immunosuppressive cytokines upon binding to antigen. In some embodiments, the tolerogenic factor encodes a chimeric antigen receptor containing cytoplasmic signaling domains that trigger production of immunosuppressive cytokines upon binding to antigen.

In some embodiments, the tolerogenic factor comprises a small molecule. In some embodiments, the tolerogenic factor is a small molecule. In some embodiments, the small molecule inhibits the activity of a costimulatory molecule, enhances the activity of a co-inhibitory molecule, and/or inhibits the activity of an inflammatory molecule. Exemplary small molecules include, without limitation, pharmaceutical agents, metabolites, or radionuclides. In some embodiments, the pharmaceutical agent is a therapeutic drug and/or cytotoxic agent. In some embodiments, the compound comprises a nanoparticle. Examples of nanoparticles include gold nanoparticles, quantum dots, carbon nanotubes, nanoshells, dendrimers, and liposomes. In some embodiments, the nanoparticle contains or is linked (covalently or noncovalently) to a therapeutic molecule. In some embodiments, the nanoparticle contains a nucleic acid, such as mRNA or cDNA.

In some embodiments, the compound to deliver is purified. In some embodiments, the compound is at least about 60% by weight (dry weight) the compound of interest. In some embodiments, the purified compound is at least about 75%, 90%, or 99% the compound of interest. In some embodiments, the purified compound is at least about 90%, 91%, 92%, 93%, 94%, 95%, 98%, 99%, or 100% (w/w) the compound of interest. Purity is determined by any known methods, including, without limitation, column chromatography, thin layer chromatography, HPLC analysis. NMR, mass spectrometry, or SDS-PAGE. Purified DNA or RNA is defined as DNA or RNA that is free of exogenous nucleic acids, carbohydrates, and lipids.

In some embodiments, the compound is an intermediate compound. The intermediate compound may be a molecular entity that is formed from preceding intermediates and reacts further to give the final reaction product. In some embodiments, the intermediate compound is a protein precursor, or pro-protein, that is cleaved by an enzyme to produce the mature, functional form of the protein. In some embodiments, the intermediate compound is an inactive enzyme precursor, or zymogen, that requires modification or cleavage to produce the active enzyme.

X. Applications

In some aspects, the invention provides methods of treating a patient by introducing an anucleate cell, modified by passing through a constriction such that a compound enters the cell, to the patient. In some embodiments, the treatment comprises multiple (such as any of 2, 3, 4, 5, 6, or more) steps of introducing such modified anucleate cells to the patient. In some embodiments, the cell is isolated from a patient, modified according to the methods disclosed, and introduced back into the patient. For example, a population of anucleate cells is isolated from a patient, passed through the constriction to achieve delivery of a compound, and then re-infused into the patient to augment a therapeutic immune response. In some embodiments, the cell is isolated from an individual, modified according to the disclosed methods, and introduced back into the individual. For example, a population of anucleate cells is isolated from an individual, passed through the constriction to achieve delivery of a compound, and then re-infused into the patient to suppress an immune response or induce tolerance in the individual.

In some embodiments, an anucleate cell is isolated from a universal blood donor (e.g. an O-blood donor) and then stored and/or frozen for later constriction-mediated delivery and introduction into an individual. In some embodiments, an antigen is isolated from an individual, delivered to an anucleate cell isolated from a universal donor, and introduction into the individual. In some embodiments, an anucleate cell is isolated from a blood donor and then stored and/or frozen for later constriction mediated delivery and introduction into an individual with a matched blood type to the blood donor. In some embodiments, an antigen is isolated from an individual, delivered to an anucleate cell isolated from a blood donor, and introduction into the individual.

In some embodiments, the invention provides methods of treating an individual by introducing the cell, modified by passing through a constriction such that a compound enters the cell, to the individual. In some embodiments, the cell is an autologous cell. For example, the anucleate cell is isolated from an individual (e.g., a patient), modified according to the methods disclosed, and introduced back into the individual. In some embodiments, the cell is isolated from an individual, modified according to the disclosed methods, and introduced back into the same individual. In some embodiments, the cell is an allogeneic cell. For example, the cell is isolated from a different individual, modified according to the methods disclosed, and introduced into the first individual (e.g., the patient). In some embodiments, a pool of cells from multiple individuals is modified according to the methods disclosed, and introduced into the first individual (e.g., the patient). In some embodiments, the cell is isolated from an individual, modified according to the disclosed methods, and introduced into a different individual. In some embodiments, a population of cells is isolated from an individual (the patient) or different individual, passed through the constriction to achieve delivery of a compound, and then re-infused into the patient to augment a therapeutic response.

In some embodiments, the treatment comprises multiple (such as any of 2, 3, 4, 5, 6, or more) steps of administering modified anucleate cells as described herein to the individual. For example, in some embodiments, there is provided a method of treating an individual by administering a cell, modified by passing through a constriction such that a compound enters the cell, to the individual 2, 3, 4, 5, 6, or more times. In some embodiments, the duration of time between any two consecutive administrations of the cell is at least about 1 day (such at least about any of 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, or longer, including any ranges between these values).

Any of the methods described above are carried out in vitro, ex vivo, or in vivo. For in vivo applications, the device may be implanted in a vascular lumen, e.g., an in-line stent in an artery or vein. In some embodiments, the methods are used as part of a bedside system for ex vivo treatment of patient cells and immediate reintroduction of the cells into the patient. Such methods could be employed as a means of suppressing an immune response or inducing tolerance in an individual. In some embodiments, the method can be implemented in a typical hospital laboratory with a minimally trained technician. In some embodiments, a patient operated treatment system can be used. In some embodiments, the method is implemented using an in-line blood treatment system, in which blood is directly diverted from a patient, passed through the constriction, resulting in compound delivery to blood cells, and directly transfused back into the patient after treatment.

XI. Systems and Kits

In some aspects, the invention provides a system comprising the constriction, cell suspension, and compound for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to anucleate cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in delivering a compound to suppress an immune response or induce tolerance. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present disclosure also provides kits comprising components of the methods described herein and may further comprise instruction(s) for performing said methods to suppress an immune response or induce tolerance. The kits described herein may further include other materials, including other buffers, diluents, filters, needles, syringes, and package inserts with instructions for performing any methods described herein; e.g., instructions for suppressing an immune response or inducing tolerance.

XII. Exemplary Embodiments

Embodiment 1

A method for suppressing an immune response in an individual, the method comprising:

a. passing a cell suspension comprising an anucleate cell through a constriction, wherein said constriction deforms the cell thereby causing a perturbation of the cell such that an antigen enters the anucleate cell; and
b. introducing the anucleate cell into the individual.

wherein said antigen is processed in a tolerogenic environment, wherein presentation of said antigen in said tolerogenic environment suppresses an immune response to the antigen.

Embodiment 2

A method for suppressing an immune response in an individual, the method comprising:

a. passing a cell suspension comprising an anucleate cell through a constriction, wherein said constriction deforms the cell thereby causing a perturbation of the cell such that a tolerogenic factor enters the anucleate cell; and
b. introducing the anucleate cell into the individual, wherein said tolerogenic factor contributes to a tolerogenic environment that suppresses an immune response.

Embodiment 3

A method for suppressing an immune response in an individual, the method comprising:

a. passing a cell suspension comprising an anucleate cell through a constriction, wherein said constriction deforms the cell thereby causing a perturbation of the cell such that an antigen and a tolerogenic factor enters the anucleate cell; and
b. introducing the anucleate cell into the individual, wherein said antigen is processed in a tolerogenic environment, and wherein presentation of said antigen in said tolerogenic environment suppresses an immune response to the antigen.

Embodiment 4

A method for suppressing an immune response in an individual, comprising:

a. passing a first cell suspension comprising a first anucleate cell through a constriction, wherein said constriction deforms the cell thereby causing a perturbation of the cell such that an antigen enters the anucleate cell,
b. passing a second cell suspension comprising a second anucleate cell through a constriction, wherein said constriction deforms the cell thereby causing a perturbation of the cell such that a tolerogenic factor enters the anucleate cell,
c. introducing the first anucleate cell and second anucleate cell into the individual, wherein said antigen is processed in a tolerogenic environment, and wherein presentation of said antigen in said tolerogenic environment suppresses an immune response to the antigen.

Embodiment 5

A method for suppressing an immune response in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment, wherein presentation of said antigen in said tolerogenic environment suppresses an immune response to the antigen.

Embodiment 6

A method for suppressing an immune response in an individual, the method comprising introducing an anucleate cell into the individual, wherein the anucleate cell comprises an antigen and a tolerogenic factor, wherein the antigen and the tolerogenic factor were introduced to the anucleate cell by passing the anucleate cell through a constriction, wherein said constriction deformed the cell thereby causing a perturbation of the cell such that the antigen and the tolerogenic factor entered the anucleate cell, wherein said antigen is processed in a tolerogenic environment, and wherein presentation of said antigen in said tolerogenic environment suppresses an immune response to the antigen.

Embodiment 7

A method for delivering a tolerogenic factor into an anucleate cell, the method comprising passing a cell suspension comprising the anucleate cell through a constriction, wherein said constriction deforms the anucleate cell, thereby causing a perturbation of the cell such that the tolerogenic factor enters the cell, wherein said cell suspension is contacted with the tolerogenic factor.

Embodiment 8

A method for introducing an antigen into a tolerogenic environment comprising delivering an anucleate cell into an individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment.

Embodiment 9

A method for introducing an antigen and a tolerogenic factor into a tolerogenic environment comprising delivering an anucleate cell into an individual, wherein the anucleate cell comprises the antigen and the tolerogenic factor, wherein the antigen and the tolerogenic factor were introduced to the anucleate cell by passing the anucleate cell through a constriction, wherein said constriction deformed the cell thereby causing a perturbation of the cell such that the antigen and the tolerogenic factor entered the anucleate cell, wherein said antigen is processed in a tolerogenic environment.

Embodiment 10

A method for inducing antigen-specific tolerance in an individual, the method comprising:

a. passing a cell suspension comprising an anucleate cell through a constriction, wherein said constriction deforms the cell thereby causing a perturbation of the cell such that an antigen enters the anucleate cell; and
b. introducing the anucleate cell into the individual, wherein said antigen is processed in a tolerogenic environment, wherein presentation of said antigen in said tolerogenic environment induces tolerance to the antigen.

Embodiment 11

A method for inducing tolerance in an individual, the method comprising:

a. passing a cell suspension comprising an anucleate cell through a constriction, wherein said constriction deforms the cell thereby causing a perturbation of the cell such that a tolerogenic factor enters the anucleate cell; and
b. introducing the anucleate cell into the individual.

wherein said tolerogenic factor contributes to a tolerogenic environment that induces tolerance.

Embodiment 12

A method for inducing tolerance in an individual, the method comprising:

a. passing a cell suspension comprising an anucleate cell through a constriction, wherein said constriction deforms the cell thereby causing a perturbation of the cell such that an antigen and a tolerogenic factor enter the anucleate cell; and
b. introducing the anucleate cell into the individual, wherein said antigen is processed in a tolerogenic environment, and wherein presentation of said antigen in said tolerogenic environment induces tolerance to the antigen.

Embodiment 13

A method for inducing antigen-specific tolerance in an individual, comprising:

a. passing a first cell suspension comprising a first anucleate cell through a constriction, wherein said constriction deforms the cell thereby causing a perturbation of the cell such that an antigen enters the anucleate cell,
b. passing a second cell suspension comprising a second anucleate cell through a constriction, wherein said constriction deforms the cell thereby causing a perturbation of the cell such that a tolerogenic factor enters the anucleate cell,
c. introducing the first anucleate cell and second anucleate cell into the individual, wherein said antigen and said tolerogenic factors are processed in a tolerogenic environment, wherein presentation of said antigen in said tolerogenic environment induces tolerance to the antigen.

Embodiment 14

A method for inducing antigen-specific tolerance in an individual, the method comprising introducing an anucleate cell into the individual, wherein the anucleate cell comprises an antigen, wherein the antigen was introduced to the anucleate cell by passing the anucleate cell through a constriction, wherein said constriction deformed the cell thereby causing a perturbation of the cell such that the antigen entered the anucleate cell, wherein said antigen is processed in a tolerogenic environment, wherein presentation of said antigen in said tolerogenic environment induces tolerance to the antigen.

Embodiment 15

A method for inducing antigen-specific tolerance in an individual, the method comprising introducing an anucleate cell into the individual, wherein the anucleate cell comprises an antigen and a tolerogenic factor, wherein the antigen and the tolerogenic factor were introduced to the anucleate cell by passing the anucleate cell through a constriction, wherein said constriction deformed the cell thereby causing a perturbation of the cell such that the antigen and the tolerogenic factor entered the anucleate cell, wherein said antigen is processed in a tolerogenic environment, and wherein presentation of said antigen in said tolerogenic environment induces tolerance to the antigen.

Embodiment 16

A method for delivering an antigen into an anucleate cell, the method comprising passing a cell suspension comprising the anucleate cell through a constriction, wherein said constriction deforms the anucleate cell, thereby causing a perturbation of the cell such that the antigen enters the cell, wherein said cell suspension is contacted with the antigen.

Embodiment 17

A method for delivering an antigen and a tolerogenic factor into an anucleate cell, the method comprising passing a cell suspension comprising the anucleate cell through a constriction, wherein said constriction deforms the anucleate cell, thereby causing a perturbation of the cell such that the antigen and the tolerogenic factor enter the cell, wherein said cell suspension is contacted with the antigen and the tolerogenic factor.

Embodiment 18

The method of embodiment 16 or 17, wherein processing and presentation of said antigen in a tolerogenic environment suppresses an immune response to the antigen.

Embodiment 19

The method of embodiment 16 or 17, wherein processing and presentation of said antigen in a tolerogenic environment induces tolerance to the antigen.

Embodiment 20

The method of any one of embodiments 1, 4, 5, 8, 10, and 13-19, wherein at least one additional antigen is introduced into the cell.

Embodiment 21

The method of any one of embodiments 2-4, 6, 7, 9, 11, 12, 13, 15, and 17, wherein at least one additional tolerogenic factor is introduced into the cell.

Embodiment 22

The method of any one of embodiments 1-6, 8-15, 18, and 19, wherein the tolerogenic environment is located in the spleen, liver, or lymph nodes.

Embodiment 23

The method of any one of embodiments 1-22, wherein the constriction is contained within a microfluidic channel.

Embodiment 24

The method of any one of embodiments 1-23, wherein the channel comprises a constriction width of about 0.25 μm to about 4 μm.

Embodiment 25

The method of any one of embodiments 1-24, wherein the channel comprises a constriction width of about 4 μm, 3.5 μm, about 3 μm, about 2.5 μm, about 2 μm, about 1.5 μm, about 1 μm, about 0.5 μm, or about 0.25 μm.

Embodiment 26

The method of any one of embodiments 1-22, wherein the constriction is a pore or contained within a pore.

Embodiment 27

The method of embodiment 26, wherein the pore is contained in a surface.

Embodiment 28

The method of embodiment 27, wherein the surface is a filter.

Embodiment 29

The method of embodiment 27, wherein the surface is a membrane.

Embodiment 30

The method of any one of embodiments 26-29, wherein the pore size is about 0.5 μm to about 4 μm.

Embodiment 31

The method of any one of embodiments 26-30, wherein the pore size is 4 μm, about 3 μm, about 2 μm about 1 μm, or about 0.5 μm.

Embodiment 32

The method of any one of embodiments 1-31, wherein the constriction size is a function of the diameter of the anucleate cell.

Embodiment 33

The method of any one of embodiments 1-32, wherein the constriction size is about 10%, about 20%, about 30%, about 40%, about 50%, about 60%, or about 70% of the cell diameter.

Embodiment 34

The method of any one of embodiments 1-33, wherein the method is performed between about −5° C. and about 45° C.

Embodiment 35

The method of any one of embodiments 1-4, 7, 10-13, and 16-34, wherein the cell suspension comprises a mixed cell population.

Embodiment 36

The method of embodiment 35, wherein the cell suspension is whole blood.

Embodiment 37

The method of any one of embodiments 1-4, 7, 10-13, and 16-34, wherein the cell suspension comprises a purified cell population.

Embodiment 38

The method of embodiment 37, wherein the cell suspension comprises a purified anucleate cell population.

Embodiment 39

The method of any one of embodiments 1-4, 7, 10-13, and 16-38, wherein the cell suspension comprises mammalian cells.

Embodiment 40

The method of any one of embodiments 1-4, 7, 10-13, and 16-39, wherein the cell suspension comprises monkey, mouse, dog, cat, horse, rat, sheep, goat, pig, or rabbit cells.

Embodiment 41

The method of any one of embodiments 1-4, 7, 10-13, and 16-39, wherein the cell suspension comprises human cells.

Embodiment 42

The method of any one of embodiments 1-41, wherein the anucleate cell is a red blood cell.

Embodiment 43

The method of embodiment 42, wherein the red blood cell is an erythrocyte.

Embodiment 44

The method of embodiment 42, wherein the red blood cell is a reticulocyte.

Embodiment 45

The method of any one of embodiments 1-41, wherein the anucleate cell is a platelet.

Embodiment 46

The method of any one of embodiments 1-45, wherein the anucleate cell is a mammalian cell.

Embodiment 47

The method of any one of embodiments 1-46, wherein the anucleate cell is a monkey, mouse, dog, cat, horse, rat, sheep, goat, pig, or rabbit cell.

Embodiment 48

The method of any one of embodiments 1-46, wherein the anucleate cell is a human cell.

Embodiment 49

The method of any one of embodiments 1-5, 8-14, and 22-48, wherein the anucleate cell is from the individual.

Embodiment 50

The method of any one of embodiments 1-5, 8-14, and 22-48, wherein the anucleate cell is from a different individual.

Embodiment 51

The method of any one of embodiments 1, 4, 5, 8-10, and 13-50, wherein the antigen is located in a cell lysate.

Embodiment 52

The method of any one of embodiments 1, 4, 5, 8-10, and 13-50, wherein the antigen is a foreign antigen.

Embodiment 53

The method of any one of embodiments 1, 4, 5, 8-10, and 13-50, wherein the antigen is a self-antigen.

Embodiment 54

The method of any one of embodiments 1, 4, 5, 8-10, and 13-50, wherein the antigen is an allograft transplantation antigen.

Embodiment 55

The method of any one of embodiments 1, 4, 5, 8-10, and 13-50, wherein the antigen is a protein or polypeptide.

Embodiment 56

The method of any one of embodiments 1, 4, 5, 8-10, and 13-50, wherein the antigen is a lysate.

Embodiment 57

The method of any one of embodiments 1, 4, 5, 8-10, and 13-50, wherein the antigen is a microorganism.

Embodiment 58

The method of any one of embodiments 1, 4, 5, 8-10, and 13-50, wherein the antigen is a lipid antigen.

Embodiment 59

The method of any one of embodiments 1, 4, 5, 8-10, and 13-50, wherein the antigen is a carbohydrate antigen.

Embodiment 60

The method of any one of embodiments 1, 4, 5, 8-10, and 13-59 wherein the antigen is a modified antigen.

Embodiment 61

The method of embodiment 60, wherein the modified antigen comprises an antigen fused with a polypeptide.

Embodiment 62

The method of embodiment 60 or 61, wherein the modified antigen comprises an antigen fused with a therapeutic agent.

Embodiment 63

The method of embodiment 60 or 61, wherein the modified antigen comprises an antigen fused with a targeting peptide.

Embodiment 64

The method of embodiment 60 or 61, wherein the modified antigen comprises an antigen fused with a lipid.

Embodiment 65

The method of embodiment 60 or 61, wherein the modified antigen comprises an antigen fused with a carbohydrate.

Embodiment 66

The method of any one of embodiments 1, 4, 5, 8-10, and 13-50, wherein the antigen is an antigen associated with transplanted tissue.

Embodiment 67

The method of any one of embodiments 1, 4, 5, 8-10, and 13-50, wherein the antigen is associated with a virus.

Embodiment 68

The method of any one of embodiments 1, 4, 10, 13, and 16-67, wherein said cell suspension is contacted with the antigen before, concurrently, or after passing through the constriction.

Embodiment 69

The method of any one of embodiments 2-4, 7, 11-13, and 22-68, wherein the tolerogenic factor comprises a polypeptide.

Embodiment 70

The method of embodiment 69, wherein the polypeptide is IL-4, IL-10, IL-13, IL-35, IFNα, or TGFβ.

Embodiment 71

The method of embodiment 69, wherein the polypeptide is a therapeutic polypeptide.

Embodiment 72

The method of embodiment 69, wherein the polypeptide is a fragment of a therapeutic polypeptide.

Embodiment 73

The method of embodiment 69, wherein the polypeptide is a therapeutic peptide.

Embodiment 74

The method of embodiment 69, wherein the polypeptide is conjugated to a carbohydrate.

Embodiment 75

The method of any one of embodiments 2-4, 7, 11-13, and 22-74, wherein said cell suspension is contacted with the tolerogenic factor before, concurrently, or after passing through the constriction.

Embodiment 76

The method of any one of embodiment 1-75, wherein the half-life of the anucleate cell is decreased.

Embodiment 77

The method of any one of embodiment 1-75, wherein the half-life of the anucleate cell is increased.

Embodiment 78

The method of any one of embodiment 1-6, 18, and 22-77, wherein the immune response is suppressed by at least about 10%, about 15%, about 20%, about 25%, about 30%, about 40%, about 50%, about 60%, about 70%, about 75%, about 80%, about 90%, or about 100%.

Embodiment 79

The method of any one of embodiments 1-6, 18, and 22-78, wherein the suppressed immune response comprises decreased production and/or secretion of one or more inflammatory cytokines.

Embodiment 80

The method of embodiment 79, wherein the one or more inflammatory cytokines are selected from the group consisting of interleukin-1 (IL-1). IL-12, and IL-18, tumor necrosis factor (TNF), interferon gamma (IFN-gamma), and granulocyte-macrophage colony stimulating factor (GM-CSF).

Embodiment 81

The method of any one of embodiments 1-6, 18, and 22-78, wherein the suppressed immune response comprises increased production and/or secretion of one or more anti-inflammatory cytokines.

Embodiment 82

The method of embodiment 81, wherein the one or more anti-inflammatory cytokines are selected from the group consisting of IL-4, IL-10, IL-13, IL-35, IFN-α and transforming growth factor-beta (TGFβ).

Embodiment 83

The method of any one of embodiments 1-6, 18, and 22-78, wherein the suppressed immune response comprises a decreased T cell response.

Embodiment 84

The method of embodiment 83, wherein the decreased T cell response comprises decreased T cell activation.

Embodiment 85

The method of embodiment 83 or 84, wherein the decreased T cell response comprises decreased T cell survival.

Embodiment 86

The method of any one of embodiments 83-85, wherein the decreased T cell response comprises decreased T cell proliferation.

Embodiment 87

The method of any one of embodiments 83-86, wherein the decreased T cell response comprises decreased T cell functionality.

Embodiment 88

The method of any one of embodiments 83-87, wherein the decreased T cell response comprises a change in T cell phenotype.

Embodiment 89

The method of any one of embodiments 1-6, 18, and 22-88, wherein the suppressed immune response comprises uncostimulated activation of a T cell.

Embodiment 90

The method of any one of embodiments 1-6, 18, and 22-89, wherein the suppressed immune response comprises an enhanced Treg response.

Embodiment 91

The method of any one of embodiments 1-6, 18, and 22-90, wherein the suppressed immune response comprises a decreased B cell response.

Embodiment 92

The method of embodiment 91, wherein the decreased B cell response comprises decreased antibody production.

Embodiment 93

The method of any one of embodiments 1-6, 18, and 22-92, wherein the suppressed immune response comprises decreased cytokine production.

Embodiment 94

The method of any one of embodiments 1-6, 18, and 22-93, wherein the suppressed immune response comprises a decreased autoimmune response.

Embodiment 95

The method of any one of embodiments 1-6, 18, and 22-94, wherein the suppressed immune response comprises a decreased allergic response.

Embodiment 96

The method of any one of embodiments 1-6, 18, and 22-95, wherein the suppressed immune response comprises a decreased immune response against the transplanted tissue.

Embodiment 97

The method of any one of embodiments 1-6, 18, and 22-95, wherein the suppressed immune response comprises a decreased pathogenic immune response to the virus.

Embodiment 98

The method of any one of embodiments 1-6, 18, and 22-95 wherein the suppressed immune response comprises a decreased immune response against a therapeutic agent.

Embodiment 99

The method of any one of embodiments 1-6, 18, and 22-95, wherein the suppressed immune response comprises a decreased immune response against a therapeutic vehicle.

Embodiment 100

The method of any one of embodiments 10-15 and 19-77, wherein the tolerance comprises decreased production and/or secretion of one or more inflammatory cytokines.

Embodiment 101

The method of embodiment 100, wherein the one or more inflammatory cytokines are selected from the group consisting of interleukin-1 (IL-1). IL-12, and IL-18, tumor necrosis factor (TNF), interferon gamma (IFN-gamma), and granulocyte-macrophage colony stimulating factor (GM-CSF).

Embodiment 102

The method of any one of embodiments 10-15 and 19-77, wherein the tolerance comprises increased production and/or secretion of one or more anti-inflammatory cytokines.

Embodiment 103

The method of embodiment 102, wherein the one or more anti-inflammatory cytokines are selected from the group consisting of IL-4. IL-10. IL-13, IL-35, IFN-α and transforming growth factor-beta (TGFβ).

Embodiment 104

The method of any one of embodiments 10-15 and 19-77, wherein the tolerance comprises a decreased T cell response.

Embodiment 105

The method of embodiment 104, wherein the decreased T cell response comprises decreased T cell activation.

Embodiment 106

The method of embodiment 104 or 105, wherein the decreased T cell response comprises decreased T cell survival.

Embodiment 107

The method of any one of embodiments 104-106, wherein the decreased T cell response comprises decreased T cell proliferation.

Embodiment 108

The method of any one of embodiments 104-107, wherein the decreased T cell response comprises decreased T cell functionality.

Embodiment 109

The method of any one of embodiments 104-108, wherein the decreased T cell response comprises a change in T cell phenotype.

Embodiment 110

The method of any one of embodiments 10-15, 19-77, and 104-109, wherein the tolerance comprises uncostimulated activation of a T cell.

Embodiment 111

The method of any one of embodiments 10-15, 19-77, and 104-110, wherein the tolerance comprises an enhanced Treg response.

Embodiment 112

The method of any one of embodiments 10-15, 19-77, and 104-111, wherein the tolerance comprises a decreased B cell response.

Embodiment 113

The method of embodiment 112, wherein the decreased B cell response comprises decreased antibody production.

Embodiment 114

The method of any one of embodiments 10-15, 19-77, and 104-113, wherein the tolerance comprises decreased cytokine production.

Embodiment 115

The method of any one of embodiments 10-15, 19-77, and 104-114, wherein the tolerance comprises a decreased autoimmune response.

Embodiment 116

The method of any one of embodiments 10-15, 19-77, and 104-115, wherein the tolerance comprises a decreased allergic response.

Embodiment 117

The method of any one of embodiments 10-15, 19-77, and 104-116, wherein the tolerance comprises a decreased immune response against the transplanted tissue.

Embodiment 118

The method of any one of embodiments 10-15, 19-77, and 104-116, wherein the tolerance comprises a decreased pathogenic immune response to the virus.

Embodiment 119

The method of any one of embodiments 10-15, 19-77, and 104-116, wherein the tolerance comprises a decreased immune response against a therapeutic agent.

Embodiment 120

The method of any one of embodiments 10-15, 19-77, and 104-116, wherein the tolerance comprises a decreased immune response against a therapeutic vehicle.

Embodiment 121

The method of any one of embodiments 1-120, wherein the method is repeated at least 1, 2, 3, 4, 5, or 6 times.

Embodiment 122

The method of embodiment 121, wherein the duration of time between any two repetitions of the method is at least 1 day, 1 week, 1 month, 2 months, 3 months, 4 months, 5 months, 6 months, or 1 year.

Embodiment 123

A system comprising the constriction, cell suspension, and antigen for use in the methods of any one of embodiments 1, 4, 10, 13, and 16-120.

Embodiment 124

A system comprising the constriction, cell suspension, and tolerogenic factor for use in the methods of any one of embodiments 2-4, 7, 11-13, and 22-120.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

Example 1: Constriction-Mediated Delivery of Dextran and IgG Antibody to Human RBCs Introduction In order to evaluate filter-mediated delivery of molecules into anucleate cells, human RBCs mixed with fluorescent dextran particles or IgG antibody were passed through syringe filters containing pores of defined sizes, and intracellular particle delivery was evaluated via FACS analysis.

Materials and Methods

2 μm diameter pore size polycarbonate membrane filters with a commercial filter and holder combination (COTS filters) were obtained from STERLITECH™. Human RBCs were separated from whole blood or leukoreduction collar using a Ficoll gradient separation method and resuspended at the desired concentration (50-500M/mL) in Optimem.

The polycarbonate membrane filter was suspended in Optimem using forceps to wet the membrane filer. The plastic filter holder was uncapped, the filter was placed onto the inside surface with the shiny-side facing upwards, and the filter holder was recapped. Dextran particles and IgG antibody were suspended at 0.1 mg/mL. 1 mL of cells mixed with dextran particles or IgG antibody was added into the filter holder at room temperature. A manual finger push on the syringe was used to drive the cells through the filter. The filter flow-through was collected into a 15 ml Falcon tube or FACS tube. Before FACS analysis all samples were centrifuged and washed three times at 400 rcf for 4 minutes at 4° C. to remove extracellular dextrans. To prepare for FACS analysis the following steps were taken. FACS buffer was prepared (PBS+final concentration: 1% FBS+2 mM EDTA) and 400 μL of FACS buffer was added per tube and the cells were resuspended. The flow cytometry forward scatter, side scatter and fluorescent channel voltages were adjusted to visualize all cell events and ≥10.000 events/sample were recorded. Cells mixed with dextran particles or IgG antibody, but not passed through the filters, were used as a control for delivery via endocytosis. These cells had contact with dye but were not passed through the filters. All other steps were the same for the endocytosis controls.

Results

Figure 1A:
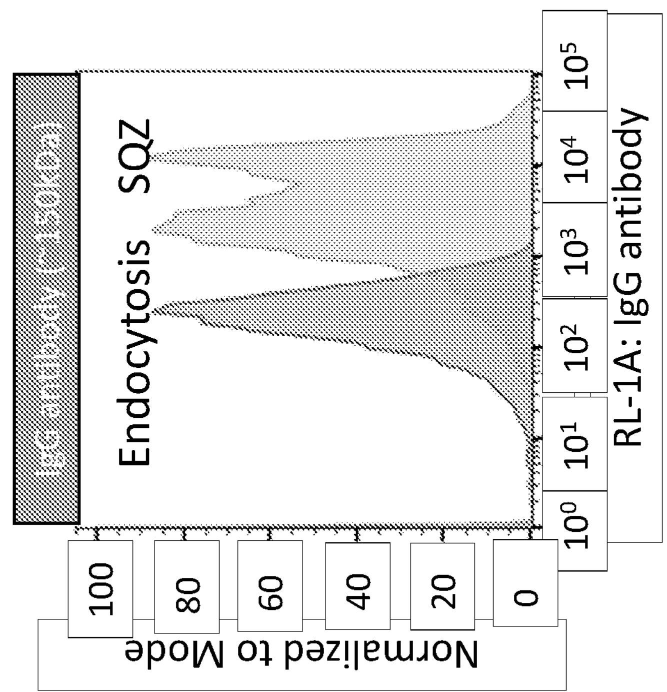
Figure 2A:
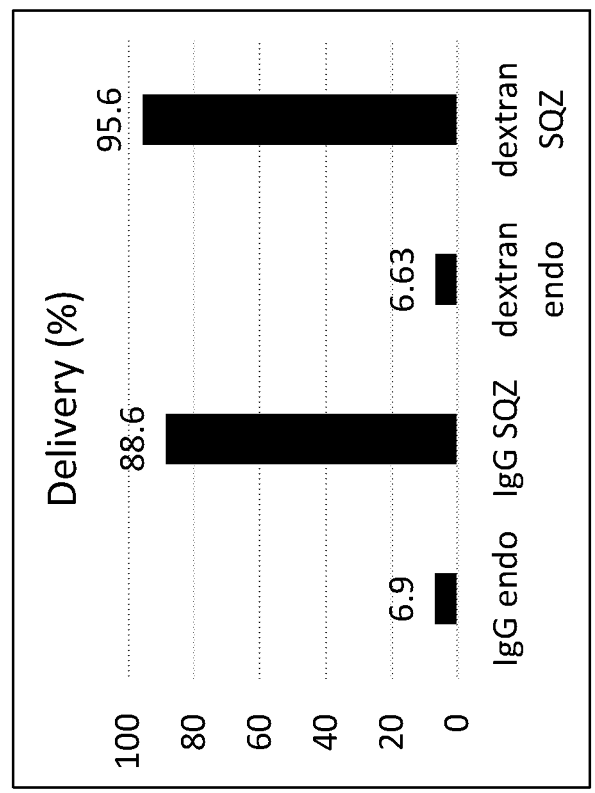
FIG. 2A shows delivery efficiency post constriction mediated delivery of IgG antibody and dextran particles to human RBCs.

RBCs mixed with 10 kDa Alexa Fluor® 647 dextran particles or 150 kDa IgG antibody conjugated to Alexa Fluor® 647 were passed through 2 μm sized filter pores. Exemplary flow cytometry histogram plots depicting increased delivery of fluorescent dextran and IgG post constriction mediated delivery (SQZ) versus the endocytosis control are shown in FIGS. 1A&B. Delivery efficiency, as indicated by percentage of cells positive for the dextran particles of IgG antibody post-filter delivery, is shown in FIG. 2A. Delivery efficiency of IgG antibody was 88.6%, and delivery efficiency of dextran particles was 95.6% post-filter delivery, compared to <10% delivery efficiency for both molecules in endocytosis controls.

Figure 2B:
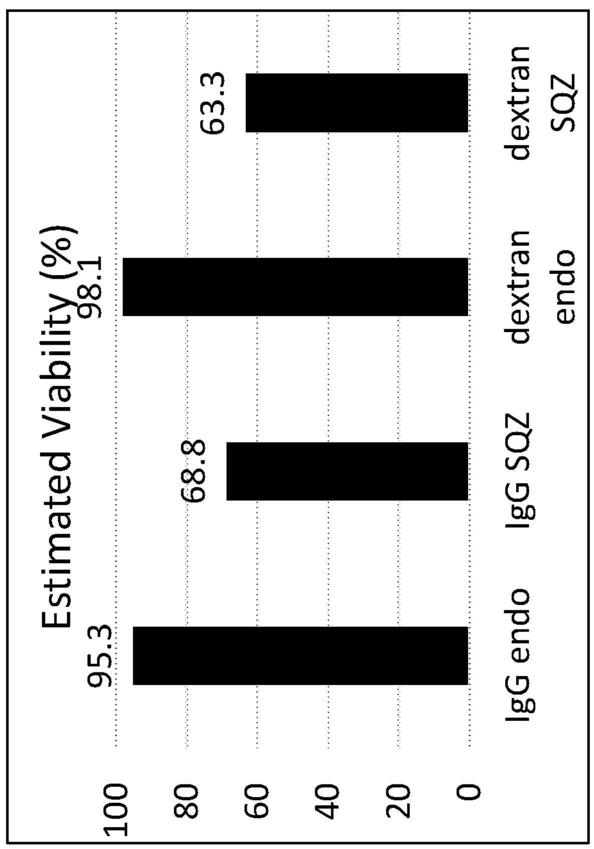
FIG. 2B shows estimated cell viability post constriction mediated delivery of IgG antibody and dextran particles to human RBCs.

Cell viability was measured post-filter delivery. Estimated cell viability, as indicated by percentage of cells present within the FSC and SSC gate post-filter delivery, is shown in FIG. 2B. Estimated viability of cells delivered IgG antibody was 68.8%, and estimated viability of cells delivered dextran particles was 63.3% post-filter delivery.

Constriction mediated delivery of dextran particles and IgG antibody into human RBCs was achieved.

Example 2: Constriction-Mediated Delivery of Dextran and IgG Antibody to Mouse RBCs Introduction In order to evaluate filter-mediated delivery of molecules into anucleate cells, mouse RBCs mixed with fluorescent dextran particles or IgG antibody were passed through syringe filters containing pores of defined sizes, and intracellular particle delivery was evaluated via FACS analysis.

Materials and Methods

1 μm and 2 μm diameter pore size polycarbonate membrane filters with a commercial filter and holder combination (COTS filters) were obtained from STERLITECH™. Whole blood was spun down and cells were resuspended at the desired concentration (100-500 M/ml) in Optimem. The polycarbonate membrane filter was suspended in Optimem using forceps to wet the membrane filer. The plastic filter holder was uncapped, the filter was placed onto the inside surface with the shiny-side facing upwards, and the filter holder was recapped. Dextran particles and IgG antibody were suspended at 0.1 mg/mL. 1 mL of cells mixed with dextran particles or IgG antibody was added into the filter holder at room temperature. A manual finger push on the syringe was used to drive the cells through the filter. Alternatively, a controlled pressure system is used to drive 200 μL of cells mixed with dextran particles or IgG antibody through the filter. The filter flow-through was collected into a 15 ml Falcon tube or FACS tube. Before FACS analysis all samples were centrifuged and washed three times at 1000 rfc for 10 minutes at 24° C. to remove extracellular dextrans. To prepare for FACS analysis the following steps were taken. FACS buffer was prepared (PBS+final concentration: 1% FBS+2 mM EDTA) and 400 μL of FACS buffer was added per tube and the cells were resuspended. The flow cytometry forward scatter, side scatter and fluorescent channel voltages were adjusted to visualize all cell events and ≥10,000 events/sample were recorded. Cells mixed with dextran particles or IgG antibody, but not passed through the filters, were used as a control for delivery via endocytosis. These cells had contact with dye but were not passed through the filters. All other steps were the same for the endocytosis controls. The NC (No contact) samples did not have contact with dye but were subjected to the same steps as the experimental samples but were not passed through the filters.

Results

Figure 3A:
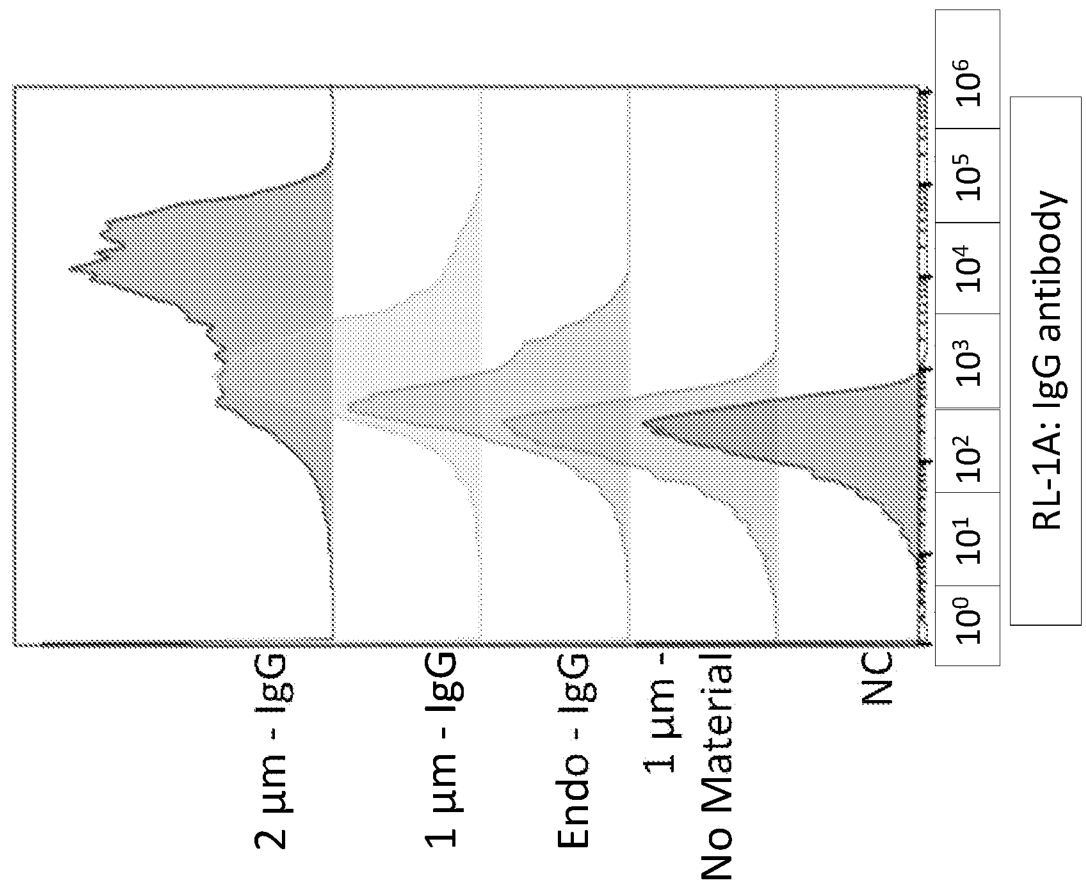
FIG. 3A shows exemplary flow cytometry histogram plots depicting fluorescence post constriction mediated delivery of IgG antibody to mouse RBCs.

Mouse RBCs mixed with IgG antibody (150 kDa) were passed through 1 μm and 2 μm sized filter pores using manual syringe pressure. Exemplary flow cytometry histogram plots depicting fluorescence post constriction mediated delivery (SQZ) versus the endocytosis (Endo), negative (NC), and no material controls control are shown in FIG. 3A. The 'no material' control did not have contact with IgG antibody but was subjected to the same steps as the experimental samples and was passed through the filter.

Figure 3C:
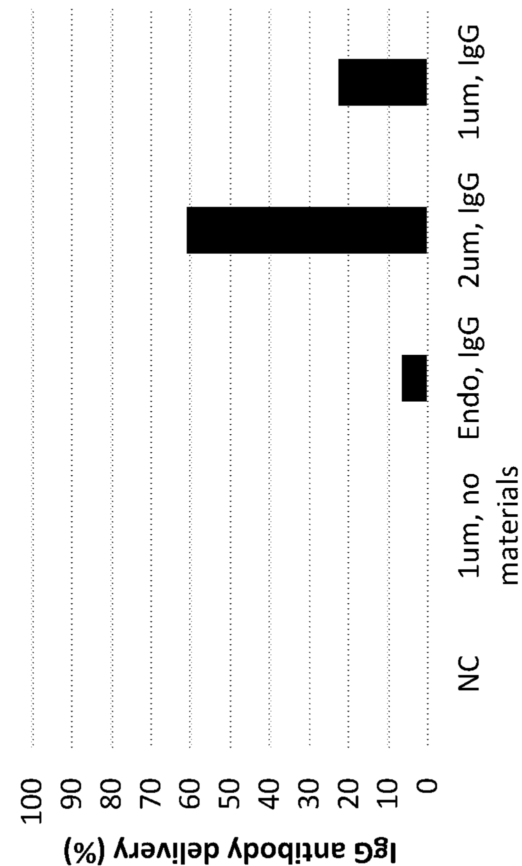
FIG. 3C shows delivery efficiency post constriction mediated delivery of IgG antibody to mouse RBCs.
Figure 3B:
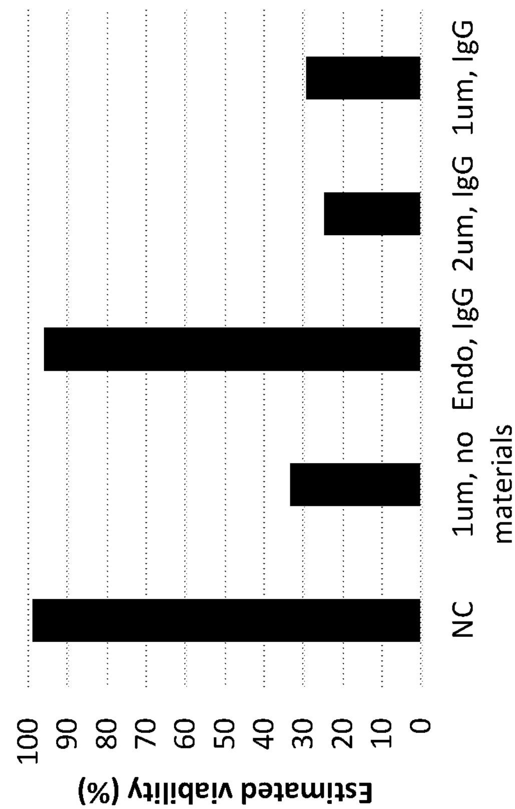
FIG. 3B shows estimated cell viability post constriction mediated delivery of IgG antibody to mouse RBCs.

Cell viability was measured post-filter delivery. Estimated cell viability, as indicated by percentage of cells present within the FSC and SSC gate post-filter delivery of IgG antibody using manual syringe pressure, is shown in FIG. 3B, with filter-mediated delivery decreasing the estimated viability by ~70% vs. controls, but leading to 4-12-fold higher delivery efficiency of IgG antibody, as shown in FIG. 3C.

Figure 4A:
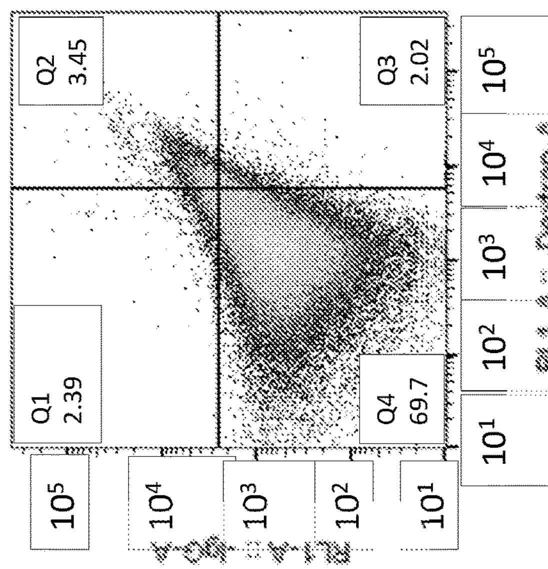
FIGS. 4A-I show exemplary FACS plots demonstrating delivery of dextran particles to mouse RBCs under 2 psi (FIG. 4D), 4 psi (FIG. 4E), 6 psi (FIG. 4F), 10 psi (FIG. 4G), 20 psi (FIG. 4H), or using manual syringe pressure (FIG. 4I) as compared to the endocytosis (FIG. 4A), negative control (FIG. 4B), and no material control (FIG. 4C).
Figure 4B:
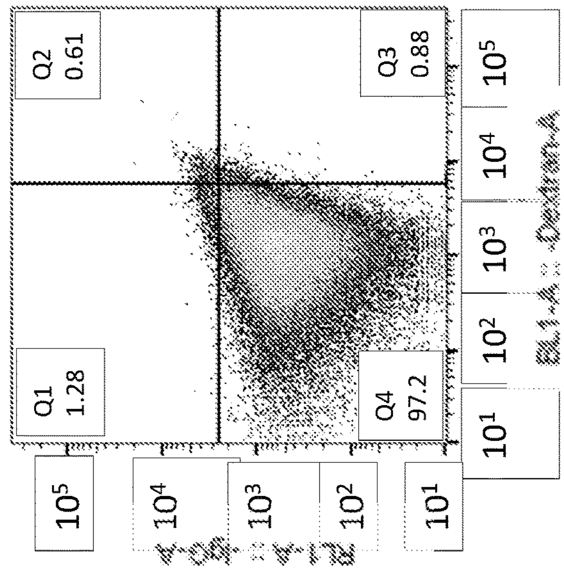
Figure 4C:
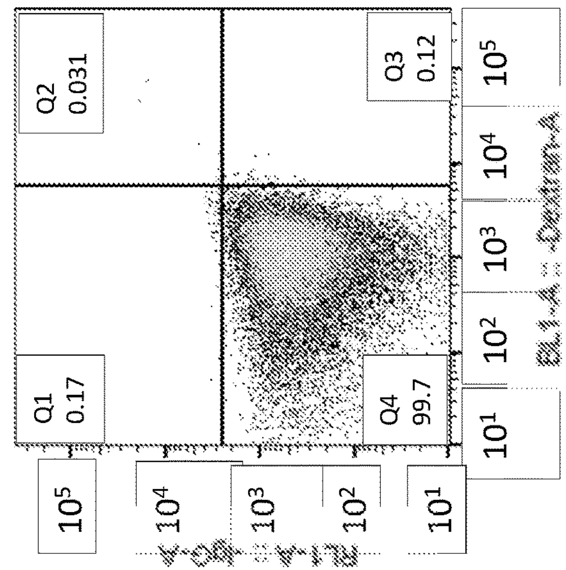
Figure 4D:
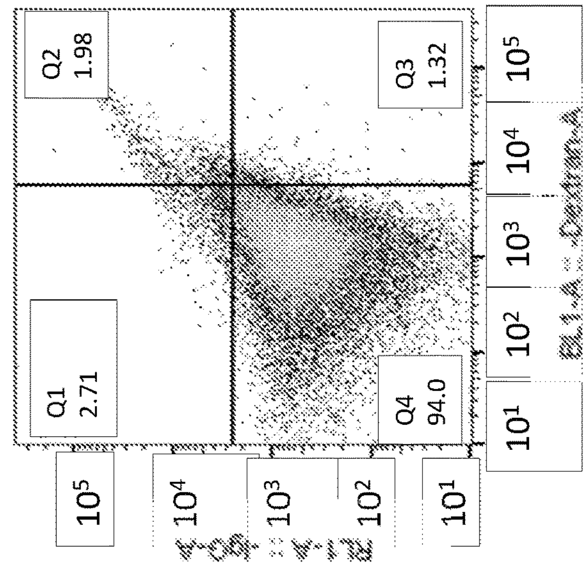
Figure 4E:
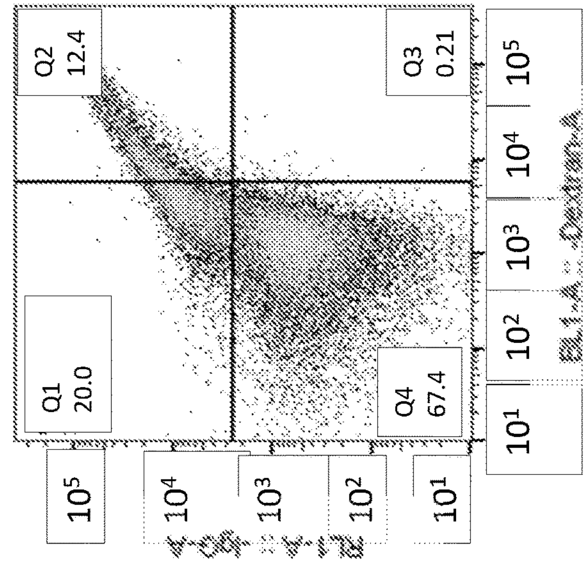
Figure 4F:
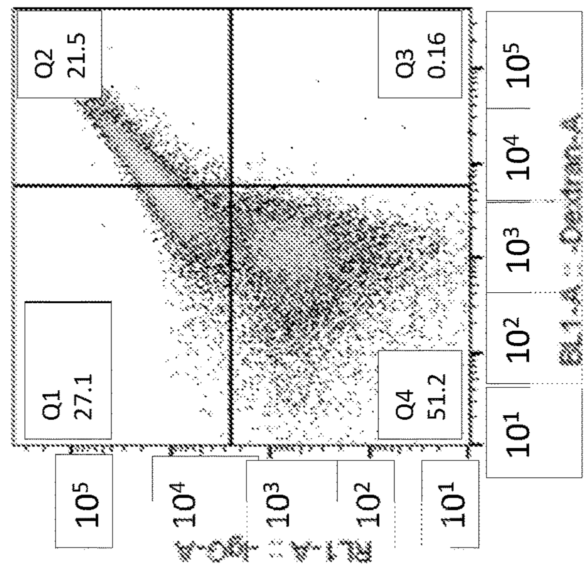
Figure 4I:
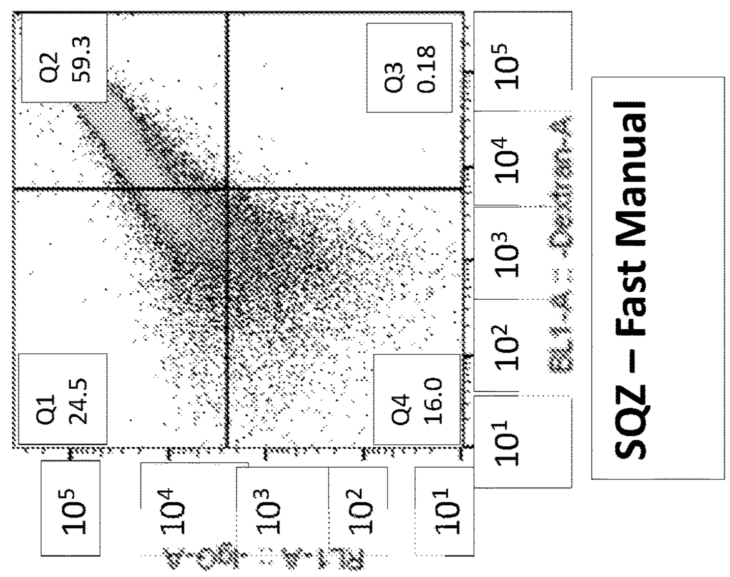
Figure 4H:
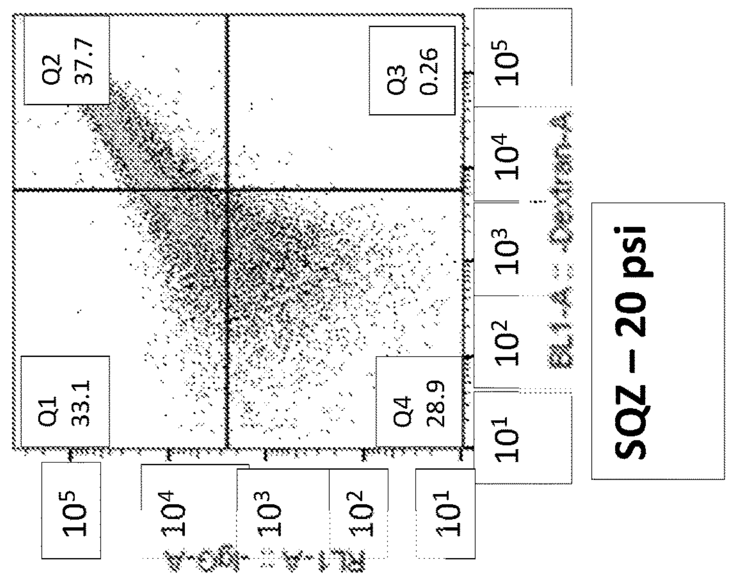
Figure 4G:
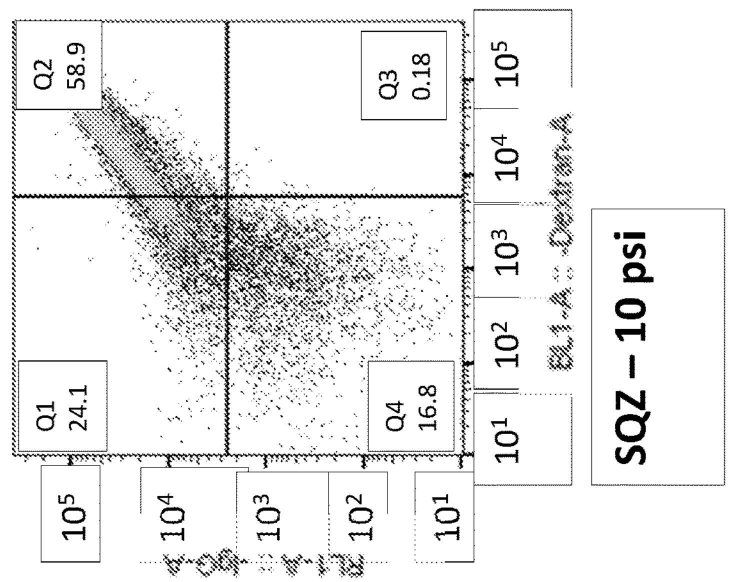
Figure 5A:
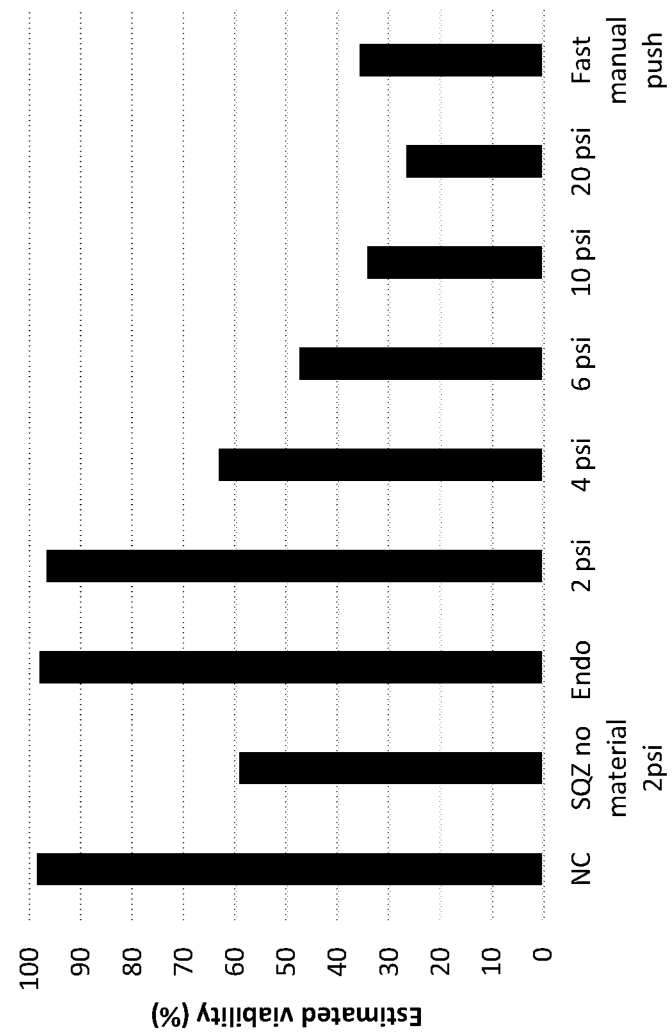
FIG. 5A shows estimated cell viability post constriction mediated delivery of dextran particles to mouse RBCs.
Figures 5B, 5C:
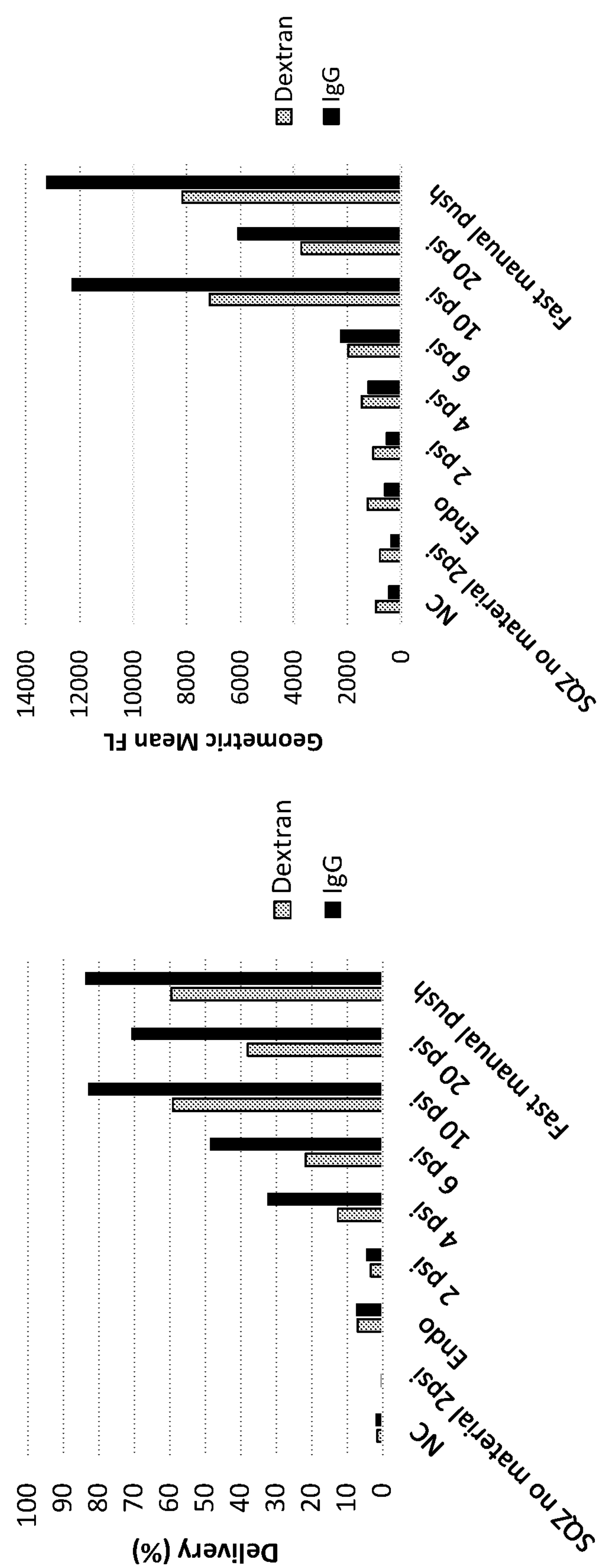
FIG. 5B shows delivery efficiency post constriction mediated delivery of IgG antibody or dextran particles to mouse RBCs.
FIG. 5C shows geometric mean fluorescence post constriction mediated delivery of IgG antibody or dextran particles to mouse RBCs.

RBCs mixed with 70 kDa Alexa Fluor® 488 dextran particles and IgG antibody (150 kDa) conjugated to Alexa Fluor® 647 were passed through 2 μm sized filter pores using a controlled pressure system under 2 psi, 4 psi, 6 psi, 10 psi, 20 psi, or using manual syringe pressure. Exemplary flow cytometry histogram plots are shown in FIGS. 4A-I, depicting fluorescence post constriction mediated delivery (SQZ—FIGS. 4D-I) versus the endocytosis (Endo—FIG. 4A), negative (NC—FIG. 4B), and no material control (FIG. 4C). These data showed that filter-mediated delivery led to up to 55% increases in dextran and IgG delivery, relative to Endo. NC and no material controls. Cell viability was also measured post-filter delivery. Estimated cell viability, as indicated by percentage of cells present within the FSC and SSC gate post-filter delivery of dextran particles is shown in FIG. 5A. Delivery efficiency, as indicated by percentage of cells positive for dextran particles or IgG antibody post-filter delivery is shown in FIG. 5B. The geometric mean fluorescence post-filter delivery of dextran particles or IgG antibody is shown in FIG. 5C.

Figure 6B:
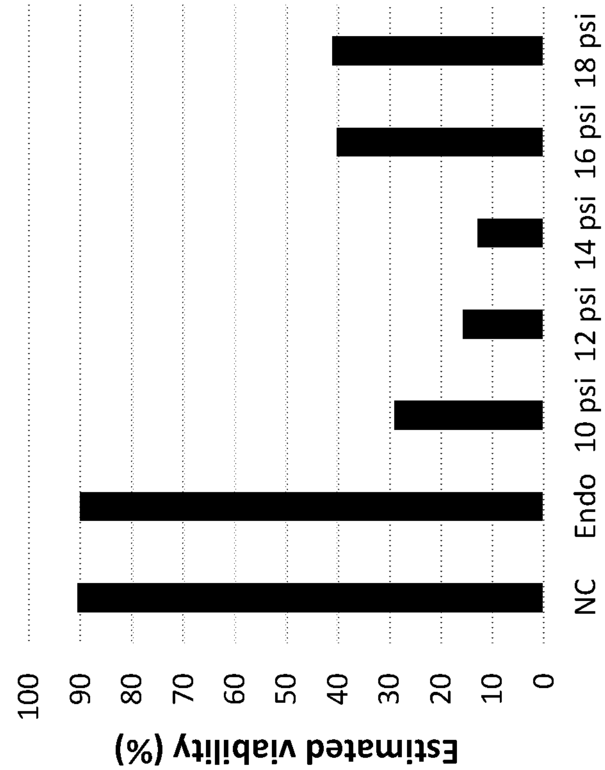
FIG. 6B shows estimated cell viability post constriction mediated delivery of dextran particles to mouse RBCs.
Figure 6A:
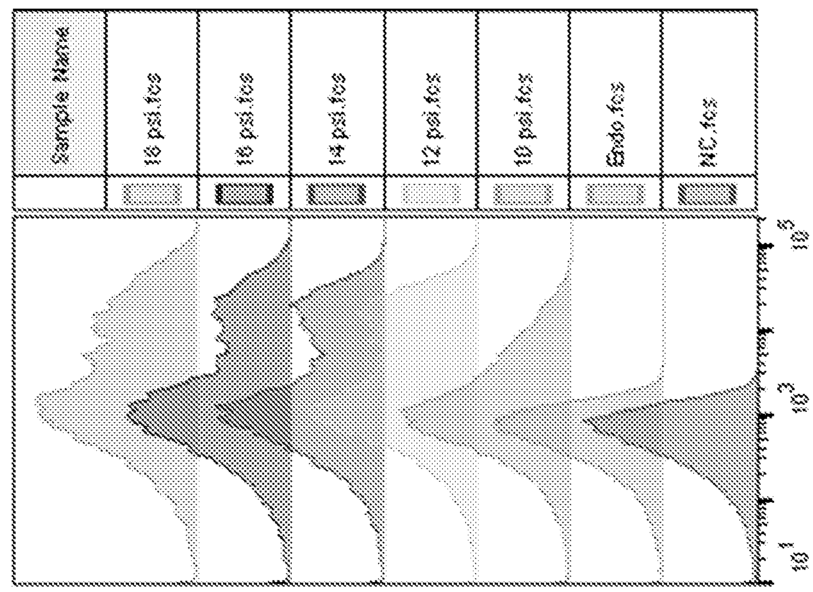
FIG. 6A shows exemplary flow cytometry histogram plots depicting fluorescence post constriction mediated delivery of dextran particles to mouse RBCs.
Figure 6D:
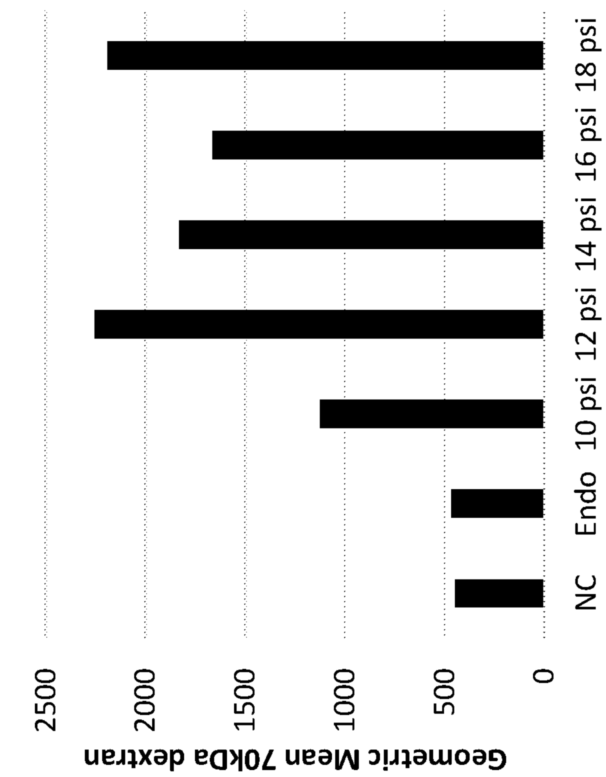
FIG. 6D shows geometric mean fluorescence post constriction mediated delivery of dextran particles to mouse RBCs.
Figure 6C:
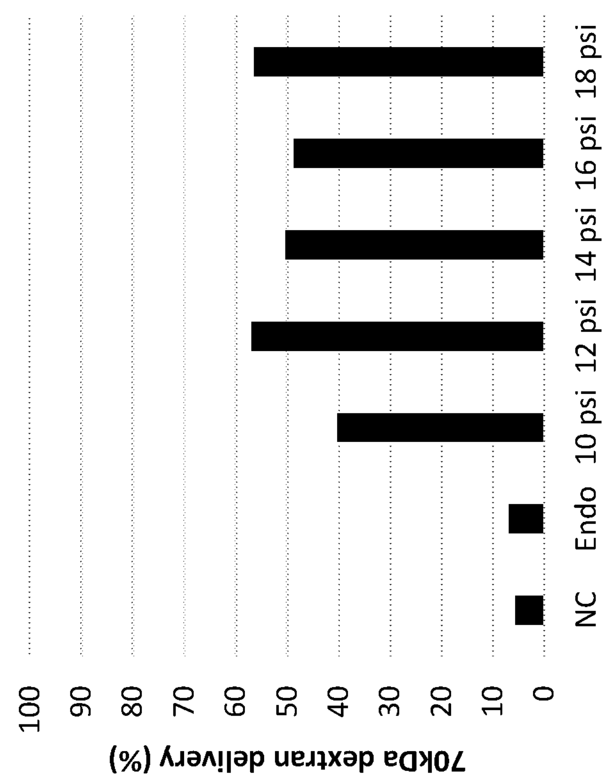
FIG. 6C shows delivery efficiency post constriction mediated delivery of dextran particles to mouse RBCs.

RBCs mixed with 70 kDa Alexa Fluor® 488 dextran particles were passed through 2 μm sized filter pores using a controlled pressure system under 10 psi, 12 psi, 14 psi, 16 psi, or 18 psi. Exemplary flow cytometry histogram plots depicting fluorescence post constriction mediated delivery (SQZ) versus the endocytosis (Endo), and negative (NC) controls are shown in FIG. 6A. Cell viability was measured post-filter delivery. Estimated cell viability, as indicated by percentage of cells present within the FSC and SSC gate post-filter delivery of dextran particles is shown in FIG. 6B. Delivery efficiency, as indicated by percentage of cells positive for dextran particles post-filter delivery is shown in FIG. 6C. The geometric mean fluorescence post-filter delivery of dextran particles is shown in FIG. 6D.

Constriction mediated delivery of dextran particles and IgG antibody into mouse RBCs was achieved.

Example 3: Constriction-Mediated Delivery of Antigen to RBCs to Induce Tolerance A series of experiments are undertaken to demonstrate induction of tolerance using model antigen and transgenic T cells.

RBCs are mixed with OVA antigen and passed through a constriction within a microfluidic channel, or through a surface containing pores. Pressure, temperature, and buffer composition are optimized to achieve delivery. OVA loaded RBCs are then introduced into a CD45.1 mouse with CFSE labeled adoptively transferred OT-I cells. Alternatively, the OT-I T cells are activated ex-vivo prior to transfer into the CD45.1 mouse. 9 days later, to allow for tolerogenic presentation and subsequent T cell deletion, mice are challenged with soluble OVA and LPS. 4 days after challenge spleen and the draining lymph nodes are analyzed for OT-I proliferation.

Example 4: Constriction-Mediated Delivery of Antigen to RBCs to Induce Tolerance In order to determine the ability of RBCs containing antigen delivered by SQZ for the induction of in vivo antigen-dependent tolerance, the number of antigen-specific T cells and the levels of inflammatory cytokine IFN-γ were measured by flow cytometry.

Materials and Methods

Figure 7:
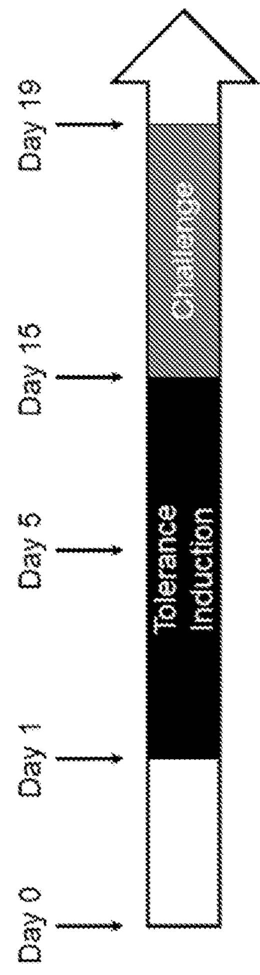
FIG. 7 shows a schematic of the treatment schedule.

C57BL/6J recipient mice (CD45.1) were adoptively transferred with 1M OVA-specific OT-I T cells per mouse from female OT-I donor mice (CD45.2) at day 0. On days 1 (prime) and 6 (boost), RBCs from C57BL/6J mice were harvested and RBCs were incubated with full OVA protein or OVA was delivered by filter-mediated SQZ conditions, followed by injection of 20-125M RBCs/mouse into recipient mice. Control animals received no injection (naïve), or injection with either PBS (challenge control) or free OVA (10 μg/animal—tolerance control). Antigen challenge occurred on day 15, with intradermal injection of 10 μg OVA protein+50 ng LPS/mouse in challenged animals, compared to naïve (no antigen or LPS). OT-I T cell response to antigen challenge was measured by flow cytometry for the number of OT-I T cells and IFN-γ intracellular staining on day 19. A schematic of the treatment schedule is shown in FIG. 7, and the treatment groups are summarized in Table 1.

TABLE 1

| Group | Day 0 | Days 1 & 5 | Day 15 |
|---|---|---|---|
| Naïve | OT-I adoptive transfer | | |
| Challenge Control | OT-I adoptive transfer | PBS | OVA + LPS |
| Tolerance Control | OT-I adoptive transfer | OVA protein | OVA + LPS |
| RBC-Endo | OT-I adoptive transfer | RBCs incubated with OVA without constriction | OVA + LPS |
| RBC-SQZ | OT-I adoptive transfer | RBCs SQZ'd with OVA with constriction | OVA + LPS |

Results

Figure 8:
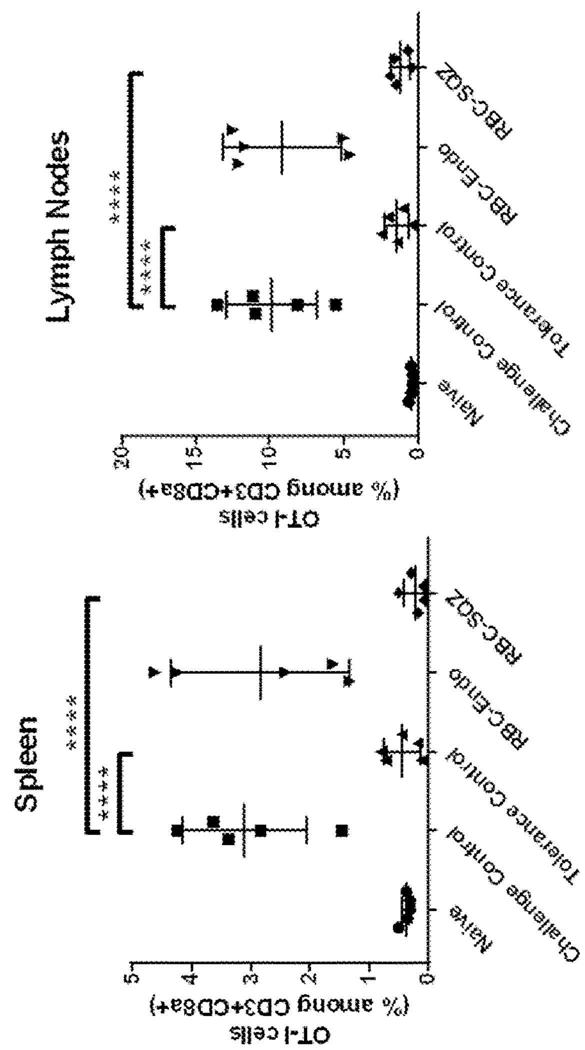
FIG. 8 shows the number of OT-I-specific T cells in mice from the four treatment groups.

OT-I-specific T cell numbers were measured in mice challenged with antigen (OVA) and adjuvant (LPS) for groups treated with either RBCs incubated with OVA protein (RBC-Endo) or intracellular OVA protein delivery by SZQ (RBC-SQZ) (FIG. 8). These conditions were compared to animals that did not see antigen, adjuvant or RBCs (naïve), or mice treated with free OVA protein (tolerance control) or PBS (challenge control) followed by antigen+adjuvant challenge. OT-I T cell numbers in both the draining lymph nodes and spleen were significantly inhibited (****$P<0.0001$) in mice primed/boosted with RBCs SQZ'd with OVA protein compared to the challenge control. These mice saw OT-I T cell numbers similar to naïve mice or the tolerance control, whereas treatment with RBCs that were incubated with OVA protein were no different that challenge control.

Figure 9:
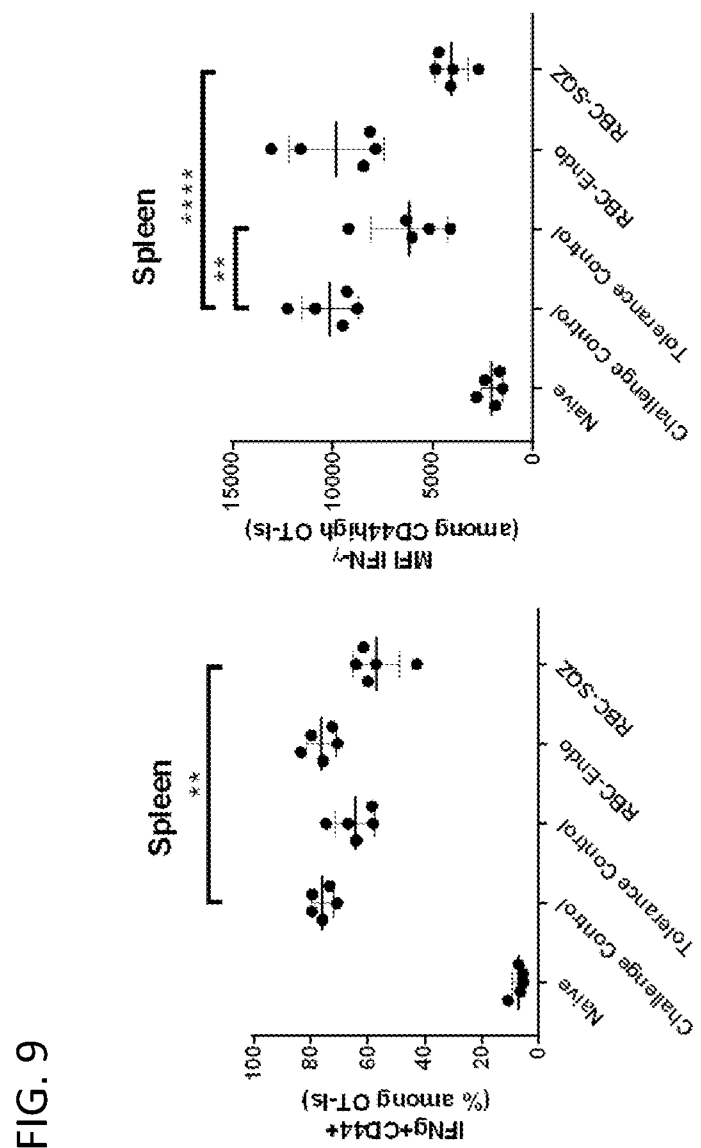
FIG. 9 shows the percent of splenic T cells that expressed high levels of IFN-γ (left) and the level of IFN-γ production (right).

To assess the functional effect of SQZ RBC-mediated tolerance on T cell function, the % of splenic T cells that expressed high levels of IFN-γ (FIG. 9, left) and the level of IFN-γ production per cell (FIG. 9, righ; based on all CD44hi cells) of OT-I T cells restimulated with SIINFEKL peptide (SEQ ID NO: 1) (active OVA epitope) were assessed for all groups by intracellular cytokine staining. OT-I T cells from mice treated with OVA SQZ'd RBCs showed a modest but significant decrease in high IFN-γ expressing cells ($P<0.005$) and a large decrease of IFN-γ production ($P<0.0001$) compared to challenge control, with a larger decrease than the tolerance control (Free Ova; $P<0.005$). However, RBCs incubated with OVA protein did not see a decrease in IFN-γ production relative to challenge control.

Figure 10:
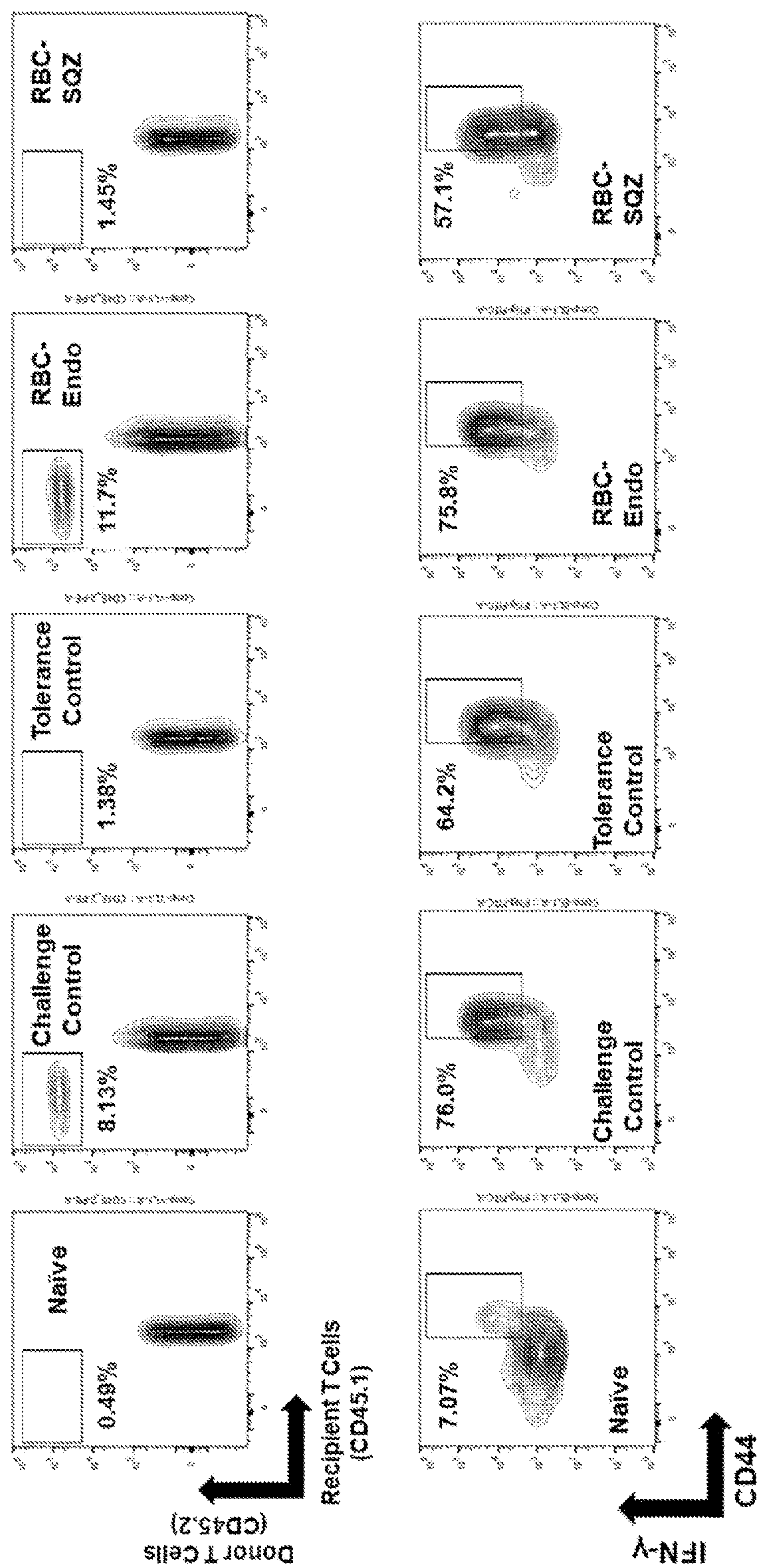
FIG. 10 shows representative flow cytograms for the proportion of OT-I T cells out of all CD8+ T cells (top panels) and the proportion of IFN-γ responsive T cells out of OT-I T cells (bottom panels).

Representative flow cytograms (FIG. 10, summarized in Table 2) for the proportion of OT-I T cells out of all CD8+ T cells and the proportion of IFN-γ responsive T cells out of OT-I T cells show that the RBC-SQZ samples had fewer OT-Is and lower IFNg response relative to challenge control and RBC-Endo conditions.

TABLE 2

| Group | % OT-I Specific Cells | % IFN-γ Expressing |
|---|---|---|
| Naïve | 0.49 | 7.07 |
| Challenge Control | 8.13 | 76.0 |
| Tolerance Control | 1.38 | 64.2 |
| RBC-Endo | 11.7 | 75.8 |
| RBC-SQZ | 1.45 | 57.1 |

Example 5: CD4+/CD8+ Mediated Tolerance

To determine the ability of red blood cells (RBCs) containing antigen delivered by SQZ induce CD4- and/or CD8- mediated T cell antigen-dependent tolerance in vivo, the number of antigen-specific T cells and the levels of inflammatory cytokine IFN-γ are measured by flow cytometry.

Materials and Methods

C57BL/6J recipient mice (CD45.1+) are adoptively transferred with 1M OVA-specific CD8+OT-I and 2-4M CD4+ OT-II T cells (both CD45.2+) per mouse from female donor mice at day 0. On days 1 (prime) and 6 (boost), RBCs from C57BL/6J mice are harvested and RBCs are incubated with full OVA protein or OVA is delivered by SQZ conditions, followed by injection of 20-125M RBCs/mouse into recipient mice. Control animals receive injection with either PBS (challenge control) or free OVA (10 μg/animal—tolerance control). Antigen challenge occurs on day 15, with intradermal injection of 10 μg OVA protein+50 ng LPS/mouse in challenged animals. Draining lymph nodes and spleens of each mouse are analyzed on day 19 and OT-I and OT-II T cell response to antigen challenge is measured by flow cytometry for the number of OT-I and OT-11 T cells and IFN-γ intracellular staining and ELISpot assays. A schematic of a representative treatment schedule is shown in FIG. 7, and the treatment groups are summarized in Table 3.

TABLE 3

| Group | Day 0 | Days 1 & 5 | Day 8 |
|---|---|---|---|
| Challenge Control | OT-I and OT-II adoptive transfer | PBS | OVA + LPS |
| Tolerance Control | OT-I and OT-II adoptive transfer | OVA protein | OVA + LPS |
| RBC-Endo | OT-I and OT-II adoptive transfer | RBCs incubated with OVA without constriction | OVA + LPS |
| RBC-SQZ | OT-I and OT-II adoptive transfer | RBCs incubated with OVA with constriction | OVA + LPS |

Example 6A: Prophylaxis in Murine Type-I Diabetes Model

Introduction

To determine the ability of RBCs containing antigen delivered by SQZ induce antigen-dependent tolerance in a prophylaxis in vivo model of murine type-I diabetes, the levels of blood glucose will be measured weekly over time after tolerance induction.

Materials and Methods

Figure 11B:
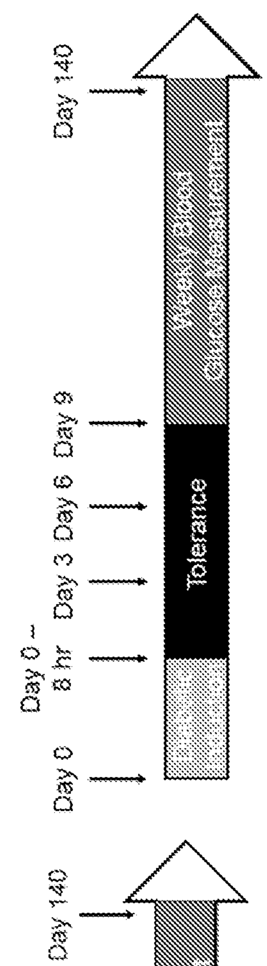
FIGS. 11A and 11B show schematics of representative treatment schedules.
Figure 11A:
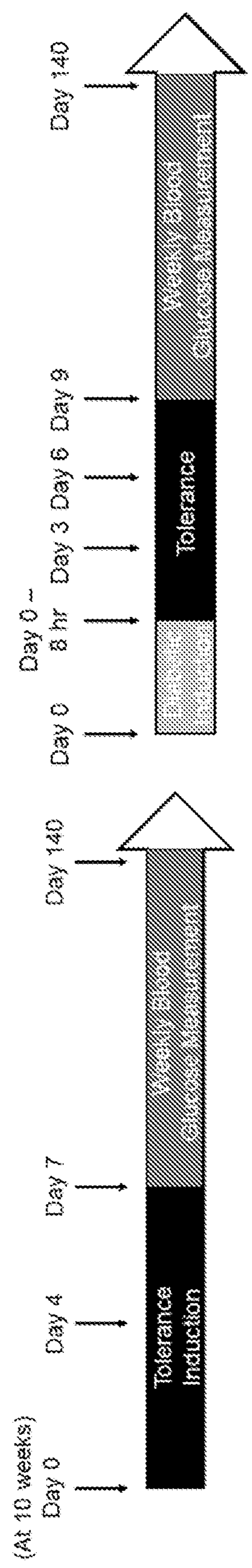

NOD/ShiltJ mice are treated with RBCs at 10 weeks of age. On days 0 (prime) and 5 (boost), RBCs from NOD/ShiltJ mice are harvested and RBCs are incubated with insulin B-chain peptide 9-23 ($InsB_{9-23}$: CKKGSSHLVEALYLVCGERG, SEQ ID NO: 2) or $InsB_{9-23}$ is delivered by SQZ conditions, followed by injection of 20-125M RBCs/mouse into recipient mice. Control animals receive injection with PBS (challenge control). Blood glucose measurements are carried out weekly, starting on Day 7 after treatment (age 11 weeks). Mice are considered diabetic when their blood glucose level exceeded 260 mg/dL as measured by Bayer Contour Diabetes Meter/Glucose Test Strip. A schematic of a representative treatment schedule is shown in FIG. 11A, and the treatment groups are summarized in Table 4.

TABLE 4

| Group | Days 0 and 5 |
|---|---|
| Challenge control | PBS |
| APC-Endo | APCs incubated with $InsB_{9-23}$ |
| APC-SQZ | APCs SQZ'd with $InsB_{9-23}$ |

Example 6B: Therapy in Murine Type-I Diabetes Model

Introduction

To determine the ability of RBCs containing antigen delivered by SQZ induce antigen-dependent tolerance in a treatment in vivo model of murine type-I diabetes, the levels of blood glucose will be measured weekly over time after tolerance induction in mice.

Materials and Methods

To induce rapid onset of T1D in recipients, CD4 T cells are harvested from BDC2.5 NOD mice, activated ex vivo with p31 mimetope peptide (YVRPLWVRME, SEQ ID NO: 3) for 4 days, and adoptively transferred (5M cells/mouse) into normoglycemic NOD recipients. Tolerance induction begins 8 hours after adoptive transfer, and is repeated every 3 days for a total of 3 doses. Recipients are treated with PBS (challenge control) or 20-125M RBCs incubated with p31 (RBC-Endo) or delivered by SQZ with p31 (RBC-SQZ). Blood glucose is measured every day by Bayer Contour Diabetes Meter/Glucose Test Strip. Mice are considered diabetic when their blood glucose level exceeded 260 mg/dL. A schematic of a representative treatment schedule is shown in FIG. 11B, and the treatment groups are summarized in Table 5.

TABLE 5

| Group | Days 0 and 5 |
|---|---|
| Challenge control | PBS |
| APC-Endo | APCs incubated with $InsB_{9-23}$ |
| APC-SQZ | APCs SQZ'd with $InsB_{9-23}$ |

Example 7A: Prophylaxis in Murine MS-Type Autoimmune Disorder

Introduction

To determine the ability of RBCs containing antigen delivered by SQZ induce antigen-dependent tolerance in an in vivo prophylaxis model of a murine MS-type autoimmune disorder, the clinical score of mobility will be assessed daily over time.

Materials and Methods

Figure 12B:
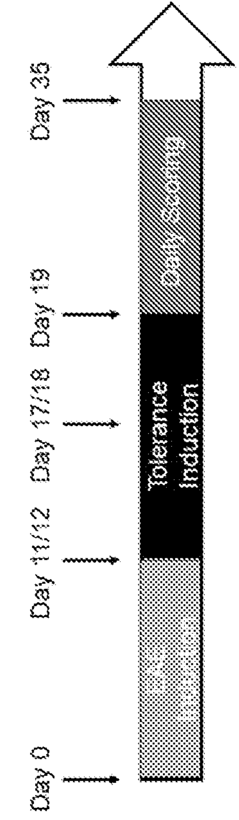
FIGS. 12A and 12B show schematics of representative treatment schedules.
Figure 12A:
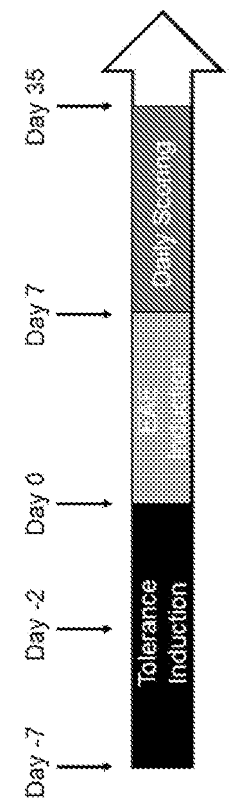

Female C57BL/6 mice (10-12 wks of age) are treated with RBCs prior to induction of experimental autoimmune encephalomyelitis (EAE). On days −7 (prime) and −2 (boost), RBCs from C57BL/6 mice are harvested and RBCs are incubated with myelin oligodendrocyte glycoprotein peptide 35-55 ($MOG_{35-55}$: MEVGWYRSPFSRVVHLYRNGKGS, SEQ ID NO: 4) without constriction, or $OVA_{323-339}$ peptide (negative control: ISQAVHAAHAEINEAGRGS, SEQ ID NO: 5) or $MOG_{35-55}$ peptide is delivered to RBCs by SQZ conditions, followed by injection of 20-125M RBCs/mouse into recipient mice. On Day 0, EAE is induced by administration of $MOG_{35-55}$ in CFA and pertussis toxin in PBS (Hooke kit). Mice are scored daily starting on Day 7, with clinical score defined as follows: 1, limp tail; 2, partial hind leg paralysis; 3, complete hind leg paralysis; 4, complete hind and partial front leg paralysis; and 5, moribund. A schematic of a representative treatment schedule is shown in FIG. 12A, and the treatment groups are summarized in Table 6.

TABLE 6

| Group | Day −7 | Day 0 (Induction of EAE) |
|---|---|---|
| Challenge control | APCs SQZ'd with $OVA_{323-339}$ | $MOG_{35-55}$ + pertussis toxin |
| APC-Endo | APCs incubated with $MOG_{35-55}$ | $MOG_{35-55}$ + pertussis toxin |
| APC-SQZ | APCs SQZ'd with $MOG_{35-55}$ | $MOG_{35-55}$ + pertussis toxin |

Example 7B: Therapy in Murine MS-Type Autoimmune Disorder

Introduction

To determine the ability of RBCs containing antigen delivered by SQZ induce antigen-dependent tolerance in an in vivo model of an established murine MS-type autoimmune disorder, the clinical score of mobility will be assessed daily over time.

Materials and Methods

In female C57BL/6 mice (10-12 wks of age) experimental autoimmune encephalomyelitis (EAE) is induced by administration of $MOG_{33-55}$ in CFA and pertussis toxin in PBS (Hooke kit) on Day 0. Mice are then treated with RBCs on the day of onset of EAE, which occurs once mice are scored ≥1 based on the below mobility criteria. On days ~11/12 (prime) and ~17/18 (boost), RBCs from C57BL/6 mice are harvested and RBCs are incubated with myelin oligodendrocyte glycoprotein peptide 35-55 ($MOG_{35-55}$: MEVGWYRSPFSRVVHLYRNGKGS, SEQ ID NO: 4) without constriction, or $OVA_{323-339}$ peptide (negative control: ISQAVHAAHAEINEAGRGS, SEQ ID NO: 5) or $MOG_{35-55}$ peptide is delivered to RBCs by SQZ conditions, followed by injection of 20-125M RBCs/mouse into recipient mice. Mice are scored daily starting on Day 19, with clinical score defined as follows: 1, limp tail: 2, partial hind leg paralysis: 3, complete hind leg paralysis; 4, complete hind and partial front leg paralysis; and 5, moribund. A schematic of a representative treatment schedule is shown in FIG. 12B, and the treatment groups are summarized in Table 7.

TABLE 7

| Group | Day −7 | Day 0 (Induction of EAE) |
|---|---|---|
| Challenge control | APCs SQZ'd with $OVA_{323-339}$ | $MOG_{35-55}$ + pertussis toxin |
| APC-Endo | APCs incubated with $MOG_{35-55}$ | $MOG_{35-55}$ + pertussis toxin |
| APC-SQZ | APCs SQZ'd with $MOG_{35-55}$ | $MOG_{35-55}$ + pertussis toxin |

Sequence Listing

| SEQ ID NO | Sequence | Description |
|---|---|---|
| 1 | SIINFEKL | CD8+ active OVA epitope |
| 2 | CKKGSSHLVEALYLVCGERG | B-chain peptide 9-23 ($InsB_{9-23}$) |
| 3 | YVRPLWRME | p31 mimetope peptide |
| 4 | MEVGWYRSPFSRVVHLYRNGKGS | myelin oligodendrocyte glycoprotein peptide 35-55 ($MOG_{35-55}$) |
| 5 | ISQAVHAAHAEINEAGRGS | $OVA_{323-339}$ peptide |

What is claimed is:

1. A method for suppressing an immune response in an individual in need thereof, the method comprising:

a. passing a cell suspension comprising a population of anucleate cells through a constriction, wherein the anucleate cells are selected from a red blood cell, platelet, or both, wherein the constriction deforms the anucleate cells, thereby causing a perturbation of the anucleate cells such that an antigen enters the anucleate cells through the perturbation when contacted with the anucleate cells, wherein the perturbation is transient such that after the antigen enters the anucleate cells the perturbation is corrected to produce a population of modified anucleate cells comprising the antigen, and wherein a therapeutically effective dose of the population of modified anucleate cells exhibits reduced viability compared to a population of anucleate cells not having passed through the constriction; and b. introducing the therapeutically effective dose into the individual, wherein the antigen is processed in a tolerogenic environment when the therapeutically effective dose is introduced into the individual, and wherein presentation of the antigen in the tolerogenic environment suppresses an immune response to the antigen.

2. The method of claim 1, wherein the population of modified anucleate cells further comprise a tolerogenic factor.

3. A method for suppressing an immune response in an individual in need thereof, the method comprising introducing into the individual a therapeutically effective dose of a population of modified anucleate cells which comprises an antigen, wherein the antigen was intracellularly delivered to a population of anucleate cells to produce the population of modified anucleate cells by passing the population of anucleate cells through a constriction, wherein the constriction deformed the anucleate cells thereby causing a perturbation of the anucleate cells such that the antigen entered the anucleate cells, wherein the perturbation was transient such that after the antigen entered the anucleate cells the perturbation was corrected, wherein the therapeutically effective dose of the population of modified anucleate cells exhibits reduced viability compared to a population of anucleate cells not having passed through the constriction, wherein the anucleate cells are selected from a red blood cell, platelet, or both, wherein the antigen is processed in a tolerogenic environment after the population of modified anucleate cells are introduced into the individual, and wherein presentation of the antigen in the tolerogenic environment suppresses an immune response to the antigen.

4. A method for delivering a tolerogenic factor into anucleate cells, the method comprising passing a cell suspension comprising a population of the anucleate cells through a constriction, wherein the anucleate cells are selected from a red blood cell, platelet, or both, wherein the constriction deforms the anucleate cells, thereby causing a perturbation of the anucleate cells such that the tolerogenic factor enters the anucleate cells when contacted with the anucleate cells to produce a population of modified anucleate cells comprising the tolerogenic factor, wherein a therapeutically effective dose of the population of modified anucleate cells exhibits reduced viability compared to a population of anucleate cells not having passed through the constriction, and wherein the perturbation is transient such that after the tolerogenic factor enters the anucleate cells the perturbation is corrected.

5. The method of claim 1, wherein the constriction comprises a width, which is a function of the diameter of the anucleate cells.

6. The method of claim 5, wherein the width of the constriction is about 10%, about 20%, about 30%, about 40%, about 50%, about 60%, or about 70% of the diameter of the anucleate cells.

7. The method of claim 1, wherein the cell suspension comprises a mixed cell population.

8. The method of claim 7, wherein the cell suspension is whole blood.

9. The method of claim 1, wherein the cell suspension comprises a purified cell population.

10. The method of claim 9, wherein the cell suspension comprises a purified population of anucleate cells.

11. The method of claim 1, wherein the anucleate cells are human cells.

12. The method of claim 1, wherein the anucleate cells are from the individual.

13. The method of claim 1, wherein the anucleate cells are from a different individual.

14. The method of claim 1, wherein the antigen is located in a cell lysate.

15. The method of claim 1, wherein the antigen is:
(a) a foreign antigen;
(b) a self-antigen; or
(c) an allograft transplantation antigen.

16. The method of claim 1, wherein the antigen is:
(a) a protein or polypeptide;
(b) a lipid antigen; or
(c) a carbohydrate antigen.

17. The method of claim 1, wherein the antigen is a lysate.

18. The method of claim 2, wherein the tolerogenic factor comprises a therapeutic polypeptide or a fragment of a therapeutic polypeptide.

19. The method of claim 2, wherein the tolerogenic factor comprises a polypeptide, wherein the polypeptide is IL-4, IL-10, IL-13, IL-35, IFN<I, or TGFB.

20. The method of claim 1, wherein the suppressed immune response comprises:
(a) decreased production and/or secretion of one or more inflammatory cytokines; and/or
(b) increased production and/or secretion of one or more anti-inflammatory cytokines.

21. The method of claim 20, wherein:
(a) the suppressed immune response comprises decreased production and/or secretion of one or more inflammatory cytokines, wherein the one or more inflammatory cytokines are selected from the group consisting of interleukin-1 (IL-1), IL-12, and IL-18, tumor necrosis factor (TNF), interferon gamma (IFN-γ), and granulocyte-macrophage colony stimulating factor (GM-CSF); and/or
(b) the suppressed immune response comprises increased production and/or secretion of one or more anti-inflammatory cytokines, wherein the one or more anti-inflammatory cytokines are selected from the group consisting of IL-4, IL-10, IL-13, IL-35, IFN-α and transforming growth factor-beta (TGFβ).

22. The method of claim 1, wherein the suppressed immune response comprises a decreased T cell response.

23. The method of claim 22, wherein the decreased T cell response comprises:
(a) decreased T cell activation;
(b) decreased T cell survival;
(c) decreased T cell proliferation;
(d) decreased T cell functionality; and/or
(e) a change in T cell phenotype.

24. The method of claim 1, wherein the suppressed immune response comprises:
(a) uncostimulated activation of a T cell;
(b) an enhanced Treg response;
(c) a decreased B cell response; and/or
(d) decreased cytokine production.

25. The method of claim 1, wherein the suppressed immune response comprises a decreased allergic response.

26. The method of claim 1, wherein the suppressed immune response comprises:
(a) a decreased immune response against the transplanted tissue;
(b) a decreased pathogenic immune response to a virus;
(c) a decreased immune response against a therapeutic agent; and/or
(d) a decreased immune response against a therapeutic vehicle.

27. The method of claim 1, wherein the method is repeated at least 1, 2, 3, 4, 5, or 6 times.

28. The method of claim 1, wherein the antigen is associated with an adenovirus, an adeno-associated virus, a baculovirus, a herpes virus, or a retrovirus.

29. The method of claim 1, wherein the suppressed immune response comprises a decreased immune response against an antigen associated with Type I Diabetes, Rheumatoid arthritis, Psoriasis, Multiple Sclerosis, Systemic Lupus Erthyromatosus, Sjogren's Disease, Crohn's disease, Ulcerative Colitis, or Neurodegenerative disease which may have an immune component.

30. The method of claim 29, wherein the Neurodegenerative disease is Alzheimer's disease, ALS, Huntington's Disease, or Parkinson's Disease.

31. The method of claim 25, wherein the suppressed immune response comprises a decreased allergic response to a food allergen.

32. The method of claim 26, wherein:
(a) the suppressed immune response comprises a decreased pathogenic immune response to a virus, wherein the virus is an adenovirus, an adeno-associated virus, a baculovirus, a herpes virus, or a retrovirus; or
(b) the suppressed immune response comprises a decreased immune response against a therapeutic vehicle, wherein the therapeutic vehicle is an adenovirus, an adeno-associated virus, a baculovirus, a herpes virus, or a retrovirus.

33. The method of claim 26, wherein the therapeutic agent is a clotting factor or a hormone.

34. The method of claim 33, wherein:

(a) the therapeutic agent is a clotting factor and the clotting factor is Factor VIII or Factor IX; or (b) the therapeutic agent is a hormone and the hormone is insulin, human growth hormone, or follicle stimulating hormone.

35. The method of claim 1, wherein the perturbation lasts from $1.0\times10^{-9}$ seconds to 2 hours.

36. The method of claim 3, wherein the perturbation lasts from $1.0\times10^{-9}$ seconds to 2 hours.

37. The method of claim 4, wherein the perturbation lasts from $1.0\times10^{-9}$ seconds to 2 hours.

* * * * *